(12) United States Patent
Mang et al.

(10) Patent No.: US 8,222,447 B2
(45) Date of Patent: Jul. 17, 2012

(54) ORGANIC COMPOUNDS

(75) Inventors: Rosemarie Mang, Vienna (AT); Werner Heilmayer, Zillingtal (AT)

(73) Assignee: Nabriva Therapeutics AG, Vienna (AT)

( * ) Notice: Subject to any disclaimer, the term of this patent is extended or adjusted under 35 U.S.C. 154(b) by 0 days.

(21) Appl. No.: 13/061,692

(22) PCT Filed: Aug. 17, 2009

(86) PCT No.: PCT/AT2009/000313
§ 371 (c)(1),
(2), (4) Date: Apr. 11, 2011

(87) PCT Pub. No.: WO2010/025482
PCT Pub. Date: Mar. 11, 2010

(65) Prior Publication Data
US 2011/0184022 A1    Jul. 28, 2011

(30) Foreign Application Priority Data
Sep. 2, 2008    (EP) ..................... 08450126

(51) Int. Cl.
C07C 205/00    (2006.01)
A01N 37/00    (2006.01)

(52) U.S. Cl. ....................... 560/125; 514/529
(58) Field of Classification Search .............. None
See application file for complete search history.

(56) References Cited

U.S. PATENT DOCUMENTS
2009/0118366 A1* 5/2009 Mang et al. .................. 514/529

FOREIGN PATENT DOCUMENTS

| WO | 0204414 A | 1/2002 |
|---|---|---|
| WO | 03082260 A2 | 3/2003 |
| WO | 03090740 A1 | 11/2003 |
| WO | 2007000004 A | 1/2007 |
| WO | 2007014409 A | 2/2007 |
| WO | 2008113089 A1 | 9/2008 |

OTHER PUBLICATIONS

H. Berner et al, Synthese AB-Trans-Anellierter Derivate Des Tricyclischen Diterpens Pleuromutilin Durch Intramolekulare 1,5-Hydrid-Verschiebung, Tetrahedron, 1980, 1807-1811, vol. 36, Issue 12.

* cited by examiner

*Primary Examiner* — Karl J Puttlitz
(74) *Attorney, Agent, or Firm* — Maschoff Gilmore & Israelsen

(57) ABSTRACT

Compounds of formula (I), which are 14-O-{[(optionally substituted hydroxy)cyclohexyl)sulfanyl]acetyl}mutilins further substituted at the cyclohexyl group by an acylated amino group, salts and solvates thereof, pharmaceutical compositions comprising such compounds and their use as a pharmaceutical, e.g. for the treatment of diseases mediated by microbes and for the treatment of inflammation where microbes are mediating said inflammation.

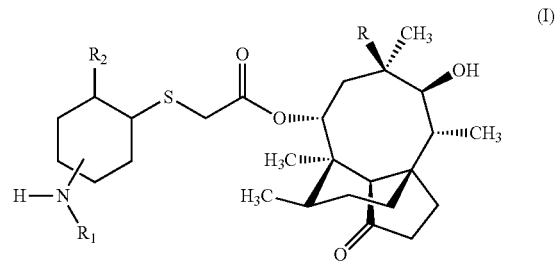

13 Claims, No Drawings

ORGANIC COMPOUNDS

The present invention relates to organic compounds, such as pleuromutilins.

Pleuromutilin, a compound of formula A

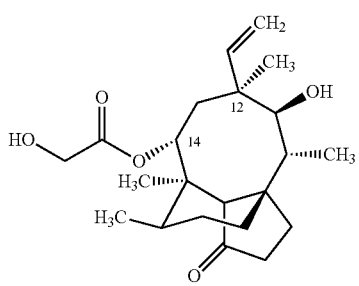

is a naturally occurring antibiotic, e.g. produced by the basidomycetes *Pleurotus mutilus* and *P. passeckerianus*, see e.g. The Merck Index, 13th edition, item 7617. A number of further pleuromutilins having the principle ring structure of pleuromutilin and being substituted at the hydroxy group have been developed, e.g. as antimicrobials.

From WO 02/04414 A1 e.g. 14-O-[(Aminocyclohexan-2-yl (and -3-yl)-sulfanyl)-acetyl]-mutilins, from WO 2007/014409 e.g. 14-O-[((Mono- or dialkylamino)-cycloalkylsulfanyl)-acetyl]-mutilins, from WO 2007/000004 e.g. [((Acyl-hydroxy-amino)-cycloalkylsulfanyl)-acetyl]-mutilins, and from WO 03/082260 e.g. 14-O-[(4-(R)-Valyl-aminocyclohexan-1-yl-sulfanyl)-acetyl]mutilins are known.

Now, surprisingly, we have found pleuromutilins with interesting activity combined with an unexpected remarkable metabolic stability.

In one aspect the present invention provides a compound of formula

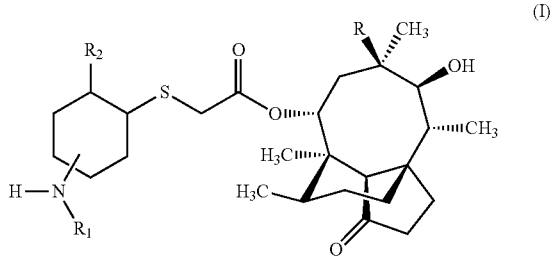

wherein
R is ethyl or vinyl;
$R_1$ is a group of formula

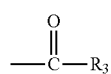

$R_2$ is OH or $OR_1$; and
$R_3$ is hydrogen, straight chain or branched $(C_{1-8})$alkyl or $(C_{3-8})$cycloalkyl, or
is that part of an natural amino acid in D or in L form which remains if the carboxylic acid group is split off, or
is that part of an non natural amino acid in D or in L form which remains if the carboxylic acid group is split off.

In a compound of formula I in one aspect R is ethyl.
In a compound of formula I in another aspect R is vinyl.
In a compound of formula I $R_2$ is preferably hydroxy, formyloxy, or $(C_{1-4})$alkylcarbonyloxy; such as hydroxy, formyloxy or acetoxy.

In another aspect the present invention provides a compound of formula I, wherein $R_2$ is hydroxy.

In another aspect the present invention provides a compound of formula I wherein $R_2$ is formyloxy or $(C_{1-4})$alkylcarbonyloxy.

In another aspect in a compound of formula I $R_3$ is preferably hydrogen.

In another aspect in a compound of formula I $R_3$ is preferably straight chain or branched $(C_{1-8})$alkyl.

In another aspect in a compound of formula I $R_3$ is preferably $(C_{3-8})$cycloalkyl.

In another aspect in a compound of formula I $R_3$ is preferably that part of an natural or non natural amino acid, which remains if the carboxylic acid group is split off.

In another aspect in a compound of formula I $R_3$ is preferably that part of a natural amino acid, which remains if the carboxylic acid group is split off.

In another aspect in a compound of formula I $R_3$ is preferably that part of a non natural amino acid, which remains if the carboxylic acid group is split off.

If in a compound of formula I $R_3$ is straight chain or branched $(C_{1-8})$alkyl, $R_3$ is preferably $(C_{1-6})$alkyl, such as methyl, isopropyl or tert-butyl.

If in a compound of formula I $R_3$ is $(C_{3-8})$cycloalkyl, $R_3$ is preferably $(C_{3-6})$cycloalkyl, such as cyclopropyl.

If $R_3$ in a compound of formula I is that part of an natural or non natural amino acid, which remains if the carboxylic acid group is split off, said amino acid is preferably an alpha-amino acid.

If $R_3$ in a compound of formula I is that part of an natural or non natural amino acid in D- or in L-form, which remains if the carboxylic acid group is split off, $R_3$ is preferably heterocyclyl, e.g. including aromatic and aliphatic heterocyclyl, e.g. aliphatic heterocyclyl, comprising 3 to 8 ring members, e.g. 5 or 6, and comprising 1 to 4 heteroatoms selected from N, O and/or S and comprising as a heteroatom at least one nitrogen atom, e.g. which nitrogen atom preferably is in alpha position, such as pyrrolidinyl, e.g. pyrrolidin-2-yl, or piperidinyl, e.g. piperidin-2-yl, or $R_3$ is straight chain or branched $(C_{1-8})$alkyl, e.g. $(C_{1-6})$alkyl, which is substituted by amino and optionally further substituted by hydroxy, amino, which amino optionally is substituted by heterocyclylcarbonyl, wherein heterocyclyl includes aromatic and aliphatic heterocyclyl, including 5 to 6 ring members, e.g. 5, and 1 to 4 heteroatoms selected from N, O and/or S, e.g. N, such as methyl-dihydropyrrolidine-carbonyl; guanidino, aminocarbonyl, carboxy, mercapto, $(C_{1-4})$alkylmercapto, e.g. methylmercapto, phenyl, e.g. including hydroxyphenyl, seleno, or heterocyclyl, e.g. inducing aromatic and aliphatic heterocyclyl, comprising 3 to 8, e.g. 5 to 6 ring members and comprising 1 to 4 heteroatoms, e.g. 1 or 2, selected from N, O and/or S, e.g. N, which heterocyclyl optionally is fused with another ring system, e.g. fused with phenyl;

more preferably aliphatic heterocyclyl, comprising 5 or 6 ring members and at least one nitrogen atom, e.g. which nitrogen atom preferably is in alpha position, such as pyrrolidinyl, e.g. pyrrolidin-2-yl, or piperidinyl, e.g. piperidin-2-yl, or straight chain or branched $(C_{1-6})$alkyl substituted by amino and optionally further substituted by hydroxy.

If $R_3$ in a compound of formula I is that part of a natural amino acid in D or in L form, which remains if the carboxylic acid group is split off, $R_3$ e.g. includes the amino acid residue which remains if the carboxylic acid group is split off from alanine, cysteine, aspartic acid, glutamic acid, phenylalanine, glycine, histidine, isoleucine, lysine, leucine, methionine, asparagine, pyrrolysine, proline, glutamine, arginine, serine, threonine, selenocysteine, valine, tryptophan or tyrosin, more preferably alanine, serine or valin.

If $R_3$ in a compound of formula I is that part of a non natural amino acid in D or in L form, which remains if the carboxylic acid group is split off, $R_3$ is preferably aliphatic heterocyclyl, comprising 3 to 8, e.g. 5 to 6 ring members and comprising 1 to 4 heteroatoms, e.g. 1 or 2, such as piperidinyl, e.g. piperidin-2-yl.

In a compound of formula I $R_3$ is more preferably hydrogen, methyl, isopropyl, tert-butyl, cyclopropyl, or the residue of a natural amino acid which remains if the carboxylic acid is split off wherein the amino acid is selected from L- or D-alanine, -serine, -valine, or $R_3$ is -piperidinyl, e.g. piperidin-2-yl.

In another aspect in a compound of formula I the —NH—$R_1$ group attached to the cyclohexyl ring is in position 5 of the cyclohexyl ring.

In another aspect the present invention provides a compound of formula

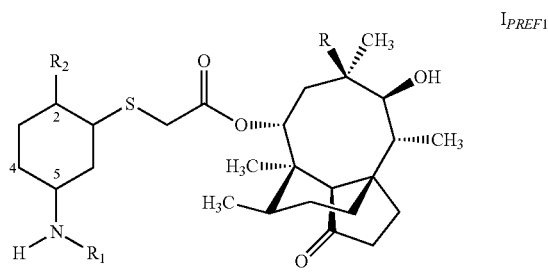

$I_{PREF1}$ wherein $R_1$ and $R_2$ are as defined above.

In another aspect in a compound of formula I the —NH—$R_1$ group attached to the cyclohexyl ring is in position 4 of the cyclohexyl ring.

In another aspect the present invention provides a compound of formula

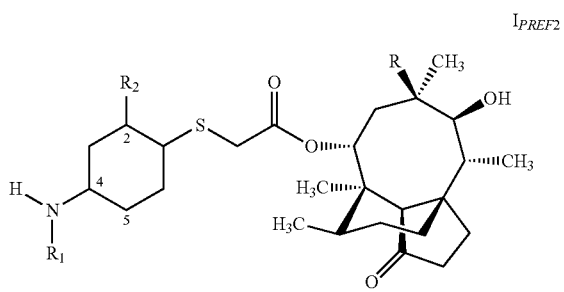

$I_{PREF2}$ wherein $R_1$ and $R_2$ are as defined above.

A compound of formula I includes a compound of formula $I_{PREF1}$ and of $I_{PREF2}$.

In a compound of formula I each single group of substitutents defined may be a preferred group of substitutents, e.g. independently of each other group of substitutents or single substitutents defined. In a compound of formula I each single substituent defined, may be a preferred substituent, e.g. independently of each other group of substitutents or single substitutent defined.

In another aspect the present invention provides a compound of Examples 4 to 42 below, namely a compound of formula I which is selected from the group consisting of 14-O-{[(1S,2S,4S)-4-(R)-2-Amino-3-methyl-butyrylamino)-2-hydroxy-cyclohexylsulfanyl]acetyl}-mutilin, 14-O-{[(1R,2R,4R)-4-((R)-2-Amino-3-methyl-butyrylamino)-2-hydroxy-cyclohexylsulfanyl]-acetyl}-mutilin, 14-O-{[(1S,2S,4S)-4-((S)-2-Amino-3-methyl-butyrylamino)-2-hydroxy-cyclohexylsulfanyl]-acetyl}-mutilin, 14-O-{[(1R,2R,4R)-4-((S)-2-Amino-3-methyl-butyrylamino)-2-hydroxy-cyclohexylsulfanyl]-acetyl}-mutilin.

14-O-{[(1S,2S,4S)-4-((R)-2-Amino-propionylamino)-2-hydroxy-cyclohexylsulfanyl]-acetyl}-mutilin, 14-O-{[(1R,2R,4R)-4-(R)-2-Amino-propionylamino)-2-hydroxy-cyclohexylsulfanyl]-acetyl}-mutilin, 14-O-{[(1S,2S,4S)-4-(S)-2-Amino-propionylamino)-2-hydroxy-cyclohexylsulfanyl]-acetyl}-mutilin, 14-O-{[(1R,2R,4R)-4-(R)-2-Amino-propionylamino)-2-hydroxy-cyclohexylsulfanyl]-acetyl}-mutilin, 14-O-{[(1S,2S,4S)-2-Hydroxy-4-[((R)-piperidine-2-carbonyl)-amino]-cyclohexylsulfanyl]-acetyl}-mutilin, 14-O-{[(1R,2R,4R)-2-Hydroxy-4-[((R)-piperidine-2-carbonyl)-amino]-cyclohexylsulfanyl]-acetyl}-mutilin, 14-O-{[(1S,2S,4S)-2-Hydroxy-4-[((S)-piperidine-2-carbonyl)-amino]-cyclohexylsulfanyl]-acetyl}-mutilin, 14-O-{[(1R,2R,4R)-2-Hydroxy-4-[((S)-piperidine-2-carbonyl)-amino]-cyclohexylsulfanyl]-acetyl}-mutilin, 14-O-{[(1S,2S,4S)-4-((R)-2-Amino-3-hydroxy-propionylamino)-2-hydroxy-cyclohexylsulfanyl]-acetyl}-mutilin and the (1R,2R,4R) diastereomer thereof, 14-O-{[(1S,2S,5R)-5-((R)-2-Amino-3-methyl-butyrylamino)-2-hydroxy-cyclohexylsulfanyl]-acetyl}-mutilin, 14-O-{[(1R,2R,5S)-5-((R)-2-Amino-3-methyl-butyrylamino)-2-hydroxy-cyclohexylsulfanyl]-acetyl}-mutilin, 14-O-{[(1S,2S,5R)-5-((S)-2-Amino-3-methyl-butyrylamino)-2-hydroxy-cyclohexylsulfanyl]-acetyl}-mutilin, 14-O-{[(1R,2R,5S)-5-((S)-2-Amino-3-methyl-butyrylamino)-2-hydroxy-cyclohexylsulfanyl]-acetyl}-mutilin, 14-O-{[(1S,2S,5R)-5-((S)-2-Amino-3-methyl-butyrylamino)-2-hydroxy-cyclohexylsulfanyl]-acetyl}-19,20-dihydro-mutilin, 14-O-{[(1R,2R,5S)-5-((S)-2-Amino-3-methyl-butyrylamino)-2-hydroxy-cyclohexylsulfanyl]-acetyl}-19,20-dihydro-mutilin, 14-O-{[(1S,2S,5R)-5-((R)-2-Amino-propionylamino)-2-hydroxy-cyclohexylsulfanyl]-acetyl}-mutilin, 14-O-{[(1R,2R,5S)-5-((R)-2-Amino-propionylamino)-2-hydroxy-cyclohexylsulfanyl]-acetyl}-mutilin, 14-O-{[(1S,2S,5R)-5-((S)-2-Amino-propionylamino)-2-hydroxy-cyclohexylsulfanyl]-acetyl}-mutilin and the (1R,2R,5S) diastereomer thereof, 14-O-{[(1S,2S,5R)-2-Hydroxy-5-[((R)-piperidine-2-carbonyl)-amino]-cyclohexylsulfanyl]-acetyl}-mutilin, 14-O-{[(1R,2R,5S)-2-Hydroxy-5-[((R)-piperidine-2-carbonyl)amino]cyclohexylsulfanyl]-acetyl}-mutilin, 14-O-{[(1S,2S,5R)-2-Hydroxy-5-[((R)-piperidine-2-carbonyl)-amino]-cyclohexylsulfanyl]-acetyl}-19,20-dihydro-mutilin, 14-O-{[(1R,2R,5S)-2-Hydroxy-5-[((R)-piperidine-2-carbonyl)-amino]-cyclohexylsulfanyl]-acetyl}-19,20-dihydro-mutilin, 14-O-{[(1S,2S,5R)-2-Hydroxy-5-[((S)-piperidine-2-carbonyl)-amino]-cyclohexylsulfanyl]-acetyl}-mutilin,
14-O-{[(1R,2R,5S)-2-Hydroxy-5-[((S)-piperidine-2-carbonyl)-amino]-cyclohexylsulfanyl]-acetyl}-mutilin,
14-O-{[(1S,2S,5R)-2-Hydroxy-5-[((S)-piperidine-2-carbonyl)-amino]cyclohexylsulfanyl]-acetyl}-19,20-dihydromutilin,
14-O-{[(1R,2R,5S)-2-Hydroxy-5-[((S)-piperidine-2-carbonyl)-amino]-cyclohexylsulfanyl]-acetyl}-19,20-dihydromutilin,
14-O-{[(1S,2S,5R)-5-((R)-2-Amino-3-hydroxy-propionylamino)-2-hydroxy-cyclohexylsulfanyl]-acetyl}-mutilin,
14-O-{[(1R,2R,5S)-5-((R)-2-Amino-3-hydroxy-propionylamino)-2-hydroxy-cyclohexylsulfanyl]-acetyl}-mutilin,
14-O-{[(1S,2S,5R)-5-((S)-2-Amino-3-hydroxy-propionylamino)-2-hydroxy-cyclohexylsulfanyl]-acetyl}-mutilin and the (1R,2R,5S) diastereomer thereof,
14-O-{[(1S,2S,5S)-5-((R)-2-Amino-3-methyl-butyrylamino)-2-hydroxy-cyclohexylsulfanyl]-acetyl}-mutilin,
14-O-{[(1R,2R,5R)-5-((R)-2-Amino-3-methyl-butyrylamino)-2-hydroxy-cyclohexylsulfanyl]-acetyl}-mutilin,
14-O-{[(1S,2S,5S)-5-((R)-2-Amino-propionylamino)-2-hydroxy-cyclohexylsulfanyl]-acetyl}-mutilin,
14-O-{[(1R,2R,5R)-5-((R)-2-Amino-propionylamino)-2-hydroxy-cyclohexylsulfanyl]-acetyl}-mutilin,
14-O-{[(1S,2S,5S)-2-Hydroxy-5-[((R)-piperidine-2-carbonyl)-amino]-cyclohexylsulfanyl]-acetyl}-mutilin,
14-O-{[(1R,2R,5R)-2-Hydroxy-5-[((R)-piperidine-2-carbonyl)-amino]-cyclohexylsulfanyl]-acetyl}-mutilin,
14-O-{[(1S,2S,5S)-5-((R)-2-Amino-3-hydroxy-propionylamino)-2-hydroxy-cyclohexylsulfanyl]-acetyl}-mutilin and the (1R,2R,5R) diastereomer thereof,
14-O-[((1S,2S,4S)-4-Formylamino-2-hydroxy-cyclohexylsulfanyl)-acetyl]-mutilin and the (1R,2R,4R) diastereomer thereof,
14-O-[((1S,2S,4S)-4-Acetylamino-2-hydroxy-cyclohexylsulfanyl)-acetyl]mutilin and the (1R,2R,4R) diastereomer thereof,
14-O-[((1S,2S,4S)-2-Hydroxy-4-isobutyrylamino-cyclohexylsulfanyl)-acetyl]-mutilin and the (1R,2R,4R) diastereomer thereof,
14-O-{[(1S,2S,4S)-4-(2,2-Dimethyl-propionylamino)-2-hydroxy-cyclohexylsulfanyl]-acetyl}-mutilin and the (1R,2R,4R) diastereomer thereof,
14-O-{[(1S,2S,4S)-4-(Cyclopropanecarbonyl-amino)-2-hydroxy-cyclohexylsulfanyl]-acetyl}-mutilin and the (1R,2R,4R) diastereomer thereof,
14-O-[((1S,2S,5R)-5-Formylamino-2-hydroxy-cyclohexylsulfanyl)-acetyl]-mutilin and the (1R,2R,5S) diastereomer thereof,
14-O-[((1S,2S,5R)-5-Formylamino-2-formyloxy-cyclohexylsulfanyl)-acetyl]mutilin and the (1R,2R,5S) diastereomer thereof,
14-O-[((1S,2S,5R)-5-Acetylamino-2-hydroxy-cyclohexylsulfanyl)-acetyl]mutilin and the (1R,2R,5S) diastereomer thereof,
14-O-[((1S,2S,5R)-2-Acetoxy-5-acetylamino-cyclohexylsulfanyl)-acetyl]-mutilin and the (1R,2R,5S) diastereomer thereof,
14-O-[((1S,2S,5R)-2-Hydroxy-5-isobutyrylamino-cyclohexylsulfanyl)-acetyl]-mutilin and the (1R,2R,5S) diastereomer thereof,
14-O-{[(1S,2S,5R)-5-(2,2-Dimethyl-propionylamino)-2-hydroxy-cyclohexylsulfanyl]-acetyl}-mutilin and the (1R,2R,5S) diastereomer thereof,
14-O-{[(1S,2S,5R)-5-(Cyclopropanecarbonyl-amino)-2-hydroxy-cyclohexyl sulfanyl]-acetyl}-mutilin and the (1R,2R,5S) diastereomer thereof,
14-O-[((1S,2S,5S)-5-Formylamino-2-hydroxy-cyclohexylsulfanyl)-acetyl]-mutilin and the (1R,2R,5R) diastereomer thereof,
14-O-[((1S,2S,5S)-5-Acetylamino-2-hydroxy-cyclohexylsulfanyl)-acetyl]-mutilin and the (1R,2R,5R) diastereomer thereof,
14-O-[((1S,2S,5S)-2-Hydroxy-5-isobutyrylamino-cyclohexylsulfanyl)-acetyl]-mutilin and the (1R,2R,5S) diastereomer thereof,
14-O-{[(1S,2S,5S)-5-(2,2-Dimethyl-propionylamino)-2-hydroxy-cyclohexylsulfanyl]-acetyl}-mutilin and the (1R,2R,5R) diastereomer thereof, and
14-O-{[(1S,2S,5S)-5-(Cyclopropanecarbonyl-amino)-2-hydroxy-cyclohexylsulfanyl]-acetyl}-mutilin and the (1R,2R,5R) diastereomer thereof.

In another aspect the present invention provides 14-O-{[(2-hydroxy-, 2-formyloxy- or 2-acetoxy-cyclohexyl)sulfanyl]-acetyl}-mutilins which are further substituted at the cyclohexyl group by an acylated amino group.

A compound provided by the present invention is herein also designated as "compound(s) of (according to) the present invention". A compound of the present invention includes a compound in any form, e.g. in free form, in the form of a salt, if a salt forming group is present, in the form of a solvate and in the form of a salt and a solvate.

In another aspect, the present invention provides a compound of the present invention in the form of a salt, if a salt forming group is present, e.g. and/or solvate.

Such salts include preferably pharmaceutically acceptable salts, although pharmaceutically unacceptable salts are included, e.g. for preparation/isolation/purification purposes. A salt of a compound of the present invention includes a base salt or an acid addition salt. Pharmaceutically acceptable base salts include ammonium salts such as trimethylammonium salt, alkali metal salts such as those of sodium and potassium, alkaline earth metal salts such as those of calcium and magnesium, and salts with organic bases, including salts of primary, secondary and tertiary amines, such as isopropylamine, diethylamine, ethanolamine, trimethylamine, dicyclohexyl amine and N-methyl-D-glucamine, preferably sodium salts. Acid addition salts include salts of a compound of the present invention with an acid, e.g. hydrogen fumaric acid, fumaric acid, tartaric acid, ethane-1,2-disulfonic acid, maleic acid, naphthalin-1,5-sulfonic acid, acetic acid, maleic acid, succinic acid, salicylic acid, azelaic acid, 2-[(2,6-dichlorophenyl)amino]benzene acetic acid, hydrochloric acid, deuterochloric acid, preferably hydrochloric acid.

A compound of the present invention in free form may be converted into a corresponding compound in the form of a salt, and vice versa. A compound of the present invention in free form or in the form of a salt and/or in the form of a solvate may be converted into a corresponding compound in free form or in the form of a salt in non-solvated form, and vice versa.

A compound of the present invention may exist in the form of isomers and mixtures thereof, e.g. optical isomers, diastereoisomers, cis/trans conformers. A compound of the present invention may e.g. contain asymmetric carbon atoms and may thus exist in the form of enantiomers or diastereoisomers and mixtures thereof, e.g. racemates or diastereomeric mixtures. Any asymmetric carbon atom may be present in the (R)-, (S)- or (R,S)-configuration, preferably in the (R)- or (S)-configuration.

For example, in a compound of formula I the carbon atom of the cycloalkyl ring which is attached to sulfur atom, the carbon atom of the cycloalkyl ring which is attached to the $R_2$ group, and the carbon atom of the cycloalkyl ring to which the $NHR_1$ group is attached, all are asymmetric carbon atoms. Substituents attached to such asymmetric carbon atom may thus exist in (R) and (S) configuration, including mixtures thereof. For example, if in a compound of formula I $R_1$ is $COR_3$ and $R_3$ is that part of an amino acid which remains if the carboxylic acid group is split off, the amino acid may be in the (R)- and (S)-configuration (D or L form), including mixtures thereof. For example, if in a compound of formula I $R_1$ is $COR_3$ and $R_3$ is branched alkyl and that branch is attached to a carbon atom of the side chain of such alkyl, the carbon atom to which such substituent is attached can be an asymmetric carbon atom and such substituent may be in the (R)- and (S)-configuration, including mixtures thereof.

The configuration of substituents attached to asymmetric carbon atoms of the mutilin-tricyclus is preferably the same as in natural pleuromutilin.

Isomeric mixtures may be separated as appropriate, e.g. according, e.g. analogously, to a method as conventional, to obtain pure isomers. The present invention includes a compound of the present invention in any isomeric form and in any isomeric mixture. The present invention also includes tautomers of a compound of the present invention, where tautomers can exist.

In another aspect the present invention provides a process for the production of a compound of the present invention, e.g. of formula I, comprising the steps of
a. acylating a compound of formula

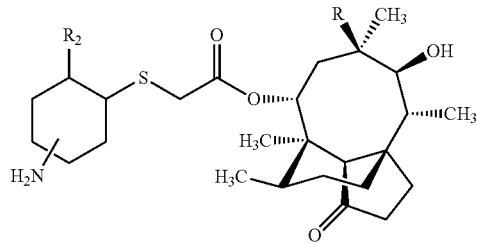

wherein R and $R_2$ are as defined above, with a compound of formula

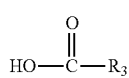

wherein $R_3$ is as defined above, optionally in activated form, e.g. in the form of a halogenide, or in the form of an anhydride, and
b. isolating a compound of formula I obtained, wherein R, $R_2$ and $R_3$ are as defined above from the reaction mixture.

The above reaction is an amine acylation reaction and may be carried out as appropriate, e.g. according, such as analogously, to a method as conventional, e.g. or as described herein. In an intermediate of formula II or of formula III (starting materials) functional groups, if present, optionally may be in protected form or in the form of a salt, if a salt forming group is present. Protecting groups, optionally present, may be removed at an appropriate stage, e.g. according, e.g. analogously, to a method as conventional.

A compound of formula I thus obtained may be converted into another compound of formula I, e.g. or a compound of formula I obtained in free form may be converted into a salt of a compound of formula I and vice versa. E.g. a compound of formula I, wherein $R_2$ is hydroxy may be converted into a compound of formula I wherein $R_2$ is other than hydroxy.

Intermediates (starting materials) of formula II or of formula III are known or may be prepared according, e.g. analogously, to a method as conventional or as specified herein.

Any compound described herein, e.g. a compound of the present invention and intermediates of formula II or of formula III may be prepared as appropriate, e.g. according, e.g. analogously, to a method as conventional, e.g. or as specified herein.

The compounds of the present invention exhibit pharmacological activity and are therefore useful as pharmaceuticals.

For example, the compounds of the present invention show antimicrobial, e.g. antibacterial, activity against gram positive bacteria, such as coagulase positive Staphylococci, e.g. *Staphylococcus aureus*, coagulase negative Staphylococci, e.g. *Staphylococcus epidermidis, Staphylococcus haemolyticus*, and Streptococci, e.g. *Streptococcus pyogenes, Streptococcus pneumoniae*, Enterococci, e.g. *Enterococcus faecium* and *Listeria monocytogenes* and against gram negative bacteria such as *Moraxella*, e.g. *Moraxella catarrhalis*, and *Haemophilus*, e.g. *Haemophilus influenzae*, and *Legionella*, e.g. *Legionella pneumophila*, Neisseriaceae, e.g. *Neisseria gonorrhoeae*, as well as against Mycoplasms, *Chlamydia* and obligatory anaerobes, e.g. *Bacteroides fragilis, Clostridium difficile, Fusobacterium* spp., and *Propionibacterium* spp.

The in vitro activity against aerobic bacteria is determined by Agar Dilution TEST or Microdilution TEST according to the Clinical and Laboratory Standards Institute (CLSI, former NCCLS) Document M7-A7 Vol. 26, No. 2: "Methods for dilution Antimicrobial Susceptibility Tests for Bacteria that Grow Aerobically—Approved Standard; Seventh Edition (2006)"; and the TEST against anaerobic bacteria is performed according to the Clinical and Laboratory Standards Institute (CLSI, former NCCLS), Document, M11-A6, Vol. 24, No. 2: "Methods for Antimicrobial Susceptibility Testing of Anaerobic Bacteria—Approved Standard; Sixth Edition (2004)" and the in vivo activity is tested by the septicaemia mouse model against *Staphylococcus aureus* (in vivo TEST).

Compounds of the present invention show activity in such TESTs and are therefore suitable for the treatment and prevention of diseases which are mediated by microbes, e.g. by bacteria. Diseases which may also be treated include e.g. diseases mediated by *Helicobacter*, such as *Helicobacter pylori*, and diseases mediated by *Mycobacterium tuberculosis*. Diseases which may also be treated include in general inflammatory diseases, where microbes are mediating said inflammation, e.g. including acne.

In another aspect the present invention provides a compound of the present invention for use as a pharmaceutical, preferably as an antimicrobial, such as an antibiotic, e.g. and an anti-anaerobic.

In another aspect the present invention provides a compound of the present invention for use in acne treatment.

In a further aspect the present invention provides a compound of the present invention for use in the preparation of a medicament for the treatment of diseases, mediated by microbes, such as bacterias, for example
diseases mediated by bacteria, e.g. selected from Staphylococci, Streptococci, Enterococci;

diseases mediated by bacteria, e.g. selected from *Moraxella, Haemophilus, Legionella*, Neisseriaceae; diseases mediated by *Helicobacter*; diseases mediated by *Mycobacterium tuberculosis*; e.g. diseases mediated by Mycoplasms, *Chlamydia* and obligatory anaerobes; and for the treatment of acne.

In a further aspect the present invention provides a method of treatment of diseases mediated by microbes which method comprises administering to a subject in need of such treatment an effective amount of a compound of the present invention e.g. in the form of a pharmaceutical composition.

In a further aspect the present invention provides a method of treatment of acne which method comprises administering to a subject in need of such treatment an effective amount of a compound of the present invention e.g. in the form of a pharmaceutical composition.

Treatment includes treatment and prophylaxis (prevention), preferably treatment.

For antimicrobial and acne treatment, the appropriate dosage will, of course, vary depending upon, for example, the chemical nature and the pharmacokinetic data of a compound of the present invention employed, the individual host, the mode of administration and the nature and severity of the conditions being treated. However, in general, for satisfactory results in larger mammals, for example humans, an indicated daily dosage is in the range from about 0.5 mg to 3 g of a compound of the present invention conveniently administered, for example, in divided doses up to four times a day.

A compound of the present invention may be administered by any conventional route, for example enterally, e.g. including nasal, buccal, rectal, oral administration; parenterally, e.g. including intravenous, intramuscular, subcutaneous administration; or topically, e.g. including epicutaneous, intranasal, intratracheal administration, e.g. in form of coated or uncoated tablets, capsules, injectable solutions or suspensions, e.g. in the form of ampoules, vials, in the form of creams, gels, pastes, inhaler powder, foams, tinctures, lipsticks, drops, sprays, or in the form of suppositories, e.g. in analogous manner to macrolides, such as erythromycins, e.g. clarithromycin or azithromycin.

A compound of the present invention may be administered in the form of a pharmaceutically acceptable salt, if a salt forming group is present, e.g. an acid addition salt or a base addition salt, e.g. a metal salt, or in free form, optionally in the form of a solvate. A compound of the present invention in the form of a salt exhibits the same order of activity as the compound in free form, optionally in the form of a solvate.

A compound of the present invention may be used for pharmaceutical treatment according to the present invention alone or in combination with one or more other pharmaceutically active agents. Such other pharmaceutically active agents include e.g. other antibiotics and antiinflammatory agents, and, if a compound of the present invention is used in the treatment of acne, other pharmaceutically agents include furthermore agents which are active against acne.

Combinations include fixed combinations, in which two or more pharmaceutically active agents are in the same formulation; kits, in which two or more pharmaceutically active agents in separate formulations are sold in the same package, e.g. with instruction for co-administration; and free combinations in which the pharmaceutically active agents are packaged separately, but instruction for simultaneous or sequential administration are given.

In another aspect the present invention provides a pharmaceutical composition comprising a compound of the present invention, e.g. in free form or in the form of a pharmaceutically acceptable salt, e.g. and/or in the form of a solvate, in association with at least one pharmaceutically acceptable excipient, e.g. carrier or diluent, e.g. including fillers, binders, disintegrators, flow conditioners, lubricants, sugars and sweeteners, fragrances, preservatives, stabilizers, wetting agents and/or emulsifiers, solubilizers, salts for regulating osmotic pressure and/or buffers.

In another aspect the present invention provides a pharmaceutical composition according to the present invention, further comprising another pharmaceutically active agent.

Such pharmaceutical compositions may be manufactured according, e.g. analogously, to a method as conventional, e.g. by mixing, granulating, coating, dissolving or lyophilizing processes. Unit dosage form may contain, for example, from about 0.5 mg to about 2000 mg, such as 10 mg to about 1000 mg.

The compounds of the present invention are additionally suitable as veterinary agents, e.g. veterinary active compounds, e.g. in the prophylaxis and in the treatment of microbial, e.g. bacterial diseases, in animals, such as fowl, pigs and calves, e.g., and for diluting fluids for artificial insemination and for egg-dipping techniques.

In another aspect the present invention provides a compound of the present invention for use as a veterinary agent.

In a further aspect the present invention provides a compound of the present invention for the preparation of a veterinary composition which is useful as a veterinary agent.

In another aspect the present invention provides a veterinary method for the prophylaxis and the treatment of microbial, e.g. bacterial diseases which comprises administering to a subject in need of such treatment an effective amount of a compound of the present invention, e.g. in the form of a veterinary composition.

The compounds of examples 4 to 42 as described herein exhibit MICs of $\leq 2$ µg/mL against *Staphylococcus aureus* ATCC49951 and *Streptococcus pneumoniae* ATCC49619.

The metabolic stability of compounds of the present invention is determined by using cryopreserved primary human hepatocytes. $1 \times 10^6$ cells/mL are incubated for 4 hours with 5 µg/mL of the test compounds at 37° C., 5% $CO_2$. Samples are taken at t=0 hours and t=4 hours. The incubation is stopped by dilution with acetonitrile and freezing of the mixture. After centrifugation, the samples are analyzed for loss of parent compound between t=0 hours and t=4 hours using reversed phase LC/MS and the metabolic stability value corresponds to the detected parent compound in % after incubation.

It was surprisingly found that the compounds of the present invention reveal unexpected improvements in metabolic stability compared with compounds of the prior art. Compounds of the present invention having the specified $R_2$ group, preferably a hydroxy group, in vicinal position to the sulfur substituent attached to the cyclohexyl ring, are found to be more stable after incubation with primary human hepatocytes in comparison with compounds missing such $R_2$ group.

For example after 4 hours incubation with human hepatocytes at a compound concentration of 5 µg/mL, for 14-O-{[(1S*,2S*,5R*)-5-((R)-2-Amino-3-methyl-butyrylamino)-2-hydroxy-cyclohexylsulfanyl]-acetyl}-mutilin hydrochloride and 14-O-{[(1R*,2R*,5S*)-5-((R)-2-Amino-3-methyl-butyrylamino)-2-hydroxy-cyclohexylsulfanyl]-acetyl}-mutilin hydrochloride—Example 11 of the present invention—91% and 90% of parent compounds were found, whereas for a mixture of 14-O-{[(1R,3R)-3-((R)-2-Amino-3-methyl-butyrylamino)-cyclohexylsulfanyl]-acetyl}-mutilin hydrochloride and the (1S,3S) diastereomer hydrochloride thereof—the analogous derivative wherein $R_2$, e.g. the hydroxyl group is missing—only 73% of parent compounds could be detected.

EXAMPLES

The trivial name "mutilin" refers to the IUPAC systematic name (1S,2R,3S,4S,6R,7R,8R,14R)-3,6-dihydroxy-2,4,7,14-tetramethyl-4-vinyl-tricyclo[5.4.3.0$^{1,8}$]tetradecan-9-one. In the examples, pleuromutilin derivatives are numbered in analogy to the mutilin numbering system described by H. Berner (Berner, H.; Schulz, G.; Schneider H. *Tetrahedron* 1980, 36, 1807-1811.):

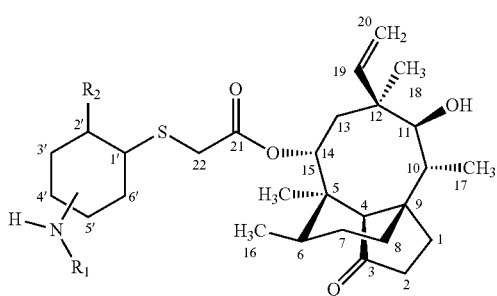

Pleuromutilin thiol and pleuromutlin tosylate are compounds of formulae:

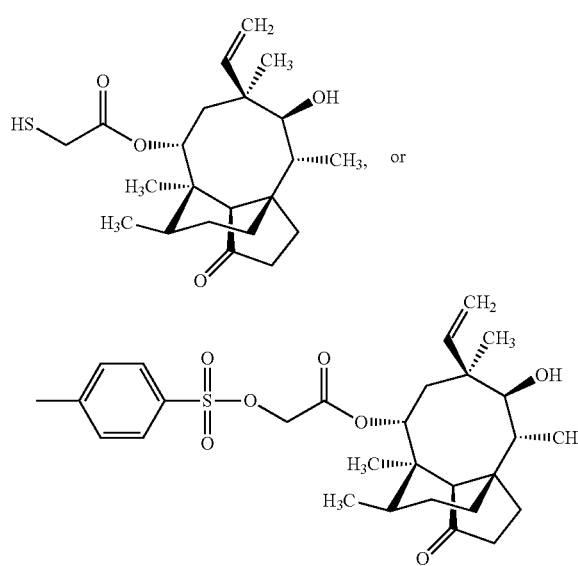

respectively

According, e.g. analogously, to a method as described in the following Examples 1 to 42 compounds of formula

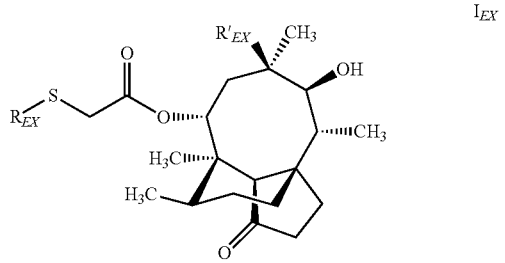

are obtained wherein $R_{EX}$ is as defined in the corresponding Examples.

In the compounds of Examples 1 to 12, 14 to 16, 18 and 20 to 42 R'$_{EX}$ is vinyl, in the compounds of Examples 13, 17 and 19 R'$_{EX}$ is ethyl.

Examples 1 to 3 are Reference Examples for the preparation of starting materials.

The following abbreviations are used:
° C. degree Celsius, uncorrected
% th percent of theory
Boc tert-butoxycarbonyl
CH$_2$Cl$_2$ dichloromethane
cHex cyclohexane
DBN 1,5-diazabicyclo[4.3.0]non-5-ene
DMF N,N-dimethylformamide
EDC N-(3-dimethylaminopropyl)-N'-ethylcarbodiimide hydrochloride
EtOAc ethyl acetate
h hour(s)
$^1$H proton
HOBT 1-hydroxybenzotriazole
M Molarity
MeOH methanol
min minute(s)
mol mole(s)
MS-ESI Electrospray ionization mass spectrometry
NH$_4$OH aqueous ammonium hydroxide solution (25-35% ammonia in aqueous solution)
NMR Nuclear magnetic resonance
mL milliliter
Na$_2$SO$_4$ sodium sulfate
R$_f$ retardation factor/retention factor of TLC
RT room temperature
TFA trifluoroacetic acid
THF tetrahydrofurane
TLC Thin Layer Chromatography

Example 1

14-O-{[(1R,2R,4R)-4-Amino-2-hydroxy-cyclohexyl-sulfanyl]-acetyl}-mutilin+(1S,2S,4S) diastereomer Diastereoisomeric Mixture of Compounds of Formula I$_{EX}$, Wherein R$_{EX}$ is a Group of Formula

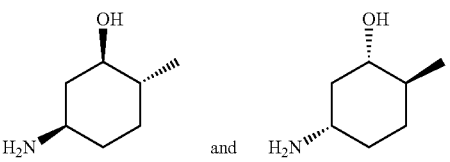

Step A1. 14-O-{[(1R,2R,4R)-4-tert-Butoxycarbonylamino-2-hydroxy-cyclohexylsulfanyl]-acetyl}-mutilin+(1S,2S,4S) diastereomer and 14-O-{[(1R,2R,5S)-5-tert-Butoxycarbonylamino-2-hydroxy-cyclohexylsulfanyl]-acetyl}-mutilin+(1S,2S,5R) diastereomer and 14-O-{[(1R,2R,4S)-4-tert-Butoxycarbonylamino-2-hydroxy-cyclohexylsulfanyl]-acetyl}-mutilin+(1S,2S,4R) diastereomer To a solution of 3,4-epoxycyclohexyl-carbamic acid tert-butyl ester (Gomez-Sanchez, E.; Marco-Contelles J. *Tetrahedron* 2005, 61, 1207-1219.) (4.27 g, 20 mmol) and pleuromutilin thiol (Nagarajan, R. Eli Lilly and Company 1978, U.S. Pat. No. 4,130,709) (7.10 g, 18 mmol) in 200 mL of THF is added aluminum oxide (40 g, Brockmann activity I, neutral) and the resulting mixture is stirred for 40 h at RT. The suspension is filtered and concentrated under reduced pressure. The residue is subjected to chromatography (silica, cHex/EtOAc=1/1) to give 14-O-{[(1R,2R,4R)-4-tert-butoxycarbonylamino-2-hydroxy-cyclohexylsulfanyl]-acetyl}-mutilin+(1S,2S,4S) diastereomer (a) ($R_f$=0.38; yield: 1.34 g, 12% th) as well as a mixture of 14-O-{[(1R,2R,5S)-5-tert-butoxycarbonylamino-2-hydroxy-cyclohexylsulfanyl]-acetyl}-mutilin+(1S,2S,5R) diastereomer and 14-O-{[(1R,2R,4S)-4-tert-butoxycarbonylamino-2-hydroxy-cyclohexylsulfanyl]-acetyl}-mutilin+(1S,2S,4R) diastereomer (b) ($R_f$=0.26; yield: 2.81 g, 25% th) as colorless solids.

(a): $^1$H NMR (400 MHz, DMSO-$d_6$, δ, ppm, inter alia): 6.74 (d, 1H, NH, J=7 Hz), 6.13 (dd, 1H, 19-H, J=11 Hz and 18 Hz), 5.54 (d, 1H, 14-H, J=8 Hz), 5.05 (m, 2H, 20-H), 4.90 (d, 1H, 2'-OH, J=5 Hz), 4.48 (d, 1H, 11-OH, J=6 Hz), 3.55-3.20 (m, 6H, 1'-H, 2'-H, 4'-H, 11-H, 22-H), 2.40 (bs, 1H, 4-H), 1.36 (s, 3H, 15-$CH_3$), 1.35 (s, 9H, tert-butyl), 1.06 (s, 3H, 18-$CH_3$), 0.81 (d, 3H, 17-$CH_3$, J=7 Hz), 0.62 (d, 3H, 16-$CH_3$, J=7 Hz). MS-ESI (m/z): 630 (MNa$^+$), 1237 (2MNa$^+$).

(b): $^1$H NMR (400 MHz, DMSO-$d_6$, δ, ppm, inter alia): 6.70 (d, 1H, NH, J=7 Hz), 6.12 (dd, 1H, 19-H, J=11 Hz and 18 Hz), 5.34 (d, 1H, 14-H, J=8 Hz), 5.05 (m, 2H, 20-H), 4.82, 4.78 (2d, 1H, 2'-OH, J=4 Hz), 4.48 (d, 1H, 11-OH, J=6 Hz), 3.55-3.20 (m, 5H, 2'-H, 4'/5'-H, 11-H, 22-H), 2.97 (m, 1H, 1'-H), 2.40 (bs, 1H, 4-H), 1.35 (s, 12H, 15-$CH_3$, tert-butyl), 1.05 (s, 3H, 18-$CH_3$), 0.82 (d, 3H, 17-$CH_3$, J=7 Hz), 0.62 (d, 3H, 16-$CH_3$, J=7 Hz). MS-ESI (m/z): 630 (MNa$^+$), 1237 (2MNa$^+$).

or Step A2. 14-O-{[(1R,2R,4R)-4-tert-Butoxycarbonylamino-2-hydroxy-cyclohexylsulfanyl]-acetyl}-mutilin+(1S,2S,4S) diastereomer and 14-O-{[(1R,2R,5S)-5-tert-Butoxycarbonylamino-2-hydroxy-cyclohexylsulfanyl]-acetyl}-mutilin+(1S,2S,5R) diastereomer and 14-O-{[(1R,2R,4S)-4-tert-Butoxycarbonylamino-2-hydroxy-cyclohexylsulfanyl]-acetyl}-mutilin+(1S,2S,4R) diastereomer To a solution of 3,4-epoxycyclohexyl-carbamic acid tert-butyl ester (10 g, 47 mmol) and pleuromutilin thiol (90%, 18.5 g, 42 mmol) in 150 mL of MeOH and 30 mL of dioxane is added 2M NaOH (21 mL, 42 mmol) and the resulting mixture is stirred for 16 h at RT. After completion of the reaction the pH is set to 7 with diluted HCl and the reaction mixture is concentrated under reduced pressure. The residue is diluted with water and brine and extracted three times with EtOAc. The organic layers are dried over $Na_2SO_4$ and filtered. The filtrate is concentrated under reduced pressure and after chromatography (silica, cHex/EtOAc=1/1) 14-O-{[(1R,2R,4R)-4-tert-butoxycarbonylamino-2-hydroxy-cyclohexylsulfanyl]-acetyl}-mutilin+(1S,2S,4S) diastereomer ($R_f$=0.40; yield: 3.1 g, 12% th) as well as a mixture of 14-O-{[(1R,2R,5S)-5-tert-butoxycarbonylamino-2-hydroxy-cyclohexylsulfanyl]acetyl}-mutilin+(1S,2S,5R) diastereomer and 14-O-{[(1R,2R,4S)-4-tert-butoxycarbonylamino-2-hydroxy-cyclohexylsulfanyl]-acetyl}-mutilin+(1S,2S,4R) diastereomer ($R_f$=0.25; yield: 6.35 g, 25% th) are obtained as colorless solids.

or Step A3. 14-O-{[(1R,2R,4R)-4-tert-Butoxycarbonylamino-2-hydroxy-cyclohexylsulfanyl]-acetyl}-mutilin+(1S,2S,4S) diastereomer and 14-O-{[(1R,2R,5S)-5-tert-Butoxycarbonylamino-2-hydroxy-cyclohexylsulfanyl]-acetyl}-mutilin+(1S,2S,5R) diastereomer To a solution of pleuromutilin thiol (9.25 g, 23.5 mmol) in 100 mL of $CH_3C$ (dried over 4 Å molecular sieve) is added DBN (2.9 µL, 23.5 mmol) and after 1 h of stirring at RT under argon atmosphere the mixture is charged with syn-3,4-epoxy-cyclohexyl-carbamic acid tert-butyl ester (4.17 g, 19.5 mmol) and stirred for further 16 h at RT. The reaction mixture is concentrated under reduced pressure. The residue is charged with brine and extracted with $CH_2Cl_2$. The organic layers are dried over $Na_2SO_4$ and filtered. The filtrate is concentrated under reduced pressure and subjected to chromatography (silica, cHex/EtOAc=1/1) to give 14-O-{[(1R,2R,4R)-4-tert-butoxycarbonylamino-2-hydroxy-cyclohexylsulfanyl]-acetyl}-mutilin+(1S,2S,4S) diastereomer ($R_f$=0.38; yield: 5.07 g, 43% th) as well as 14-O-{[(1R,2R,5S)-5-tert-butoxycarbonylamino-2-hydroxy-cyclohexylsulfanyl]-acetyl}-mutilin+(1S,2S,5R) diastereomer ($R_f$=0.25; yield: 2.95 g, 16.5% th) as colorless solids.

Step B. 14-O-{[(1R,2R,4R)-4-Amino-2-hydroxy-cyclohexylsulfanyl]-acetyl}-mutilin+(1S,2S,4S) diastereomer To a solution of 14-O-{[(1R,2R,4R)-4-tert-butoxycarbonylamino-2-hydroxy-cyclohexylsulfanyl]-acetyl}-mutilin+(1S,2S,4S) diastereomer (1.34 g, 2.20 mmol) in 75 mL of $CH_2Cl_2$ is added TFA (4 mL) and stirred for 5 h at RT. The reaction mixture is diluted with $CH_2Cl_2$ and poured into a saturated $NaHCO_3$ solution. The phases are separated and the aqueous layer is washed two times with $CH_2Cl_2$. The combined organic layers are dried over $Na_2SO_4$ and filtered. After chromatography (silica, EtOAc/MeOH/$NH_4OH$=50/50/1) 14-O-{[(1R,2R,4R)-4-amino-2-hydroxy-cyclohexylsulfanyl]-acetyl}-mutilin+(1S,2S,4S) diastereomer (yield: 745 mg, 67% th) is obtained as a colorless solid.

$^1$H NMR (400 MHz, DMSO-$d_6$, δ, ppm, inter alia): 6.14 (dd, 1H, 19-H, J=11 Hz and 18 Hz), 5.54 (d, 1H, 14-H, J=8 Hz), 5.05 (m, 2H, 20-H), 4.50 (d, 1H, 11-OH, J=6 Hz), 3.50-3.20 (m, 5H, 2'-H, 4'-H, 11-H, 22-H), 2.55 (m, 1H, 1'-H), 2.40 (bs, 1H, 4-H), 1.35 (s, 3H, 15-$CH_3$), 1.06 (s, 3H, 18-$CH_3$), 0.82 (d, 3H, 17-$CH_3$, J=7 Hz), 0.62 (d, 3H, 16-$CH_3$, J=7 Hz). MS-ESI (m/z): 508 (MH$^+$), 530 (MNa$^+$), 1015 (2 MH$^+$), 1037 (2MNa$^+$).

Example 2

14-O-{[(1R,2R,5S)-5-Amino-2-hydroxy-cyclohexylsulfanyl]-acetyl}-mutilin+(1S,2S,5R) diastereomer Diastereoisomeric Mixture of Compounds of Formula $I_{EX}$, Wherein $R_{EX}$ is a Group of Formula

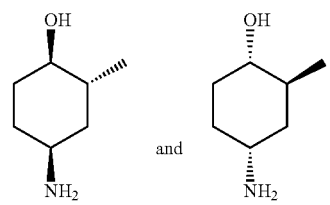

and

14-O-{[(1R,2R,4S)-4-Amino-2-hydroxy-cyclohexylsulfanyl]-acetyl}-mutilin+(1S,2S,4R) diastereomer Diastereoisomeric Mixture of Compounds of Formula $I_{EX}$, Wherein $R_{EX}$ is a Group of Formula

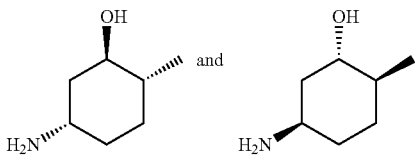

A mixture of 14-O-{[(1R,2R,5S)-5-tert-butoxycarbonylamino-2-hydroxy-cyclohexylsulfanyl]-acetyl}-mutilin+(1S,2S,5R) diastereomer and 14-O-{[(1R,2R,4S)-4-tert-butoxycarbonylamino-2-hydroxy-cyclohexylsulfanyl]-acetyl}-mutilin+(1S,2S,4R) diastereomer (1.12 g, 1.84 mmol) from Example 1 Step A is treated according to the method of Example 1 Step B. After work up and chromatography of the reaction mixture (silica, EtOAc/MeOH/NH$_4$OH=50/50/1) 14-O-{[(1R,2R,5S)-5-amino-2-hydroxy-cyclohexylsulfanyl]-acetyl}-mutilin+(1S,2S,5R) diastereomer (a) (R$_f$=0.33; yield: 524 mg, 56% th) and 14-O-{[(1R,2R,4S)-4-amino-2-hydroxy-cyclohexylsulfanyl]-acetyl}-mutilin+(1S,2S,4R) diastereomer (b) (R$_f$=0.22; yield: 160 mg, 17% th) are obtained as colorless solids.

(a): $^1$H NMR (400 MHz, DMSO-d$_6$, δ, ppm, inter alia): 6.13 (dd, 1H, 19-H, J=11 Hz and 18 Hz), 5.53 (d, 1H, 14-H, J=8 Hz), 5.05 (m, 2H, 20-H), 4.51 (d, 1H, 11-OH, J=6 Hz), 3.48 (m, 1H, 2'-H), 3.42 (m, 1H, 11-H), AB-system (v$_A$=3.37, v$_B$=3.23, 22-H, J=19 Hz), 2.98 (m, 1H, 1'-H), 2.82 (m, 1H, 5'-H), 2.40 (bs, 1H, 4-H), 1.36 (s, 3H, 15-CH$_3$), 1.06 (s, 3H, 18-CH$_3$), 0.82 (d, 3H, 17-CH$_3$, J=7 Hz), 0.63 (d, 3H, 16-CH$_3$, J=7 Hz).

(b): $^1$H NMR (400 MHz, DMSO-d$_6$, δ, ppm, inter alia): 6.14 (dd, 1H, 19-H, J=11 Hz and 18 Hz), 5.54 (d, 1H, 14-H, J=8 Hz), 5.06 (m, 2H, 20-H), 4.51 (bs, 1H, 11-OH), 3.79 (m, 1H, 2'-H), 3.42 (m, 1H, 11-H), AB-system (v$_A$=3.33, v$_B$=3.23, 22-H, J=15 Hz), 3.04 (m, 1H, 4'-H), 2.82 (m, 1H, 1'-H), 2.40 (bs, 1H, 4-H), 1.37 (s, 3H, 15-CH$_3$), 1.06 (s, 3H, 18-CH$_3$), 0.81 (d, 3H, 17-CH$_3$, J=7 Hz), 0.63 (d, 3H, 16-CH$_3$, J=7 Hz).

Example 3

14-O-{[(1R,2R,5R)-5-Amino-2-hydroxy-cyclohexylsulfanyl]-acetyl}-mutilin+(1S,2S,5S) diastereomer Diastereoisomeric Mixture of Compounds of Formula I$_{EX}$, Wherein R$_{EX}$ is a Group of Formula

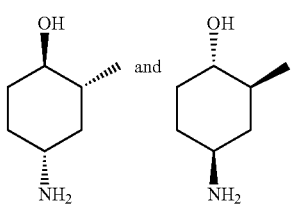

Step A. tert-Butyl-dimethyl-(cis-3,4-epoxycyclohexyloxy)-silane

To a solution of 3-cyclohexen-1-ol (Amburgey, J. C.; Shuey, S. W.; Pedersen, L. G.; Hiskey R., *Bioorganic Chemistry* 1994, 22, 172-197.) (10 g, 102 mmol) in CH$_2$Cl$_2$ is added vanadyl acetylacetonate (0.5 g, cat.) and tert-butyl hydroperoxide (20.4 mL 5.5M in decane, 112 mmol) and stirred overnight at RT. The resulting reaction mixture is treated with tert-butyldimethylsilyl chloride (16.9 g, 112 mmol), imidazole (9.02 g, 132 mmol) and 4-dimethylaminopyridine (2.49 g, 20 mmol) at 4° C. and stirred overnight at RT. The reaction mixture is diluted with CH$_2$Cl$_2$ and subsequently extracted with 10% NaHSO$_3$ solution, saturated NaHCO$_3$ solution and brine. The organic layer is dried over Na$_2$SO$_4$ and filtered. The filtrate is concentrated under reduced pressure and subjected to chromatography (silica, cHex/EtOAc=15/1) to yield tert-butyl-dimethyl-(cis-3,4-epoxycyclohexyloxy)-silane (R$_f$=0.35; yield: 18.3 g, 79% th) as a colorless oil.

$^1$H NMR (500 MHz, DMSO-d$_6$, δ, ppm): 3.55 (m, 1H), 3.00 (m, 2H), 2.15 (m, 1H), 2.00 (m, 1H), 1.80 (m, 1H), 1.50 (m, 1H), 1.35 (m, 1H), 1.35 (m, 1H), 1.25 (m, 1H), 0.83 (s, 9H, tert-butyl), 0.0 (s, 9H, Si(CH$_3$)$_2$).

Step B. 14-O-{[(1R,2R,5S)-5-(tert-Butyl-dimethylsilyloxy)-2-hydroxy-cyclohexylsulfanyl]-acetyl}-mutilin+(1S,2S,5R) diastereomer tert-Butyl-dimethyl-(cis-3,4-epoxycyclohexyloxy)-silane (6.41 g, 28 mmol) is treated with pleuromutilin thiol according to the method of Example 1 Step A2. Crude 14-O-{[(1R,2R,5S)-5-(tert-butyl-dimethyl-silyloxy)-2-hydroxy-cyclohexylsulfanyl]acetyl}-mutilin+(1S,2S,5R) diastereomer is obtained as a colorless solid which is used directly in the next step.

$^1$H NMR (400 MHz, DMSO-d$_6$, δ, ppm, inter alia): 6.13 (dd, 1H, 19-H, J=11 Hz and 18 Hz), 5.52 (d, 1H, 14-H, J=8 Hz), 5.05 (m, 2H, 20-H), 4.78 (dd, 1H, 2'-OH, J=5 Hz and 6 Hz), 4.48 (d, 1H, 11-OH, J=6 Hz), 3.88 (m, 1H, 5'-H), 3.15-3.45 (m, 4H, 2'-H, 11-H, 22-CH$_2$), 2.92 (m, 1H, 1'-H), 2.38 (bs, 1H, 4-H), 1.36 (s, 3H, 15-CH$_3$), 1.05 (s, 3H, 18-CH$_3$), 0.86 (s, 9H, tert-butyl), 0.81 (d, 3H, 17-CH$_3$, J=7 Hz), 0.63 (d, 3H, 16-CH$_3$, J=7 Hz), 0.0 (s, 6H, Si(CH$_3$)$_2$).

Step C. 14-O-{[(1R,2R,5S)-2,5-Dihydroxy-cyclohexylsulfanyl]-acetyl}-mutilin+(1S,2S,5R) diastereomer To a solution of 14-O-{[(1R,2R,5S)-5-(tert-butyl-dimethyl-silyloxy)-2-hydroxy-cyclohexylsulfanyl]acetyl}-mutilin+(1S,2S,5R) diastereomer (9.46 g, 15.2 mmol) in 25 mL of THF a mixture of acetic acid and water (3:1, 100 mL) is added and stirred for 2 days at 40° C. The reaction mixture is concentrated nearly to dryness under reduced pressure and the residue is dissolved in EtOAc and subjected to chromatography (silica, cHex/EtOAc=1/3) to give 14-O-{[(1R,2R,5S)-2,5-dihydroxy-cyclohexylsulfanyl]-acetyl}-mutilin+(1S,2S,5R) diastereomer (R$_f$=0.27; yield: 7.07 g, 92% th) as a colorless solid.

$^1$H NMR (400 MHz, DMSO-d$_6$, δ, ppm, inter alia): 6.12 (dd, 1H, 19-H, J=11 Hz and 18 Hz), 5.53 (d, 1H, 14-H, J=8 Hz), 5.05 (m, 2H, 20-H), 4.72 (dd, 1H, 2'-OH, J=2 Hz and 5 Hz), 4.48 (d, 1H, 11-OH, J=6 Hz), 4.43 (t, 1H, 5'-OH), 3.68 (m, 1H, 5'-H), 3.45-3.20 (m, 4H, 2'-H, 11-H, 22-H), 2.94 (m, 1H, 1'-H), 2.38 (bs, 1H, 4-H), 1.36 (s, 3H, 15-CH$_3$), 1.06 (s, 3H, 18-CH$_3$), 0.82 (d, 3H, 17-CH$_3$, J=7 Hz), 0.63 (d, 3H, 16-CH$_3$, J=7 Hz). MS-ESI (m/z): 531 (MNa$^+$), 1039 (2MNa$^+$).

Step D. 14-O-{[(1R,2R,5S)-2-Hydroxy-5-methanesulfonyloxy-cyclohexylsulfanyl]-acetyl}-mutilin+(1S,2S,5R) diastereomer To a solution of 14-O-{[(1R,2R,5S)-2,5-dihydroxy-cyclohexylsulfanyl]-acetyl}-mutilin+(1S,2S,5R) diastereomer (6.07 g, 11.9 mmol) in 36 mL of pyridine is added methanesulfonyl chloride (1.1 mL, 14.3 mmol) and the resulting mixture is stirred overnight at RT. Subsequently the solvent is evaporated under reduced pressure; the residue is diluted with 1M HCl and extracted three times with EtOAc. The combined organic layers are washed with brine, dried over $Na_2SO_4$ and filtered. The filtrate is concentrated and purified by column chromatography (silica, cHex/EtOAc=1/1) to give 14-O-{[(1R,2R,5S)-2-hydroxy-5-methanesulfonyloxy-cyclohexylsulfanyl]-acetyl}-mutilin+(1S,2S,5R) diastereomer ($R_f$=0.15; yield: 2.55 g, 36% th) as a colorless solid.

$^1$H NMR (400 MHz, DMSO-$d_6$, δ, ppm, inter alia): 6.12 (dd, 1H, 19-H, J=11 Hz and 18 Hz), 5.54 (d, 1H, 14-H, J=8 Hz), 5.07 (m, 2H, 20-H), 5.00 (t, 1H, 2'-OH, J=5 Hz), 4.78 (m, 1H, 5'-H), 4.50 (d, 1H, 11-OH, J=6 Hz), 3.55-3.25 (m, 4H, 2'-H, 11-H, 22-H), 2.91 (m, 1H, 1'-H), 2.38 (bs, 1H, 4-H), 1.36 (s, 3H, 15-$CH_3$), 1.05 (s, 3H, 18-$CH_3$), 0.80 (d, 3H, 17-$CH_3$, J=7 Hz), 0.63 (d, 3H, 16-$CH_3$, J=7 Hz).

Step E. 14-O-{[(1R,2R,5R)-5-Azido-2-hydroxy-5-methanesulfonyloxy-cyclohexylsulfanyl]-acetyl}-mutilin+(1S,2S,5S) diastereomer A solution of 14-O-{[(1R,2R,5S)-2-hydroxy-5-methanesulfonyloxy-cyclohexylsulfanyl]-acetyl}-mutilin+(1S,2S,5R) diastereomer (2.55 g, 4.35 mmol) and sodium azide (0.85 g, 13 mmol) in 30 mL of DMF is heated at 80° C. for 6 h. The reaction mixture is diluted with water and brine and extracted three times with EtOAc. The combined organic layers are washed with water and brine, dried over $Na_2SO_4$ and filtered. The solvent is removed under reduced pressure and crude 14-O-{[(1R,2R,5R)-5-azido-2-hydroxy-cyclohexylsulfanyl]-acetyl}-mutilin+(1S,2S,5S) diastereomer (quantitative yield, cHex/EtOAc=1/1, $R_f$=0.35) is obtained as a solid which is used directly in the next step.

$^1$H NMR (400 MHz, DMSO-$d_6$, δ, ppm, inter alia): 6.15, 6.13 (2 dd, 1H, 19-H, J=11 Hz and 18 Hz), 5.56, 5.54 (2d, 1H, 14-H, J=8 Hz), 5.05 (m, 2H, 20-H), 4.90 (d, 1H, 2'-OH, J=5 Hz), 4.50, 4.49 (2d, 1H, 11-OH, J=6 Hz), 3.50-3.25 (m, 5H, 2'-H, 5'-H, 11-H, 22-H), 2.64 (m, 1H, 1'-H), 2.40 (bs, 1H, 4-H), 1.36 (s, 3H, 15-$CH_3$), 1.06 (s, 3H, 18-$CH_3$), 0.81 (d, 3H, 17-$CH_3$, J=7 Hz), 0.63 (d, 3H, 16-$CH_3$, J=7 Hz).

Step F. 14-O-{[(1R,2R,5R)-5-Amino-2-hydroxy-cyclohexylsulfanyl]-acetyl}-mutilin+(1S,2S,5S) diastereomer Triphenylphosphine (1.18 g, 4.50 mmol) is added to a solution of 14-O-{[(1R,2R,5R)-5-azido-2-hydroxy-cyclohexylsulfanyl]-acetyl}-mutilin+(1S,2S,5S) diastereomer (2.4 g, uncorrected) in 30 mL of THF and stirred overnight at RT. Subsequently water (approx. 3 mL) is added and the reaction mixture is heated at reflux for 1 h. After evaporation of the solvent the residue is diluted with water and brine and extracted three times with EtOAc. The combined organic layers are dried over $Na_2SO_4$, filtered and subjected to chromatography (silica, EtOAc/MeOH/$NH_4OH$=100/100/1) to give 14-O-{[(1R,2R,5R)-5-amino-2-hydroxy-cyclohexylsulfanyl]-acetyl}-mutilin+(1S,2S,5S) diastereomer ($R_f$=0.3; yield: 1.74 g, 79% th) as a colorless solid.

$^1$H NMR (400 MHz, DMSO-$d_6$, δ, ppm, inter alia): 7.25, 6.65 (2 bs, 1H, NH), 6.14 (dd, 1H, 19-H, J=11 Hz and 18 Hz), 5.54 (d, 1H, 14-H, J=8 Hz), 5.04 (m, 2H, 20-H), 4.50 (bs, 1H, 11-OH), 3.55-3.10 (m, 5H, 2'-H, 5'-H, 11-H, 22-H), 2.58 (m, 1H, 1'-H), 2.40 (bs, 1H, 4-H), 1.36 (s, 3H, 15-$CH_3$), 1.05 (s, 3H, 18-$CH_3$), 0.81 (d, 3H, 17-$CH_3$, J=7 Hz), 0.62 (d, 3H, 16-$CH_3$, J=7 Hz). MS-ESI (m/z): 508 ($MH^+$), 530 ($MNa^+$), 1037 ($2MNa^+$).

Example 4

14-O-{[(1S*,2S*,4S*)-4-((R)-2-Amino-3-methyl-butyrylamino)-2-hydroxy-cyclohexylsulfanyl]-acetyl}-mutilin hydrochloride and 14-O-{[(1R*,2R*,4R*)-4-((R)-2-Amino-3-methyl-butyrylamino)-2-hydroxy-cyclohexylsulfanyl]-acetyl}-mutilin hydrochloride Compounds of Formula $I_{EX}$, Wherein $R_{EX}$ is a Group of Formula

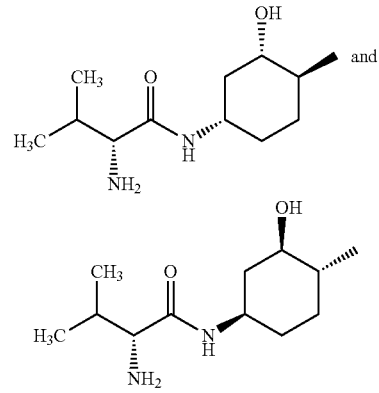

Step A. 14-O-{[(1S,2S,4S)-4-((R)-2-tert-Butoxycarbonylamino-3-methyl-butyrylamino)-2-hydroxy-cyclohexylsulfanyl]-acetyl}-mutilin+(1R,2R,4R) diastereomer To a solution of (R)-2-tert-butoxycarbonylamino-3-methyl-butyric acid (Boc-D-valine, 385 mg, 1.77 mmol) in 15 mL of $CH_2Cl_2$ is added HOBT (266 mg, 1.97 mmol) and EDC (378 mg, 1.97 mmol) and stirred for 30 min at RT. Then 14-O-{[(1R,2R,4R)-4-amino-2-hydroxy-cyclohexylsulfanyl]-acetyl}-mutilin+(1S,2S,4S) diastereomer (1 g, 1.97 mmol) from Example 1 Step B is added and the resulting mixture is stirred at RT until completion of the reaction (typically overnight). The reaction mixture is charged with brine and extracted with EtOAc. The organic layers are dried over $Na_2SO_4$ and filtered. The filtrate is concentrated under reduced pressure and subjected to chromatography (silica, cHex/EtOAc=1/3) yielding 14-O-{[(1S,2S,4S)-4-((R)-2-tert-butoxycarbonylamino-3-methyl-butyrylamino)-2-hydroxy-cyclohexylsulfanyl]-acetyl}-mutilin+(1R,2R,4R) diastereomer ($R_f$=0.6; yield: 1.11 g, 89% th) as a colorless solid.

$^1$H NMR (400 MHz, DMSO-$d_6$, δ, ppm, inter alia): 7.73 (m, 1H, NHCO), 6.50 (m, 1H, NHCO), 6.14 (dd, J=11 Hz and 17 Hz), 5.55 (d, 1H, 14-H, J=8 Hz), 5.10-4.90 (m, 3H, 20-H, 2'-OH), 4.48 (d, 1H, 11-OH, J=6 Hz), 3.67 (t, 1H, Val-CHNH, J=8 Hz), 3.62-3.25 (m, 5H, 4'-H, 11-H, 22-H, 2'-H), 2.53 (m, 1H, 1'-H), 2.40 (bs, 1H, 4-H), 1.36 (bs, 12H, tert-butyl, 15-$CH_3$), 1.05 (s, 3H, 18-$CH_3$), 0.85-0.75 (m, 9H, 17-$CH_3$, 2× Val-$CH_3$), 0.63 (d, 3H, 16-$CH_3$, J=6 Hz). MS-ESI (m/z): 707 ($MH^+$), 729 ($MNa^+$).

Step B. 14-O-{[(1S*,2S*,4S*)-4-((R)-2-Amino-3-methyl-butyrylamino)-2-hydroxy-cyclohexylsulfanyl]-acetyl}-mutilin and 14-O-{[(1R*,2R*,4R*)-4-((R)-2-Amino-3-methyl-butyrylamino)-2-hydroxy-cyclohexylsulfanyl]-acetyl}-mutilin To a solution of 14-O-{[(1S,2S,4S)-4-((R)-2-tert-butoxycarbonylamino-3-methyl-butyrylamino)-2-hydroxy-cyclohexylsulfanyl]acetyl}-mutilin+(1R,2R,4R) diastereomer (1.11 g, 1.57 mmol) in 10 mL of CH$_2$Cl$_2$ is added TFA (1.57 mL) and stirred for 5 h at RT. The reaction mixture is diluted with CH$_2$Cl$_2$ and poured into a saturated NaHCO$_3$ solution. The phases are separated and the aqueous layer is washed with CH$_2$Cl$_2$. The combined organic layers are dried over Na$_2$SO$_4$ and filtered. After chromatography (silica, EtOAc/MeOH/NH$_4$OH=90/9/1) 14-O-{[(1S*,2S*,4S*)-4-((R)-2-amino-3-methyl-butyrylamino)-2-hydroxy-cyclohexylsulfanyl]acetyl}-mutilin (a) (silica, EtOAc/MeOH/NH$_4$OH=50/50/1, R$_f$=0.3; 356 mg, 37% yield) and 14-O-{[(1R*,2R*,4R*)-4-((R)-2-amino-3-methyl-butyrylamino)-2-hydroxy-cyclohexylsulfanyl]-acetyl}-mutilin (b) (silica, EtOAc/MeOH/NH$_4$OH=50/50/1, R$_f$=0.25; yield: 136 mg, 14% th) are obtained as colorless solids.

(a): $^1$H NMR (500 MHz, DMSO-d$_6$, δ, ppm, inter alia): 7.70 (d, 1H, NHCO, J=8 Hz), 6.13 (dd, 1H, 19-H, J=11 Hz and 18 Hz), 5.54 (d, 1H, 14-H, J=8 Hz), 5.05 (m, 2H, 20-H) 4.96 (d, 1H, 2'-OH, J=5 Hz), 4.50 (d, 1H, 11-OH, J=6 Hz), 3.58 (m, 1H, 4'-H), 3.53-3.25 (m, 4H, 11-H, 22-H, 2'-H), 2.82 (d, 1H, Val-CHNH, J=5 Hz), 2.54 (m, 1H, 1'-H), 2.40 (bs, 1H, 4-H), 1.36 (s, 3H, 15-CH$_3$), 1.05 (s, 3H, 18-CH$_3$), 0.84-0.79 (m, 6H, 17-CH$_3$, Val-CH$_3$), 0.75 (d, 3H, Val-CH$_3$, J=7 Hz), 0.62 (d, 3H, 16-CH$_3$, J=7 Hz). MS-ESI (m/z): 607 (MH$^+$), 629 (MNa$^+$), 641 (MCl$^-$).

(b): $^1$H NMR (500 MHz, DMSO-d$_6$, δ, ppm, inter alia): 7.68 (d, 1H, NHCO, J=8 Hz), 6.13 (dd, 1H, 19-H, J=11 Hz and 18 Hz), 5.55 (d, 1H, 14-H, J=8 Hz), 5.05 (m, 2H, 20-H) 4.96 (d, 1H, 2'-OH, J=5 Hz), 4.50 (d, 1H, 11-OH, J=6 Hz), 3.58 (m, 1H, 4'-H), 3.48-3.25 (m, 4H, 11-H, 22-H, 2'-H), 2.83 (d, 1H, Val-CHNH, J=5 Hz), 2.52 (m, 1H, 1'-H), 2.40 (bs, 1H, 4-H), 1.35 (s, 3H, 15-CH$_3$), 1.05 (s, 3H, 18-CH$_3$), 0.84-0.79 (m, 6H, 17-CH$_3$, Val-CH$_3$), 0.75 (d, 3H, Val-CH$_3$, J=7 Hz), 0.62 (d, 3H, 16-CH$_3$, J=7 Hz). MS-ESI (m/z): 607 (MH$^+$), 629 (MNa$^+$), 641 (MCl$^-$).

Step C. 14-O-{[(1S*,2S*,4S*)-4-((R)-2-Amino-3-methyl-butyrylamino)-2-hydroxy-cyclohexylsulfanyl]acetyl}-mutilin hydrochloride and 14-O-{[(1R*,2R*,4R*)-4-((R)-2-Amino-3-methyl-butyrylamino)-2-hydroxy-cyclohexylsulfanyl]-acetyl}-mutilin hydrochloride A solution of 14-O-{[(1S*,2S*,4S*)-4-((R)-2-amino-3-methyl-butyrylamino)-2-hydroxy-cyclohexylsulfanyl]-acetyl}-mutilin (356 mg, 0.59 mmol) in 3 mL of dioxane is treated with 1M HCl (0.9 mL) and water (0.5 mL). After stirring at RT for 10 min the solution is lyophilized to obtain 14-O-{[(1S*,2S*,4S*)-4-((R)-2-amino-3-methyl-butyrylamino)-2-hydroxy-cyclohexylsulfanyl]acetyl}-mutilin hydrochloride (a) (yield: 300 mg, 79% th) as a colorless solid.

14-O-{[(1R*,2R*,4R*)-4-((R)-2-Amino-3-methyl-butyrylamino)-2-hydroxy-cyclohexylsulfanyl]-acetyl}-mutilin (136 mg, 0.22 mmol) is treated analogously to the other diastereomer described above to obtain 14-O-{[(1R*,2R*,4R*)-4-((R)-2-amino-3-methyl-butyrylamino)-2-hydroxy-cyclohexylsulfanyl]acetyl}-mutilin hydrochloride (b) (yield: 120 mg, 85% th) as a colorless solid.

(a): $^1$H NMR (500 MHz, DMSO-d$_6$, δ, ppm, inter alia): 8.10 (d, 1H, NHCO, J=8 Hz), 6.13 (dd, 1H, 19-H, J=11 Hz and 18 Hz), 5.95 (bs, 3H, NH$_3{}^+$), 5.54 (d, 1H, 14-H, J=8 Hz), 5.05 (m, 2H, 20-H), 4.99 (d, 1H, 2'-OH, J=5 Hz), 4.52 (d, 1H, 11-OH, J=6 Hz), 3.61 (m, 1H, 4'-H), 3.53-3.25 (m, 4H, 11-H, 22-H, 2'-H), 3.17 (d, 1H, Val-CHNH, J=6 Hz), 2.53 (m, 1H, 1'-H), 2.40 (bs, 1H, 4-H), 1.36 (s, 3H, 15-CH$_3$), 1.04 (s, 3H, 18-CH$_3$), 0.90-0.78 (3d, 9H, 17-CH$_3$, 2× Val-CH$_3$, J=7 Hz), 0.62 (d, 3H, 16-CH$_3$, J=7 Hz). MS-ESI (m/z): 607 (M$^+$), 629 (MNa$^+$), 641 (MCl$^-$).

(b): $^1$H NMR (500 MHz, DMSO-d$_6$, δ, ppm, inter alia): 8.01 (d, 1H, NHCO, J=8 Hz), 6.13 (dd, 1H, 19-H, J=11 Hz and 18 Hz), 5.54 (d, 1H, 14-H, J=8 Hz), 5.45 (bs, 3H, NH$_3{}^+$), 5.04 (m, 2H, 20-H), 5.00 (d, 1H, 2'-OH, J=5 Hz), 4.51 (d, 1H, 11-OH, J=6 Hz), 3.60 (m, 1H, 4'-H), 3.51-3.25 (m, 4H, 11-H, 22-H, 2'-H), 3.12 (d, 1H, Val-CHNH, J=6 Hz), 2.51 (m, 1H, 1'-H), 2.40 (bs, 1H, 4-H), 1.36 (s, 3H, 15-CH$_3$), 1.04 (s, 3H, 18-CH$_3$), 0.88-0.78 (3d, 9H, 17-CH$_3$, 2× Val-CH$_3$), 0.62 (d, 3H, 16-CH$_3$, J=7 Hz). MS-ESI (m/z): 607 (M$^+$), 629 (MNa$^+$), 641 (MCl$^-$).

Example 5

14-O-{[(1S*,2S*,4S*)-4-((S)-2-Amino-3-methyl-butyrylamino)-2-hydroxy cyclohexylsulfanyl]-acetyl}-mutilin hydrochloride and 14-O-{[(1R*,2R*,4R*)-4-((S)-2-Amino-3-methyl-butyrylamino)-2-hydroxy-cyclohexylsulfanyl]-acetyl}-mutilin hydrochloride Compounds of Formula I$_{EX}$, Wherein R$_{EX}$ is a Group of Formula

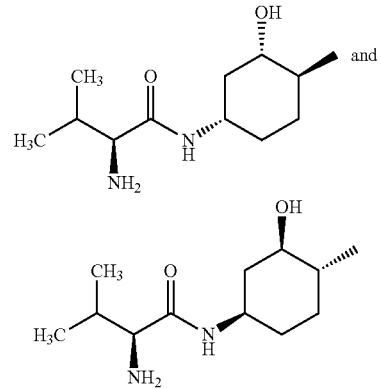

14-O-{[(1R,2R,4R)-4-Amino-2-hydroxy-cyclohexylsulfanyl]-acetyl}-mutilin+(1S,2S,4S) diastereomer (1.5 g, 2.95 mmol) from Example 1 Step B is treated with (S)-2-tert-butoxycarbonylamino-3-methyl-butyric acid (Boc-L-valine, 577 mg, 2.66 mmol) according to the method of Example 4 Step A to C to give 14-O-{[(1S*,2S*,4S*)-4-((S)-2-amino-3-methyl-butyrylamino)-2-hydroxy-cyclohexylsulfanyl] acetyl}-mutilin hydrochloride (a) (yield: 458 mg) and 14-O-{[(1R*,2R*,4R*)-4-((S)-2-amino-3-methyl-butyrylamino)-2-hydroxy-cyclohexylsulfanyl]acetyl}-mutilin hydrochloride (b) (yield: 386 mg) as colorless solids.

(a $^1$H NMR (500 MHz, DMSO-d$_6$, δ, ppm, inter alia): 8.35 (d, 1H, NHCO, J=8 Hz), 8.07 (bs, 3H, NH$_3{}^+$), 6.14 (dd, 1H, 19-H, J=11 Hz and 18 Hz), 5.55 (d, 1H, 14-H, J=8 Hz), 5.05 (m, 2H, 20-H), 4.99 (d, 1H, 2'-OH, J=5 Hz), 4.50 (d, 1H, 11-OH, J=6 Hz), 3.64 (m, 1H, 4'-H), 3.50-3.25 (m, 5H, 22-H, 11-H, Val-CHNH, 2'-H), 2.52 (m, 1H, 1'-H), 2.40 (bs, 1H, 4-H), 1.35 (s, 3H, 15-CH$_3$), 1.05 (s, 3H, 18-CH$_3$), 0.93-0.87 (2d, 6H, 2× Val-CH$_3$, J=7 Hz), 0.81 (d, 3H, 17-CH$_3$, J=7 Hz), 0.63 (d, 3H, 16-CH$_3$, J=7 Hz). MS-ESI (m/z): 607 (M$^+$).

(b $^1$H NMR (500 MHz, DMSO-d$_6$, δ, ppm, inter alia): 8.35 (d, 1H, NHCO, J=8 Hz), 8.08 (bs, 3H, NH$_3{}^+$), 6.14 (dd, 1H, 19-H, J=11 Hz and 18 Hz), 5.55 (d, 1H, 14-H, J=8 Hz), 5.10-5.00 (m, 3H, 20-H, 2'-OH), 4.51 (d, 1H, 11-OH, J=6

Hz), 3.64 (m, 1H, 4'-H), 3.52 (d, 1H, 22 a-H, J=15 Hz), 3.45-3.25 (m, 4H, 11-H, Val-CHNH, 2'-H, 22 b-H), 2.53 (m, 1H, 1'-H), 2.40 (bs, 1H, 4-H), 1.36 (s, 3H, 15-CH$_3$), 1.05 (s, 3H, 18-CH$_3$), 0.93-0.87 (2d, 6H, 2× Val-CH$_3$, J=7 Hz), 0.81 (d, 3H, 17-CH$_3$, J=7 Hz), 0.62 (d, 3H, 16-CH$_3$, J=7 Hz). MS-ESI (m/z): 607 (M$^+$).

Example 6

14-O-{[(1S*,2S*,4S*)-4-((R)-2-Amino-propionylamino)-2-hydroxy-cyclohexylsulfanyl]-acetyl}-mutilin hydrochloride and 14-O-{[(1R*,2R*,4R*)-4-((R)-2-Amino-propionylamino)-2-hydroxy-cyclohexylsulfanyl]-acetyl}-mutilin hydrochloride Compounds of Formula $I_{EX}$, Wherein $R_{EX}$ is a Group of Formula

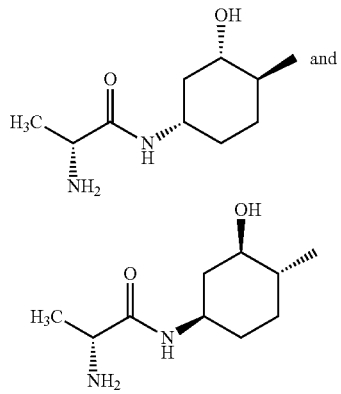

14-O-{[(1R,2R,4R)-4-Amino-2-hydroxy-cyclohexylsulfanyl]-acetyl}-mutilin+(1S,2S,4S) diastereomer (1 g, 1.97 mmol) from Example 1 Step B is treated with (R)-2-tert-butoxycarbonylamino-propionic acid (Boc-D-alanine, 335 mg, 1.77 mmol) according to the method of Example 4 Step A to C to give 14-O-{[(1S*,2S*,4S*)-4-((R)-2-amino-propionylamino)-2-hydroxy-cyclohexylsulfanyl]-acetyl}-mutilin hydrochloride (a) (yield: 200 mg) and 14-O-{[(1R*,2R*,4R*)-4-((R)-2-amino-propionylamino)-2-hydroxy-cyclohexylsulfanyl]acetyl}-mutilin hydrochloride (b) (yield: 222 mg) as colorless solids.

(a): $^1$H NMR (500 MHz, DMSO-d$_6$, δ, ppm, inter alia): 7.92 (d, 1H, NHCO, J=7 Hz), 6.13 (dd, 1H, 19-H, J=11 Hz and 18 Hz), 5.54 (d, 1H, 14-H, J=8 Hz), 5.05 (m, 2H, 20-H), 4.99 (bs, 1H, 2'-OH), 4.51 (d, 1H, 11-OH, J=6 Hz), 3.57 (m, 1H, 4'-H), 3.53-3.25 (m, 5H, 11-H, 22-H, Ala-CHNH, 2'-H), 2.53 (m, 1H, 1'-H), 2.40 (bs, 1H, 4-H), 1.36 (s, 3H, 15-CH$_3$), 1.15 (d, 3H, Ala-CH$_3$, J=7 Hz), 1.05 (s, 3H, 18-CH$_3$), 0.81 (d, 3H, 17-CH$_3$, J=7 Hz), 0.62 (d, 3H, 16-CH$_3$, J=7 Hz). MS-ESI (m/z): 579 (M$^+$), 601 (MNa$^+$), 613 (MCl$^-$).

(b): $^1$H NMR (500 MHz, DMSO-d$_6$, δ, ppm, inter alia): 7.96 (d, 1H, NHCO, J=8 Hz), 6.14 (dd, 1H, 19-H, J=11 Hz and 18 Hz), 5.55 (d, 1H, 14-H, J=8 Hz), 5.40 (bs, 3H, NH$_3^+$), 5.04 (m, 2H, 20-H), 4.99 (d, 1H, 2'-OH, J=5 Hz), 4.50 (d, 1H, 11-OH, J=6 Hz), 3.57 (m, 1H, 4'-H), 3.48-3.25 (m, 5H, 11-H, 22-H, Ala-CHNH, 2'-H), 2.52 (m, 1H, 1'-H), 2.40 (bs, 1H, 4-H), 1.35 (s, 3H, 15-CH$_3$), 1.17 (d, 3H, Ala-CH$_3$, J=7 Hz), 1.05 (s, 3H, 18-CH$_3$), 0.81 (d, 3H, 17-CH$_3$, J=7 Hz), 0.62 (d, 3H, 16-CH$_3$, J=7 Hz). MS-ESI (m/z): 579 (M$^+$), 601 (MNa$^+$), 613 (MCl$^-$).

Example 7

14-O-{[(1S*,2S*,4S*)-4-((S)-2-Amino-propionylamino)-2-hydroxy-cyclohexylsulfanyl]acetyl}-mutilin hydrochloride and 14-O-{[(1R*,2R*,4R*)-4-((R)-2-Amino-propionylamino)-2-hydroxy-cyclohexylsulfanyl]-acetyl}-mutilin hydrochloride Compounds of Formula $I_{EX}$, Wherein $R_{EX}$ is a Group of Formula

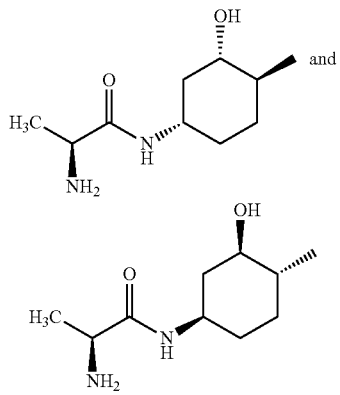

14-O-{[(1R,2R,4R)-4-Amino-2-hydroxy-cyclohexylsulfanyl]-acetyl}-mutilin+(1S,2S,4S) diastereomer (1.5 g, 2.95 mmol) from Example 1 Step B is treated with (S)-2-tert-butoxycarbonylamino-propionic acid (Boc-L-alanine, 502 mg, 2.66 mmol) according to the method of Example 4 Step A to C to give 14-O-{[(1S*,2S*,4S*)-4-((S)-2-amino-propionylamino)-2-hydroxy-cyclohexylsulfanyl]-acetyl}-mutilin hydrochloride (a) (yield: 556 mg) and 14-O-{[(1R*,2R*,4R*)-4-((S)-2-amino-propionylamino)-2-hydroxy-cyclohexylsulfanyl]acetyl}-mutilin hydrochloride (b) (yield: 730 mg) as colorless solids.

(a): $^1$H NMR (500 MHz, DMSO-d$_6$, δ, ppm, inter alia): 8.34 (d, 1H, NHCO, J=8 Hz), 8.13 (bs, 3H, NH$_3^+$), 6.14 (dd, 1H, 19-H, J=11 Hz and 18 Hz), 5.55 (d, 1H, 14-H, J=8 Hz), 5.05 (m, 2H, 20-H), 3.71 (m, 1H, Ala-CHNH), 3.58 (m, 1H, 4'-H), 3.46 (d, 1H, 22 a-H, J=15 Hz), 3.42 (d, 1H, 11-H, J=6 Hz), 3.35-3.25 (m, 2H, 22 b-H, 2'-H), 2.52 (m, 1H, 1'-H), 2.40 (bs, 1H, 4-H), 1.35 (s, 3H, 15-CH$_3$), 1.31 (d, 3H, Ala-CH$_3$, J=7 Hz), 1.05 (s, 3H, 18-CH$_3$), 0.81 (d, 3H, 17-CH$_3$, J=7 Hz), 0.62 (d, 3H, 16-CH$_3$, J=7 Hz). MS-ESI (m/z): 579 (M$^+$).

(b): $^1$H NMR (500 MHz, DMSO-d$_6$, δ, ppm, inter alia): 8.30 (d, 1H, NHCO, J=8 Hz), 8.08 (bs, 3H, NH$_3^+$), 6.14 (dd, 1H, 19-H, J=11 Hz and 18 Hz), 5.54 (d, 1H, 14-H, J=8 Hz), 5.06 (m, 2H, 20-H), 5.01 (d, 1H, 2'-OH, J=5 Hz), 4.51 (d, 1H, 11-OH, J=6 Hz), 3.71 (m, 1H, Ala-CHNH), 3.59 (m, 1H, 4'-H), 3.52 (d, 1H, 22 a-H, J=15 Hz), 3.42 (t, 1H, 11-H, J=6 Hz), 3.36-3.25 (m, 2H, 22 b-H, 2'-H), 2.53 (m, 1H, 1'-H), 2.40 (bs, 1H, 4-H), 1.36 (s, 3H, 15-CH$_3$), 1.30 (d, 3H, Ala-CH$_3$, J=7 Hz), 1.05 (s, 3H, 18-CH$_3$), 0.81 (d, 3H, 17-CH$_3$, J=7 Hz), 0.62 (d, 3H, 16-CH$_3$, J=7 Hz). MS-ESI (m/z): 579 (M$^+$).

Example 8

14-O-{[(1S*,2S,4S*)-2-Hydroxy-4-[((R)-piperidine-2-carbonyl)-amino]-cyclohexylsulfanyl-acetyl}-mutilin hydrochloride and 14-O-{[(1R*,2R*,4R*)-2-Hydroxy-4-[((R)-piperidine-2-carbonyl)-amino]-cyclohexylsulfanyl]-acetyl}-mutilin hydrochloride Compounds of Formula $I_{EX}$, Wherein $R_{EX}$ is a Group of Formula

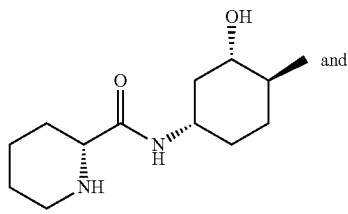

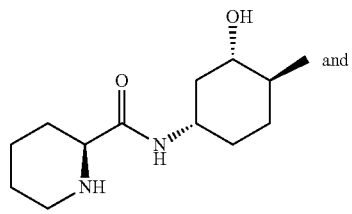

14-O-{[(1R,2R,4R)-4-Amino-2-hydroxy-cyclohexylsulfanyl]-acetyl}-mutilin+(1S,2S,4S) diastereomer (1 g, 1.97 mmol) from Example 1 Step B is treated with (R)-1-(tert-butoxycarbonyl)-2-piperidinecarboxylic acid (Boc-D-pipecolinic acid, Boc-D-homoproline, 407 mg, 1.77 mmol) according to the method of Example 4 Step A to C to give 14-O-{[(1S*,2S*,4S*)-2-hydroxy-4-[((R)-piperidine-2-carbonyl)-amino]-cyclohexylsulfanyl]-acetyl}-mutilin hydrochloride (a) (yield: 280 mg) and 14-O-{[(1R*,2R*,4R*)-2-hydroxy-4-[((R)-piperidine-2-carbonyl)-amino]-cyclohexylsulfanyl]-acetyl}-mutilin hydrochloride (b) (yield: 290 mg) as colorless solids.

(a): $^1$H NMR (400 MHz, DMSO-$d_6$, δ, ppm, inter alia): 8.28 (d, 1H, NHCO, J=8 Hz), 6.14 (dd, 1H, 19-H, J=11 Hz and 18 Hz), 5.54 (d, 1H, 14-H, J=8 Hz), 5.05 (m, 2H, 20-H), 5.00 (d, 1H, 2'-OH, J=5 Hz), 4.51 (d, 1H, 11-OH, J=6 Hz), 3.60 (m, 1H, 4'-H), 3.57-3.25 (m, 5H, Pip-CHNH, 22-H, 11-H, 2'-H), 3.13, 2.80 (2 m, 2H, Pip-H), 2.53 (m, 1H, 1'-H), 2.40 (bs, 1H, 4-H), 1.36 (s, 3H, 15-$CH_3$), 1.05 (s, 3H, 18-$CH_3$), 0.81 (d, 3H, 17-$CH_3$, J=7 Hz), 0.62 (d, 3H, 16-$CH_3$, J=7 Hz). MS-ESI (m/z): 619 ($M^+$), 653 ($MCl^-$).

(b): $^1$H NMR (400 MHz, DMSO-$d_6$, δ, ppm, inter alia): 8.04 (d, 1H, NHCO, J=8 Hz), 6.14 (dd, 1H, 19-H, J=11 Hz and 18 Hz), 5.55 (d, 1H, 14-H, J=8 Hz), 5.10-4.95 (m, 3H, 20-H, 2'-OH), 4.50 (d, 1H, 11-OH, J=6 Hz), 3.58 (m, 1H, 4'-H), 3.50-3.20 (m, 5H, Pip-CHNH, 22-H, 11-H, 2'-H), 3.15, 2.70 (2 m, 2H, Pip-H), 2.53 (m, 1H, 1'-H), 2.40 (bs, 1H, 4-H), 1.36 (s, 3H, 15-$CH_3$), 1.05 (s, 3H, 18-$CH_3$), 0.81 (d, 3H, 17-$CH_3$, J=7 Hz), 0.62 (d, 3H, 16-$CH_3$, J=7 Hz). MS-ESI (m/z): 619 ($M^+$), 653 ($MCl^-$).

Example 9

14-O-{[(1S*,2S*,4S*)-2-Hydroxy-4-[((S)-piperidine-2-carbonyl)-amino]-cyclohexylsulfanyl]-acetyl}-mutilin hydrochloride and 14-O-{[(1R*,2R*,4R*)-2-Hydroxy-4-[((S)-piperidine-2-carbonyl)-amino]-cyclohexylsulfanyl]-acetyl}-mutilin hydrochloride.

Compounds of Formula $I_{EX}$, Wherein $R_{EX}$ is a Group of Formula

14-O-{[(1R,2R,4R)-4-Amino-2-hydroxy-cyclohexylsulfanyl]-acetyl}-mutilin+(1S,2S,4S) diastereomer (1.5 g, 2.95 mmol) from Example 1 Step B is treated with (S)-1-(tert-butoxycarbonyl)-2-piperidinecarboxylic acid (Boc-L-pipecolinic acid, Boc-L-homoproline, 609 mg, 2.66 mmol) according to the method of Example 4 Step A to C to give 14-O-{[(1S*,2S*,4S*)-2-hydroxy-4-[((S)-piperidine-2-carbonyl)-amino]-cyclohexylsulfanyl]-acetyl}-mutilin hydrochloride (a) (yield: 397 mg) and 14-O-{[(1R*,2R*,4R*)-2-hydroxy-4-[((S)-piperidine-2-carbonyl)-amino]-cyclohexylsulfanyl]-acetyl}-mutilin hydrochloride (b) (yield: 238 mg) as colorless solids.

(a): $^1$H NMR (500 MHz, DMSO-$d_6$, δ, ppm, inter alia): 9.05, 8.6 (2 m, 2H, $NH_2^+$), 8.4 (d, 1H, NHCO, J=8 Hz), 6.14 (dd, 1H, 19-H, J=11 Hz and 18 Hz), 5.55 (d, 1H, 14-H, J=8 Hz), 5.05 (m, 2H, 20-H), 3.65-3.55 (m, 2H, Pip-CHNH, 4'-H), 3.47 (d, 1H, 22 a-H, J=15 Hz), 3.42 (d, 1H, 11-H, J=6 Hz), 3.35-3.25 (m, 2H, 22 b-H, 2'-H), 3.17, 2.86 (2 m, 2H, Pip-H), 2.52 (m, 1H, 1'-H), 2.40 (bs, 1H, 4-H), 1.35 (s, 3H, 15-$CH_3$), 1.05 (s, 3H, 18-$CH_3$), 0.81 (d, 3H, 17-$CH_3$, J=7 Hz), 0.63 (d, 3H, 16-$CH_3$, J=7 Hz). MS-ESI (m/z): 619 ($M^+$).

(b): $^1$H NMR (500 MHz, DMSO-$d_6$, δ, ppm, inter alia): 9.0, 8.6 (2 m, 21-1, $NH_2^+$), 8.36 (d, 1H, NHCO, J=8 Hz), 6.14 (dd, 1H, 19-H, J=11 Hz and 18 Hz), 5.55 (d, 1H, 14-H, J=8 Hz), 5.06 (m, 2H, 20-H), 3.70-3.55 (m, 6H, Pip-CHNH, 4'-H, 22-H, 11-H, 2'-H), 3.18, 2.87 (2 m, 2H, Pip-H), 2.53 (m, 1H, 1'-H), 2.40 (bs, 1H, 4-H), 1.36 (s, 3H, 15-$CH_3$), 1.05 (s, 3H, 18-$CH_3$), 0.81 (d, 3H, 17-$CH_3$, J=7 Hz), 0.62 (d, 3H, 16-$CH_3$, J=7 Hz). MS-ESI (m/z): 619 ($M^+$).

Example 10

14-O-{[(1S,2S,4S)-4-((R)-2-Amino-3-hydroxy-propionylamino)-2-hydroxy-cyclohexylsulfanyl]-acetyl}-mutilin hydrochloride+(1R,2R,4R) diastereomer hydrochloride Diastereoisomeric Mixture of Compounds of Formula $I_{EX}$, Wherein $R_{EX}$ is a Group of Formula

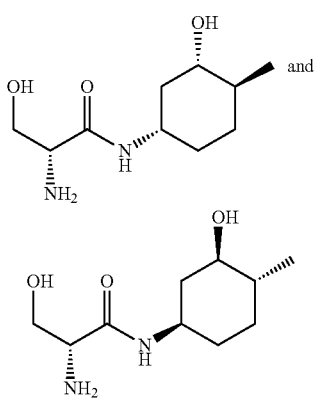

14-O-{[(1R,2R,4R)-4-Amino-2-hydroxy-cyclohexylsulfanyl]acetyl}-mutilin+(1S,2S,4S) diastereomer (1 g, 1.97 mmol) from Example 1 Step B is treated with (R)-2-tert-butoxycarbonylamino-3-hydroxy-propionic acid (Boc-D-serine, 364 mg, 1.77 mmol) according to the method of Example 4 Step A to C to give a mixture of 14-O-{[(1S,2S,4S)-4-((R)-2-amino-3-hydroxy-propionylamino)-2-hydroxy-cyclohexylsulfanyl]-acetyl}-mutilin hydrochloride+ (1R,2R,4R) diastereomer hydrochloride (yield: 200 mg) as a colorless solid.

$^1$H NMR (500 MHz, DMSO-d$_6$, δ, ppm, inter alia): 7.83 (m, 1H, NHCO), 6.13 (m, 1H, 19-H), 5.53 (m, 1H, 14-H), 5.04 (m, 2H, 20-H), 3.56 (m, 1H, 4'-H), 3.53-3.23 (m, 6H, Ser-CH$_2$OH, 22-H, 11-H, 2'-H), 3.13 (m, 1H, Ser-CHNH), 2.54 (m, 1H, 1'-H), 2.39 (bs, 1H, 4-H), 1.35 (s, 3H, 15-CH$_3$), 1.04 (s, 3H, 18-CH$_3$), 0.81 (m, 3H, 17-CH$_3$), 0.62 (m, 3H, 16-CH$_3$). MS-ESI (m/z): 617 (MNa$^+$), 629 (MCl$^-$).

Example 11

14-O-{[(1S*,2S*,5R*)-5-((R)-2-Amino-3-methyl-butyrylamino)-2-hydroxy-cyclohexylsulfanyl]-acetyl}-mutilin hydrochloride and 14-O-{[(1R*,2R*,5S*)-5-((R)-2-Amino-3-methyl-butyrylamino)-2-hydroxy-cyclohexylsulfanyl]-acetyl}-mutilin hydrochloride Compounds of Formula I$_{EX}$, Wherein R$_{EX}$ is a Group of Formula

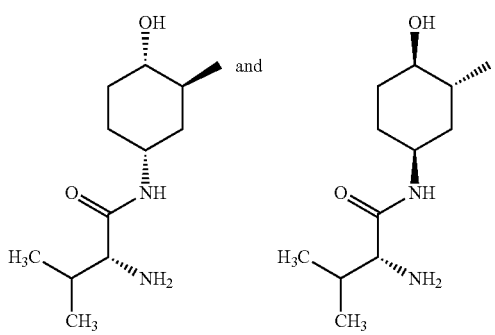

14-O-{[(1R,2R,5S)-5-Amino-2-hydroxy-cyclohexylsulfanyl]-mutilin+(1S,2S,5R) diastereomer (2.95 g, 5.81 mmol) from Example 2 is treated with (R)-2-tert-butoxycarbonylamino-3-methyl-butyric acid (Boc-D-valine, 1.14 g mg, 5.23 mmol) according to the method of Example 4 Step A to C to give 14-O-{[(1S*,2S*,5R*)-5-((R)-2-amino-3-methyl-butyrylamino)-2-hydroxy-cyclohexylsulfanyl]-acetyl}-mutilin hydrochloride (a) (yield: 900 mg) and 14-O-{[(1R*,2R*,5S*)-5-((R)-2-amino-3-methyl-butyrylamino)-2-hydroxy-cyclohexylsulfanyl]-acetyl}-mutilin hydrochloride (b) (yield: 1.04 g) as colorless solids.

(a): $^1$H NMR (500 MHz, DMSO-d$_6$, δ, ppm, inter alia): 7.9 (d, 1H, NHCO, J=7 Hz), 6.13 (dd, 1H, 19-H, J=11 Hz and 18 Hz), 5.53 (d, 1H, 14-H, J=8 Hz), 5.05 (m, 2H, 20-H), 4.91 (d, 1H, 2'-OH, J=4 Hz), 4.52 (d, 1H, 11-OH, J=6 Hz), 3.79 (m, 1H, 5'-H), 3.60-3.20 (m, 4H, 2'-H, 11-H, 22-H), 3.08, 2.97 (2 m, 2H, Val-CHNH, 1'-H), 2.40 (bs, 1H, 4-H), 1.35 (s, 3H, 15-CH$_3$), 1.04 (s, 3H, 18-CH$_3$), 0.88-0.77 (3d, 9H, 17-CH$_3$, 2×Val-CH$_3$, J=7 Hz), 0.62 (d, 3H, 16-CH$_3$, J=7 Hz). MS-ESI (m/z): 607 (M$^+$), 629 (MNa$^+$), 641 (MCl$^-$).

(b): $^1$H NMR (500 MHz, DMSO-d$_6$, δ, ppm, inter alia): 7.9 (d, 1H, NHCO, J=7 Hz), 6.12 (dd, 1H, 19-H, J=11 Hz and 18 Hz), 5.53 (d, 1H, 14-H, J=8 Hz), 5.04 (m, 2H, 20-H), 4.93 (d, 1H, 2'-OH, J=3 Hz), 4.51 (d, 1H, 11-OH, J=6 Hz), 3.78 (m, 1H, 5'-H), 3.60-3.20 (m, 4H, 2'-H, 11-H, 22-H), 3.14, 2.96 (2 m, 2H, Val-CHNH, 1'-H), 2.39 (bs, 1H, 4-H), 1.34 (s, 3H, 15-CH$_3$), 1.04 (s, 3H, 18-CH$_3$), 0.90-0.77 (3d, 9H, 17-CH$_3$, 2×Val-CH$_3$, J=7 Hz), 0.62 (d, 3H, 16-CH$_3$, J=7 Hz). MS-ESI (m/z): 607 (M$^+$), 629 (MNa$^+$), 641 (MCl$^-$).

Example 12

14-O-{[(1S*,2S*,5R*)-5-((S)-2-Amino-3-methyl-butyrylamino)-2-hydroxy-cyclohexylsulfanyl]-acetyl}-mutilin hydrochloride and 14-O-{[(1R*,2R*,5S*)-5-((S)-2-Amino-3-methyl-butyrylamino)-2-hydroxy-cyclohexylsulfanyl]-acetyl}-mutilin hydrochloride Compounds of Formula I$_{EX}$, Wherein R$_{EX}$ is a Group of Formula

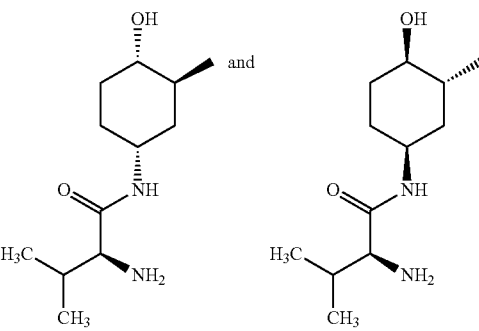

Step A. 14-O-{[(1S,2S,5R)-5-((S)-2-tert-Butoxycarbonylamino-3-methyl-butyrylamino)-2-hydroxy-cyclohexylsulfanyl]-acetyl}-mutilin+(1R,2R,5S) diastereomer To a solution of (S)-2-tert-butoxycarbonylamino-3-methyl-butyric acid (Boc-L-valine, 856 mg, 3.94 mmol) in 15 mL of DMF is added HOBT (532 mg, 3.94 mmol) and EDC (755 mg, 3.94 mmol) and stirred for 30 min at RT. Then a solution of 14-O-{[(1R,2R,5S)-5-amino-2-hydroxy-cyclohexylsulfanyl]-acetyl}-mutilin+(1S,2S,5R) diastereomer (2 g, 3.94 mmol) from Example 2 in DMF is added and the resulting mixture is stirred at RT until completion of the reaction (typically overnight). The reaction mixture is charged with brine and extracted with CH$_2$Cl$_2$. The organic layers are dried over Na$_2$SO$_4$ and filtered. The filtrate is concentrated under reduced pressure and subjected to chromatography (silica, cHex I EtOAc=½) yielding 14-O-{[(1S,2S,5R)-5-((S)-2-tert-butoxycarbonylamino-3-methyl-butyrylamino)-2-hydroxy-cyclohexylsulfanyl]-acetyl}-mutilin+(1R,2R,5S) diastereomer (yield: 2.016 g, 72% yield) as colorless foam.

$^1$H NMR (200 MHz, DMSO-d$_6$, δ, ppm, inter alia): 7.7 (m, 1H, NHCO), 6.5 (m, 1H, NHCO), 6.12 (dd, 1H, 19-H, J=11 Hz and 17 Hz), 5.55 (d, 1H, 14-H, J=7 Hz), 5.05 (m, 2H, 20-H), 4.92 (d, 2H, 2'-OH, J=3 Hz), 4.53 (d, 1H, 11-OH, J=6 Hz), 3.85-3.20 (m, 6H, Val-CHNH, 5'-H, 11-H, 22-H, 2'-H), 2.99 (m, 1H, 1'-H), 2.40 (bs, 1H, 4-H), 1.36 (bs, 12H, tert-butyl, 15-CH$_3$), 1.05 (s, 3H, 18-CH$_3$), 0.90-0.70 (m, 9H, 17-CH$_3$, 2× Val-CH$_3$), 0.63 (m, 3H, 16-CH$_3$).

Step B and C. 14-O-{[(1S*,2S*,5R*)-5-((S)-2-Amino-3-methyl-butyrylamino)-2-hydroxy-cyclohexylsulfanyl]-acetyl}-mutilin hydrochloride and 14-O-{[(1R*,2R*,5S*)-5-((S)-2-Amino-3-methyl-butyrylamino)-2-hydroxy-cyclohexylsulfanyl]-acetyl}-mutilin hydrochloride 14-O-{[(1S,2S,5R)-5-((S)-2-tert-butoxycarbonylamino-3-methyl-butyrylamino)-2-hydroxy-cyclohexylsulfanyl]-acetyl}-mutilin+(1R,2R,5S) diastereomer (1 g, 1.41 mmol) is treated according to the method of Example 4 Step B and C to give 14-O-{[(1S*,2S*,5R*)-5-((S)-2-amino-3-methyl-butyrylamino)-2-hydroxy-cyclohexylsulfanyl]-acetyl}-mutilin hydrochloride (a) (yield: 270 mg) and 14-O-{[(1R*,2R*,5S*)-5-((S)-2-amino-3-methyl-butyrylamino)-2-hydroxy-cyclohexylsulfanyl]-acetyl}-mutilin hydrochloride (b) (yield: 230 mg) as colorless solids.

(a): $^1$H NMR (200 MHz, DMSO-d$_6$, δ, ppm, inter alia): 8.4 (d, 1H, NHCO, J=7 Hz), 8.15 (m, 3H, NH$_3^+$), 6.13 (dd, 1H, 19-H, J=11 Hz and 18 Hz), 5.55 (d, 1H, 14-H, J=8 Hz), 5.05 (m, 2H, 20-H), 3.80 (m, 1H, 5'-H), 3.70-3.00 (m, 6H, 2'-H, 11-H, 22-H, Val-CHNH, 1H), 2.40 (bs, 1H, 4-H), 1.36 (s, 3H, 15-CH$_3$), 1.06 (s, 3H, 18-CH$_3$), 0.98-0.87 (2d, 6H, 2× Val-CH$_3$, J=7 Hz), 0.82 (d, 3H, 17-CH$_3$, J=7 Hz), 0.63 (d, 3H, 16-CH$_3$, J=6 Hz). MS-ESI (m/z): 607 (M$^+$), 651 (Mformate$^-$).

(b): $^1$H NMR (200 MHz, DMSO-d$_6$, δ, ppm, inter alia): 8.4 (d, 1H, NHCO, J=8 Hz), 8.2 (m, 3H, NH$_3^+$), 6.13 (dd, 1H, 19-H, J=11 Hz and 18 Hz), 5.54 (d, 1H, 14-H, J=8 Hz), 5.06 (m, 2H, 20-H), 3.83 (m, 1H, 5'-H), 3.65-2.90 (m, 6H, 2'-H, 11-H, 22-H, Val-CHNH, 1'-H), 2.40 (bs, 1H, 4-H), 1.36 (s, 3H, 15-CH$_3$), 1.06 (s, 3H, 18-CH$_3$), 0.93 (d, 6H, 2× Val-CH$_3$, J=7 Hz), 0.82 (d, 3H, 17-CH$_3$, J=7 Hz), 0.62 (d, 3H, 16-CH$_3$, J=6 Hz). MS-ESI (m/z): 607 (M$^+$), 651 (Mformate$^-$).

Example 13

14-O-{[(1S*,2S*,5R*)-5-((S)-2-Amino-3-methyl-butyrylamino)-2-hydroxy-cyclohexylsulfanyl]-acetyl}-19,20-dihydro-mutilin hydrochloride and 14-O-{[(1R*,2R*,5S*)-5-((S)-2-Amino-3-methyl-butyrylamino)-2-hydroxy-cyclohexylsulfanyl]-acetyl}-19,20-dihydro-mutilin hydrochloride Compounds of Formula I$_{EX}$, Wherein R$_{EX}$ is a Group of Formula

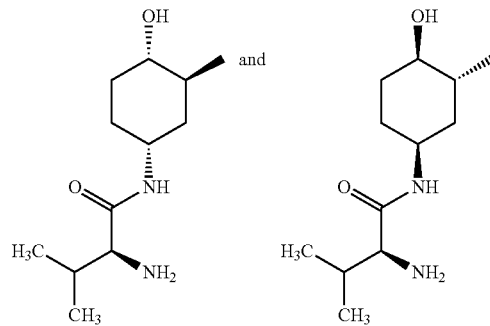

Step A. 14-O-{[(1S,2S,5R)-5-((S)-2-tert-Butoxycarbonylamino-3-methyl-butyrylamino)-2-hydroxy-cyclohexylsulfanyl]acetyl}-19,20-dihydro-mutilin+ (1R,2R,5S) diastereomer A solution of 14-O-{[(1S,2S,5R)-5-((S)-2-tert-butoxycarbonylamino-3-methyl-butyrylamino)-2-hydroxy-cyclohexylsulfanyl]acetyl}-mutilin+(1R,2R,5S) diastereomer (1 g, 1.41 mmol) from Example 12 Step A in 30 mL of ethanol is hydrogenated over 10% palladium on charcoal (H-Cube, 50° C., 50 bar) to give 14-O-{[(1S,2S,5R)-5-((S)-2-tert-butoxycarbonylamino-3-methyl-butyrylamino)-2-hydroxy-cyclohexylsulfanyl]acetyl}-19,20-dihydro-mutilin+(1R,2R,5S) diastereomer (yield: 879 mg, 88% th) as a colorless foam.

$^1$H NMR (200 MHz, DMSO-d$_6$, δ, ppm, inter alia): 7.7 (m, 1H, NHCO), 6.5 (m, 1H, NHCO), 5.52 (m, 1H, 14-H), 4.93 (d, 2H, 2'-OH, J=3 Hz), 3.85-3.20 (m, 6H, Val-CHNH, 5'-H, 11-H, 22-H, 2'-H), 3.03 (m, 11-1,1'-H), 2.37 (bs, 1H, 4-H), 1.35 (m, 12H, tert-butyl, 15-CH$_3$), 0.90-0.80 (m, 12H, 18-CH$_3$, 17-CH$_3$, 2× Val-CH$_3$), 0.80-0.55 (m, 6H, 20-H, 16-CH$_3$).

Step B and C. 14-O-{[(1S*,2S*,5R*)-5-((S)-2-Amino-3-methyl-butyrylamino)-2-hydroxy-cyclohexylsulfanyl]-acetyl}-19,20-dihydro-mutilin hydrochloride and a mixture of 14-O-{[(1R,2R,5S)-5-((S)-2-Amino-3-methyl-butyrylamino)-2-hydroxy-cyclohexylsulfanyl]acetyl}-19,20-dihydro-mutilin hydrochloride+(1S,2S,5R) diastereomer hydrochloride 14-O-{[(1S,2S,5R)-5-((S)-2-tert-Butoxycarbonylamino-3-methyl-butyrylamino)-2-hydroxy-cyclohexylsulfanyl]acetyl}-19,20-dihydro-mutilin+(1R,2R,5S) diastereomer (879 mg, 1.24 mmol) is treated according to the method of Example 4 Step B and C to give 14-O-{[(1S*,2S*,5R*)-5-((S)-2-amino-3-methyl-butyrylamino)-2-hydroxy-cyclohexylsulfanyl]-acetyl}-19,20-dihydro-mutilin hydrochloride (a) (yield: 190 mg) as well as a mixture of 14-O-{[(1R,2R,5S)-5-((S)-2-amino-3-methyl-butyrylamino)-2-hydroxy-cyclohexylsulfanyl]-acetyl}-19,20-dihydro-mutilin hydrochloride+(1S,2S,5R) diastereomer hydrochloride (b) (yield: 328 mg) as colorless foams.

(a): $^1$H NMR (400 MHz, DMSO-d$_6$, δ, ppm, inter alia): 8.3 (d, 1H, NHCO, J=7 Hz), 7.95 (m, 3H, NH$_3^+$), 5.54 (d, 1H, 14-H, J=8 Hz), 4.95 (d, 1H, 2'-OH, J=3 Hz), 4.41 (d, 1H, 11-OH, J=6 Hz), 3.90-3.25 (m, 6H, 5'-H, 2'-H, 11-H, 22-H, Val-CHNH), 3.07 (m, 1H, 1'-H), 2.38 (bs, 1H, 4-H), 1.37 (s, 3H, 15-CH$_3$), 0.93 (d, 6H, 2× Val-CH$_3$, J=7 Hz), 0.87 (s, 3H, 18-CH$_3$), 0.83 (d, 3H, 17-CH$_3$, J=7 Hz), 0.70-0.60 (m, 6H, 20-H, 16-CH$_3$). MS-ESI (m/z): 609 (M$^+$).

(b): ¹H NMR (400 MHz, DMSO-d₆, δ, ppm, inter alia): 8.0 (d, 1H, NHCO, J=7 Hz), 5.54 (d, 1H, 14-H, J=8 Hz), 4.95 (m, 1H, 2'-OH), 4.40 (m, 1H, 11-OH), 3.90-3.25 (m, 6H, 5'-H, 2'-H, 11-H, 22-H, Val-CHNH), 3.06, 3.00 (2 m, 1H, 1'-H), 2.37 (bs, 1H, 4-H), 1.36 (s, 3H, 15-CH₃), 0.95-0.80 (m, 12H, 2× Val-CH₃, 18-CH₃, 17-CH₃), 0.70-0.60 (m, 6H, 20-H, 16-CH₃). MS-ESI (m/z): 609 (M⁺).

Example 14

14-O-{[(1S*,2S*,5R*)-5-((R)-2-Amino-propionylamino)-2-hydroxy-cyclohexylsulfanyl]-acetyl}-mutilin hydrochloride and 14-O-{[(1R*,2R*,5S*)-5-((R)-2-Amino-propionylamino)-2-hydroxy-cyclohexylsulfanyl]-acetyl}-mutilin hydrochloride Compounds of Formula I$_{EX}$, Wherein R$_{EX}$ is a Group of Formula

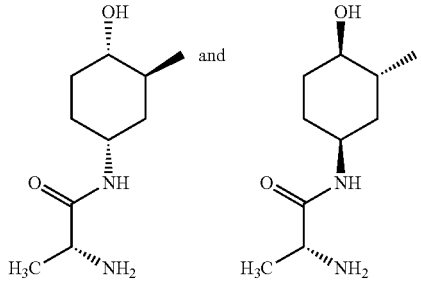

14-O-{[(1R,2R,5S)-5-Amino-2-hydroxy-cyclohexylsulfanyl]-acetyl}-mutilin+(1S,2S,5R) diastereomer (1.55 g, 3.05 mmol) from Example 2 is treated with (R)-2-tert-butoxycarbonylamino-propionic acid (Boc-D-alanine, 578 mg, 3.05 mmol) according to the method of Example 4 Step A to C to give 14-O-{[(1S*,2S*,5R*)-5-((R)-2-amino-propionylamino)-2-hydroxy-cyclohexylsulfanyl]acetyl}-mutilin hydrochloride (a) (yield: 416 mg) and 14-O-{[(1R*,2R*,5S*)-5-((R)-2-amino-propionylamino)-2-hydroxy-cyclohexylsulfanyl]-acetyl}-mutilin hydrochloride (b) (yield: 490 mg) as colorless solids.

(a): ¹H NMR (500 MHz, DMSO-d₆, δ, ppm, inter alia): 7.96 (d, 1H, NHCO, J=7 Hz), 6.13 (dd, 1H, 19-H, J=11 Hz and 18 Hz), 5.53 (d, 1H, 14-H, J=8 Hz), 5.06 (m, 2H, 20-H), 4.93 (d, 1H, 2'-OH, J=3 Hz), 4.52 (d, 1H, 11-OH, J=6 Hz), 3.76 (m, 1H, 5'-H), 3.60-3.20 (m, 5H, 2'-H, Ala-CHNH, 11-H, 22-H), 2.97 (m, 1H, 1'-H), 2.40 (bs, 1H, 4-H), 1.35 (s, 3H, 15-CH₃), 1.19 (d, 3H, Ala-CH₃, J=7 Hz), 1.04 (s, 3H, 18-CH₃), 0.81 (d, 3H, 17-CH₃, J=7 Hz), 0.62 (d, 3H, 16-CH₃, J=7 Hz). MS-ESI (m/z): 579 (M⁺), 601 (MNa⁺), 613 (MCl⁻).

(b): ¹H NMR (500 MHz, DMSO-d₆, δ, ppm, inter alia): 7.9 (d, 1H, NHCO, J=7 Hz), 6.13 (dd, 1H, 19-H, J=11 Hz and 18 Hz), 5.53 (d, 1H, 14-H, J=8 Hz), 5.04 (m, 2H, 20-H), 4.92 (d, 1H, 2'-OH, J=4 Hz), 4.51 (d, 1H, 11-OH, J=6 Hz), 3.76 (m, 1H, 5'-H), 3.60-3.20 (m, 5H, 2'-H, Ala-CHNH, 11-H, 22-H), 2.98 (m, 1H, 1'-H), 2.40 (bs, 1H, 4-H), 1.35 (s, 3H, 15-CH₃), 1.19 (d, 3H, Ala-CH₃, J=7 Hz), 1.05 (s, 3H, 18-CH₃), 0.81 (d, 3H, 17-CH₃, J=7 Hz), 0.63 (d, 3H, 16-CH₃, J=7 Hz). MS-ESI (m/z): 579 (M⁺), 601 (MNa⁺), 613 (MCl⁻).

Example 15

14-O-{[(1S,2S,5R)-5-((S)-2-Amino-propionylamino)-2-hydroxy-cyclohexylsulfanyl]-acetyl}-mutilin hydrochloride+(1R,2R,5S) diastereomer hydrochloride Diastereoisomeric Mixture of Compounds of Formula I$_{EX}$, Wherein R$_{EX}$ is a Group of Formula

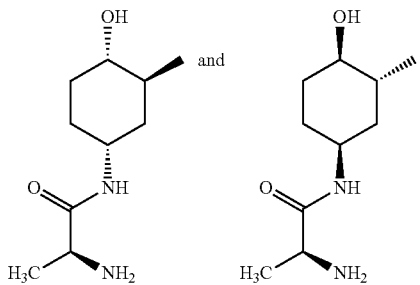

14-O-{[(1R,2R,5S)-5-Amino-2-hydroxy-cyclohexylsulfanyl]-acetyl}-mutilin+(1S,2S,5R) diastereomer (1 g, 1.97 mmol) from Example 2 is treated with (S)-2-tert-butoxycarbonylamino-propionic acid (Boc-L-alanine, 373 mg, 1.97 mmol) according to the method of Example 4 Step A to C to give a mixture of 14-O-{[(1S,2S,5R)-5-((S)-2-Amino-propionylamino)-2-hydroxy-cyclohexylsulfanyl]acetyl}-mutilin hydrochloride+(1R,2R,5S) diastereomer hydrochloride (yield: 507 mg) as a colorless solid.

¹H NMR (200 MHz, DMSO-d₆, δ, ppm, inter alia): 8.35 (d, 1H, NHCO, J=8 Hz), 8.2 (bs, 3H, NH₃⁺), 6.14 (dd, 1H, 19-H, J=11 Hz and 17 Hz), 5.55 (m, 1H, 14-Hz), 5.05 (m, 2H, 20-H), 3.90-3.25 (m, 5H, Ala-CHNH, 5'-H, 11-H, 22-H), 3.02 (m, 1H, 1'-H), 2.40 (bs, 1H, 4-H), 1.36 (s, 3H, 15-CH₃), 1.06 (s, 3H, 18-CH₃), 0.82 (d, 3H, 17-CH₃, J=7 Hz), 0.63 (d, 3H, 16-CH₃, J=6 Hz). MS-ESI (m/z): 579 (M⁺), 623 (Mformate⁻).

Example 16

14-O-{[(1S*,2S*,5R*)-2-Hydroxy-5-[((R)-piperidine-2-carbonyl)-amino]-cyclohexylsulfanyl]-acetyl}-mutilin hydrochloride and 14-O-{[(1R*,2R*,5S*)-2-Hydroxy-5-[((R)-piperidine-2-carbonyl)-amino]cyclohexylsulfanyl]-acetyl}-mutilin hydrochloride Compounds of Formula I$_{EX}$, Wherein R$_{EX}$ is a Group of Formula

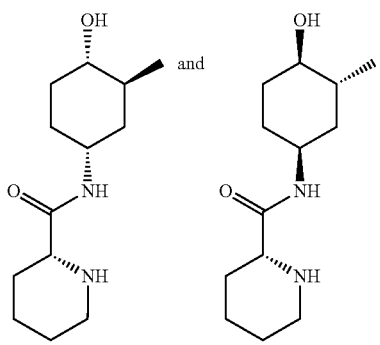

Step A. 14-O-{[(1S,2S,5R)-5-[((R)—N-tert-Butoxy-carbonyl-piperidine-2-carbonyl)-amino]-2-hydroxy-cyclohexylsulfanyl]-acetyl}-mutilin+(1R,2R,5S) diastereomer To a solution of (R)-1-(tert-butoxycarbonyl)-2-piperidinecarboxylic acid (Boc-D-pipecolinic acid, Boc-D-homoproline, 860 mg, 3.74 mmol) in 40 mL of $CH_2Cl_2$ is added HOBT (506 mg, 3.74 mmol) and EDC (717 mg, 3.74 mmol) and stirred for 30 min at RT. Then 14-O-{[(1R,2R,5S)-5-amino-2-hydroxy-cyclohexylsulfanyl]-acetyl}-mutilin+(1S,2S,5R) diastereomer-(1.90 g, 3.74 mmol) from Example 2 is added and the resulting mixture is stirred at RT until completion of the reaction (typically overnight). The reaction mixture is charged with brine and extracted with $CH_2Cl_2$. The organic layers are dried over $Na_2SO_4$ and filtered. The filtrate is concentrated under reduced pressure and subjected to chromatography (silica, cHex/EtOAc=¼) yielding 14-O-{[(1S,2S,5R)-5-[((R)—N-tert-butoxycarbonyl-piperidine-2-carbonyl)-amino]-2-hydroxy-cyclohexylsulfanyl]acetyl}-mutilin+(1R,2R,5S) diastereomer (yield: 2.28 g, 98% th) as a colorless foam.

$^1$H NMR (400 MHz, DMSO-$d_6$, δ, ppm, inter alia): 7.6 (m, 1H, NHCO), 6.14 (dd, 1H, 19-H, J=11 Hz and 18 Hz), 5.55 (d, 1H, 14-H, J=8 Hz), 5.05 (m, 2H, 20-H), 4.88 (m, 2H, 2'-OH), 4.49 (m, 1H, 11-OH), 4.40 (bs, 1H, Pip-CHNH), 3.80-2.90 (m, 8H, Pip-H, 5'-H, 2'-H, 11-H, 22-H, Pip-H, 1'-H), 2.40 (bs, 1H, 4-H), 1.36 (bs, 12H, tert-butyl, 15-CH$_3$), 1.06 (s, 3H, 18-CH$_3$), 0.82 (m, 3H, 17-CH$_3$, J=6 Hz), 0.63 (m, 3H, 16-CH$_3$). MS-ESI (m/z): 741 (MNa$^+$), 753 (MO).

Step B and C. 14-O-{[(1S*,2S*,5R*)-2-Hydroxy-5-[((R)-piperidine-2-carbonyl)-amino]-cyclohexylsulfanyl]-acetyl}-mutilin hydrochloride and 14-O-{[(1R*,2R*,5S*)-2-Hydroxy-5-[((R)-piperidine-2-carbonyl)-amino]-cyclohexylsulfanyl]-acetyl}-mutilin hydrochloride 14-O-{[(1S,2S,5R)-5-[((R)—N-tert-Butoxycarbonyl-piperidine-2-carbonyl)-amino]-2-hydroxy-cyclohexylsulfanyl]-acetyl}-mutilin+(1R,2R,5S) diastereomer (1.28 g, 1.78 mmol) is treated according to the method of Example 4 Step B and C to give 14-O-{[(1S*,2S*,5R*)-2-hydroxy-5-[((R)-piperidine-2-carbonyl)-amino]-cyclohexylsulfanyl]-acetyl}-mutilin hydrochloride (a) (yield: 152 mg) and 14-O-{[(1R*,2R*,5S*)-2-hydroxy-5-[((R)-piperidine-2-carbonyl)-amino]-cyclohexylsulfanyl]-acetyl}-mutilin hydrochloride (b) (yield: 119 mg) as colorless solids.

(a): $^1$H NMR (500 MHz, DMSO-$d_6$, δ, ppm, inter alia): 7.82 (d, 1H, NHCO, J=7 Hz), 6.13 (dd, 1H, 19-H, J=11 Hz and 18 Hz), 5.55 (d, 1H, 14-H, J=8 Hz), 5.05 (m, 2H, 20-H), 4.92 (d, 1H, 2'-OH, J=4 Hz), 4.52 (d, 1H, 11-OH, J=6 Hz), 3.77 (m, 1H, 5'-H), 3.60-3.20 (m, 5H, 2'-H, 11-H, Pip-CHNH, 22-H), 3.03 (m, 1H, Pip-H), 2.97 (m, 1H, 1'-H), 2.65 (m, 1H, Pip-H), 2.39 (bs, 1H, 4-H), 1.36 (s, 3H, 15-CH$_3$), 1.05 (s, 3H, 18-CH$_3$), 0.81 (d, 3H, 17-CH$_3$, J=7 Hz), 0.62 (d, 3H, 16-CH$_3$, J=7 Hz). MS-ESI (m/z): 619 (M$^+$), 653 (MCl$^-$).

(b): $^1$H NMR (500 MHz, DMSO-$d_6$, δ, ppm, inter alia): 7.75 (d, 1H, NHCO, J=8 Hz), 6.13 (dd, 1H, 19-H, J=11 Hz and 18 Hz), 5.53 (d, 1H, 14-H, J=8 Hz), 5.04 (m, 2H, 20-H), 4.92 (d, 1H, 2'-OH, J=4 Hz), 4.52 (d, 1H, 11-OH, J=6 Hz), 3.77 (m, 1H, 5'-H), 3.60-3.20 (m, 5H, 2'-H, 11-H, Pip-CHNH, 22-H), 2.97 (m, 2H, Pip-H, 1'-H), 2.62 (m, 1H, Pip-H), 2.39 (bs, 1H, 4-H), 1.36 (s, 3H, 15-CH$_3$), 1.05 (s, 3H, 18-CH$_3$), 0.81 (d, 3H, 17-CH$_3$, J=7 Hz), 0.63 (d, 3H, 16-CH$_3$, J=7 Hz). MS-ESI (m/z): 619 (M$^+$), 653 (MCl$^-$).

Example 17

14-O-{[(1S*,2S*,5R*)-2-Hydroxy-5-[((R)-piperidine-2-carbonyl)-amino]-cyclohexylsulfanyl]-acetyl}-19,20-dihydro-mutilin hydrochloride and 14-O-{[(1R*,2R*,5S*)-2-Hydroxy-5-[((R)-piperidine-2-carbonyl)-amino]-cyclohexylsulfanyl]-acetyl}-19,20-dihydro-mutilin hydrochloride Compounds of Formula I$_{EX}$, Wherein R$_{EX}$ is a Group of Formula

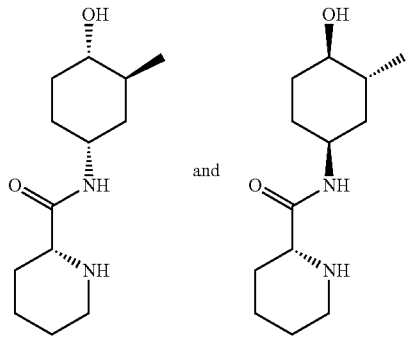

14-O-{[(1S,2S,5R)-5-[((R)—N-tert-Butoxycarbonyl-piperidine-2-carbonyl)-amino]-2-hydroxy-cyclohexylsulfanyl]acetyl}-mutilin+(1R,2R,5S) diastereomer (1 g, 1.39 mmol) from Example 16 Step A is treated according to the method of Example 13 Step A to C to give 14-O-{[(1S*,2S*,5R*)-2-hydroxy-5-[((R)-piperidine-2-carbonyl)-amino]-cyclohexylsulfanyl]acetyl}-19,20-dihydro-mutilin hydrochloride (a) (yield: 217 mg) and 14-O-{[(1R*,2R*,5*S)-2-hydroxy-5-[((R)-piperidine-2-carbonyl)-amino]-cyclohexylsulfanyl]-acetyl}-19,20-dihydro-mutilin hydrochloride (b) (yield: 180 mg) as colorless solids.

(a): $^1$H NMR (400 MHz, DMSO-$d_6$, δ, ppm, inter alia): 8.7 (m, 2H, NH$_2^+$), 8.3 (d, 1H, NHCO, J=7 Hz), 5.54 (d, 1H, 14-H, J=8 Hz), 4.96 (d, 1H, 2'-OH, J=4 Hz), 4.41 (d, 1H, 11-OH, J=6 Hz), 3.90-3.25 (m, 6H, 5'-H, 2'-H, 11-H, Pip-CHNH, 22-H), 3.20, 3.02, 2.88 (3 m, 3H, 2×Pip-H, 1'-H), 2.38 (bs, 1H, 4-H), 1.37 (s, 3H, 15-CH$_3$), 0.88 (s, 3H, 18-CH$_3$), 0.83 (d, 3H, 17-CH$_3$, J=7 Hz), 0.70-0.60 (m, 6H, 20-H, 16-CH$_3$). MS-ESI (m/z): 621 (M$^+$).

(b): $^1$H NMR (400 MHz, DMSO-$d_6$, δ, ppm, inter alia): 8.7 (m, 2H, NH$_2^+$), 8.3 (d, 1H, NHCO, J=7 Hz), 5.55 (d, 1H, 14-H, J=8 Hz), 4.99 (d, 1H, J=4 Hz), 4.42 (d, 1H, 11-OH, J=6 Hz), 3.90-3.25 (m, 6H, 5'-H, 2'-H, 11-H, Pip-CHNH, 22-H), 3.20, 3.06, 2.88 (3 m, 3H, 2×Pip-H, 1'-H), 2.37 (bs, 1H, 4-H), 1.36 (s, 3H, 15-CH$_3$), 0.87 (s, 3H, 18-CH$_3$), 0.83 (d, 3H, 17-CH$_3$, J=7 Hz), 0.70-0.60 (m, 6H, 20-H, 16-CH$_3$). MS-ESI (m/z): 621 (M$^+$).

Example 18

14-O-{[(1S*,2*S,5R*)-2-Hydroxy-5-[((S)-piperidine-2-carbonyl)-amino]-cyclohexylsulfanyl]-acetyl}-mutilin hydrochloride and 14-O-{[(1R*,2R*,5*S)-2-Hydroxy-5-[((S)-piperidine-2-carbonyl)-amino]-cyclohexylsulfanyl]-acetyl}-mutilin hydrochloride Compounds of Formula I$_{EX}$, Wherein R$_{EX}$ is a Group of Formula

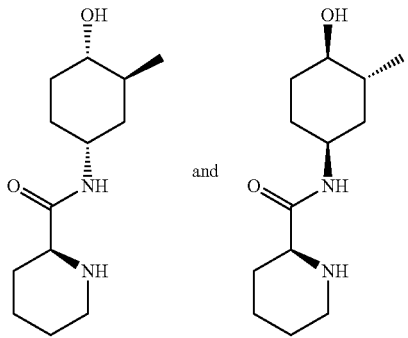

Step A. 14-O-{[(1S,2S,5R)-5-[((S)—N-tert-Butoxycarbonyl-piperidine-2-carbonyl)-amino]-2-hydroxy-cyclohexylsulfanyl]-acetyl}-mutilin+(1R,2R,5S) diastereomer To a solution of (S)-1-(tert-butoxycarbonyl)-2-piperidinecarboxylic acid (Boc-L-pipecolinic acid, Boc-L-homoproline, 903 mg, 3.94 mmol) in 20 mL of DMF is added HOBT (532 mg, 3.94 mmol) and EDC (755 mg, 3.94 mmol) and stirred for 30 min at RT. Then 14-O-{[(1R,2R, 5S)-5-amino-2-hydroxy-cyclohexylsulfanyl]-acetyl}-mutilin+(1S,2S,5R) diastereomer (2 g, 3.94 mmol) from Example 2 is added and the resulting mixture is stirred at RT until completion of the reaction (typically overnight). The reaction mixture is charged with brine and extracted with CH$_2$Cl$_2$. The organic layers are dried over Na$_2$SO$_4$ and filtered. The filtrate is concentrated under reduced pressure and subjected to chromatography (silica, cHex/EtOAc=¼) yielding 14-O-{[(1S,2S, 5R)-5-[((S)—N-tert-butoxycarbonyl-piperidine-2-carbonyl)-amino]-2-hydroxy-cyclohexylsulfanyl]acetyl}-mutilin+(1R,2R,5S) diastereomer (yield: 2.29 g, 81% th) as a colorless foam.

$^1$H NMR (200 MHz, DMSO-d$_6$, δ, ppm, inter alia): 7.6 (m, 1H, NHCO), 6.14 (dd, 1H, 19-H, J=11 Hz and 18 Hz), 5.55 (d, 1H, 14-H, J=7 Hz), 5.06 (m, 2H, 20-H), 4.90 (m, 2H, 2'-OH), 4.52 (m, 1H, 11-OH), 4.4 (bs, 1H, Pip-CHNH), 3.85-2.90 (m, 8H, Pip-H, 5'-H, 2'-H, 11-H, 22-H, Pip-H, 1'-H), 2.40 (bs, 1H, 4-H), 1.36 (bs, 12H, tert-butyl, 15-CH$_3$), 1.06 (s, 3H, 18-CH$_3$), 0.82 (d, 3H, 17-CH$_3$, J=7 Hz), 0.63 (d, 3H, 16-CH$_3$, J=6 Hz).

Step B and C. 14-O-{[(1S*,2S*,5R*)-2-Hydroxy-5-[((S)-piperidine-2-carbonyl)-amino]-cyclohexylsulfanyl]-acetyl}-mutilin hydrochloride and 14-O-{[(1R*,2R*,5S*)-2-Hydroxy-5-[((S)-piperidine-2-carbonyl)-amino]-cyclohexylsulfanyl]-acetyl}-mutilin hydrochloride 14-O-{[(1S,2S,5R)-5-[((S)—N-tert-Butoxycarbonyl-piperidine-2-carbonyl)-amino]-2-hydroxy-cyclohexylsulfanyl]-acetyl}-mutilin+(1R,2R,5S) diastereomer (1.28 g, 1.78 mmol) is treated according to the method of Example 4 Step B and C to give 14-O-{[(1S*,2S*,5R*)-2-hydroxy-5-[((S)-piperidine-2-carbonyl)-amino]-cyclohexylsulfanyl]-acetyl}-mutilin hydrochloride (a) (yield: 427 mg) and 14-O-{[(1R*, 2R*,5*S)-2-hydroxy-5-[((S)-piperidine-2-carbonyl)-amino]-cyclohexylsulfanyl]-acetyl}-mutilin hydrochloride (b) (yield: 342 mg) as colorless solids.

(a): $^1$H NMR (200 MHz, DMSO-d$_6$, δ, ppm, inter alia): 9.2, 8.6 (2 m, 2H, NH$_2^+$), 8.45 (d, 1H, NHCO, J=7 Hz), 6.14 (dd, 1H, 19-H, J=11 Hz and 18 Hz), 5.55 (d, 1H, 14-H, J=8 Hz), 5.05 (m, 2H, 20-H), 3.90-2.75 (m, 9H, 5'-H, 2'-H, 11-H, Pip-CHNH, 22-H, 2× Pip-H, 1"-H), 2.41 (bs, 1H, 4-H), 1.36 (s, 3H, 15-CH$_3$), 1.06 (s, 3H, 18-CH$_3$), 0.82 (d, 3H, 17-CH$_3$, J=7 Hz), 0.63 (d, 3H, 16-CH$_3$, J=6 Hz). MS-ESI (m/z): 619 (M$^+$), 663 (Mformate$^-$).

(b): $^1$H NMR (200 MHz, DMSO-d$_6$, δ, ppm, inter alia): 9.2, 8.6 (2 m, 2H, NH$_2^+$), 8.45 (d, 1H, NHCO, J=8 Hz), 6.14 (dd, 1H, 19-H, J=11 Hz and 18 Hz), 5.55 (d, 1H, 14-H, J=8 Hz), 5.06 (m, 2H, 20-H), 3.90-2.75 (m, 9H, 5'-H, 2'-H, 11-H, Pip-CHNH, 22-H, 2× Pip-H, 1"-H), 2.41 (bs, 1H, 4-H), 1.36 (s, 3H, 15-CH$_3$), 1.05 (s, 3H, 18-CH$_3$), 0.82 (d, 3H, 17-CH$_3$, J=7 Hz), 0.63 (d, 3H, 16-CH$_3$, J=6 Hz). MS-ESI (m/z): 619 (M$^+$), 663 (Mformate$^-$).

Example 19

14-O-{[(1S*,2S*,5R*)-2-Hydroxy-5-[((S)-piperidine-2-carbonyl)-amino]-cyclohexylsulfanyl]acetyl}-19,20-dihydro-mutilin hydrochloride and 14-O-{[(1R*,2R*,5S*)-2-Hydroxy-5-[((S)-piperidine-2-carbonyl)-amino]-cyclohexylsulfanyl]-acetyl}-19,20-dihydro-mutilin hydrochloride Compounds of Formula I$_{EX}$, Wherein R$_{EX}$ is a Group of Formula

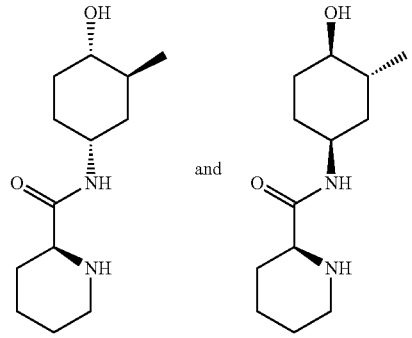

14-O-{[(1S,2S,5R)-5-[((S)—N-tert-Butoxycarbonyl-piperidine-2-carbonyl)-amino]-2-hydroxy-cyclohexylsulfanyl] acetyl}-mutilin+(1R,2R,5S) diastereomer (1 g, 1.39 mmol) from Example 18 Step A is treated according to the method of Example 13 Step A to C to give 14-O-{[(1S*,2S*,5R*)-2-hydroxy-5-[((S)-piperidine-2-carbonyl)-amino]-cyclohexylsulfanyl]acetyl}-19,20-dihydro-mutilin hydrochloride (a) (yield: 236 mg) and 14-O-{[(1R*,2R*,5S*)-2-hydroxy-5-[((S)-piperidine-2-carbonyl)-amino]-cyclohexylsulfanyl]-acetyl}-19,20-dihydro-mutilin hydrochloride (b) (yield: 197 mg) as colorless solids.

(a): $^1$H NMR (400 MHz, DMSO-d$_6$, δ, ppm, inter alia): 8.7 (m, 2H, NH$_2^+$), 8.3 (d, 1H, NHCO, J=7 Hz), 5.54 (d, 1H, 14-H, J=8 Hz), 4.96 (d, 1H, 2'-OH, J=4 Hz), 4.42 (d, 1H, 11-OH, J=6 Hz), 3.90-3.25 (m, 6H, 5'-H, 2'-H, 11-H, Pip-CHNH, 22-H), 3.20, 3.05, 2.89 (3 m, 3H, 2× Pip-H, 1'-H), 2.38 (bs, 1H, 4-H), 1.37 (s, 3H, 15-CH$_3$), 0.87 (s, 3H, 18-CH$_3$), 0.83 (d, 3H, 17-CH$_3$, J=7 Hz), 0.70-0.60 (m, 6H, 20-H, 16-CH$_3$). MS-ESI (m/z): 621 (M$^+$).

(b): $^1$H NMR (400 MHz, DMSO-d$_6$, δ, ppm, inter alia): 8.7 (m, 2H, NH$_2^+$), 8.3 (d, 1H, NHCO, J=7 Hz), 5.54 (d, 1H, 14-H, J=8 Hz), 4.97 (d, 1H, J=4 Hz), 4.41 (d, 1H, 11-OH, J=6 Hz), 3.90-3.25 (m, 6H, 5'-H, 2'-H, 11-H, Pip-CHNH, 22-H), 3.20, 3.02, 2.88 (3 m, 3H, 2× Pip-H, 1'-H), 2.37 (bs, 1H, 4-H), 1.36 (s, 3H, 15-CH$_3$), 0.87 (s, 3H, 18-CH$_3$), 0.83 (d, 3H, 17-CH$_3$, J=7 Hz), 0.70-0.60 (m, 6H, 20-H, 16-CH$_3$). MS-ESI (m/z): 621 (M$^+$).

Example 20

14-O-{[(1S*,2S*,5R*)-5-((R)-2-Amino-3-hydroxy-propionylamino)-2-hydroxy-cyclohexylsulfanyl]-acetyl}-mutilin hydrochloride and 14-O-{[(1R*,2R*,5S*)-5-((R)-2-Amino-3-hydroxy-propionylamino)-2-hydroxy-cyclohexylsulfanyl-acetyl}-mutilin hydrochloride hydrochloride Compounds of Formula I$_{EX}$, Wherein R$_{EX}$ is a Group of Formula

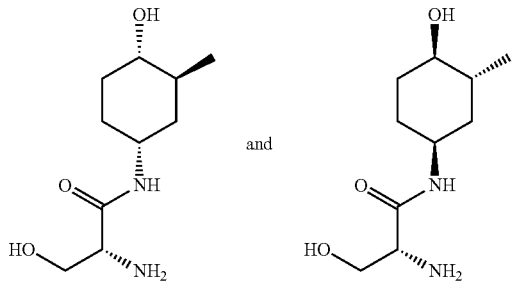

14-O-{[(1R,2R,5S)-5-Amino-2-hydroxy-cyclohexylsulfanyl]-acetyl}-mutilin+(1S,2S,5R) diastereomer (1 g, 1.97 mmol) from Example 2 is treated with (R)-2-tert-butoxycarbonylamino-3-hydroxy-propionic acid (Boc-D-serine, 404 mg, 1.97 mmol) according to the method of Example 4 Step A to C to give 14-O-{[(1S*,2S*,5R*)-5-((R)-2-amino-3-hydroxy-propionylamino)-2-hydroxy-cyclohexylsulfanyl] acetyl}-mutilin hydrochloride (a) (yield: 21 mg) and 14-O-{[(1R*,2R*,5S*)-5-((R)-2-Amino-3-hydroxy-propionylamino)-2-hydroxy-cyclohexylsulfanyl]acetyl}-mutilin hydrochloride (b) (yield: 52 mg) as colorless solids.

(a): $^1$H NMR (200 MHz, DMSO-d$_6$, δ, ppm, inter alia): 8.35 (d, 1H, NHCO, J=7 Hz), 8.15 (bs, 3H, NH$_3^+$), 6.13 (dd, 1H, 19-H, J=11 Hz and 18 Hz), 5.55 (d, 1H, 14-H, J=8 Hz), 5.06 (m, 2H, 20-H), 3.9-3.1 (m, 8H, Ser-CH$_2$OH, 22-H, 11-H, 5'-H, 2'-H, Ser-CHNH), 3.00 (m, 1H, 1'-H), 2.40 (bs, 1H, 4-H), 1.36 (s, 3H, 15-CH$_3$), 1.05 (s, 3H, 18-CH$_3$), 0.82 (d, 3H, 17-CH$_3$, J=7 Hz), 0.63 (d, 3H, 16-CH$_3$, J=6 Hz). MS-ESI (m/z): 595 (M$^+$), 640 (Mformate$^-$).

(b): $^1$H NMR (200 MHz, DMSO-d$_6$, δ, ppm, inter alia): 8.35 (d, 1H, NHCO, J=7 Hz), 8.15 (bs, 3H, NH$_3^+$), 6.13 (dd, 1H, 19-H, J=11 Hz and 18 Hz), 5.55 (d, 1H, 14-H, J=8 Hz), 5.06 (m, 2H, 20-H), 3.9-3.1 (m, 8H, Ser-CH$_2$OH, 22-H, 11-H, 5'-H, Ser-CHNH), 3.00 (m, 1H, 1'-H), 2.40 (bs, 1H, 4-H), 1.36 (s, 3H, 15-CH$_3$), 1.06 (s, 3H, 18-CH$_3$), 0.82 (d, 3H, 17-CH$_3$, J=7 Hz), 0.63 (d, 3H, 16-CH$_3$, J=6 Hz). MS-ESI (m/z): 595 (M$^+$), 639 (Mformate$^-$).

Example 21

14-O-{[(1S,2S,5R)-5-((S)-2-Amino-3-hydroxy-propionylamino)-2-hydroxy-cyclohexylsulfanyl]-acetyl}-mutilin hydrochloride+(1R,2R,5S) diastereomer hydrochloride Diastereoisomeric Mixture of Compounds of Formula I$_{EX}$, Wherein R$_{EX}$ is a Group of Formula

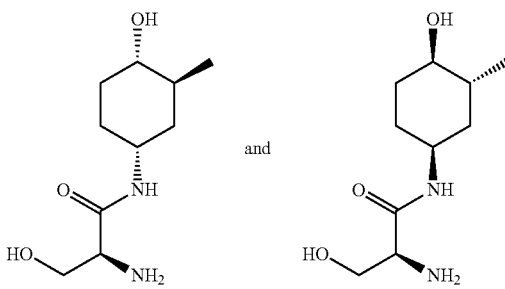

14-O-{[(1R,2R,5S)-5-Amino-2-hydroxy-cyclohexylsulfanyl]-acetyl}-mutilin+(1S,2S,5R) diastereomer (1 g, 1.97 mmol) from Example 2 is treated with (S)-2-tert-butoxycarbonylamino-3-hydroxy-propionic acid (Boc-L-serine, 404 mg, 1.97 mmol) according to the method of Example 4 Step A to C to give a mixture of 14-O-{[(1S,2S,5R)-5-((S)-2-amino-3-hydroxy-propionylamino)-2-hydroxy-cyclohexylsulfanyl]-acetyl}-mutilin hydrochloride+(1R,2R,5S) diastereomer hydrochloride (yield: 520 mg) as a colorless solid.

$^1$H NMR (200 MHz, DMSO-d$_6$, δ, ppm, inter alia): 8.38 (d, 1H, NHCO, J=7 Hz), 8.15 (bs, 3H, NH$_3^+$), 6.14 (dd, 1H, 19-H, J=11 Hz and 18 Hz), 5.54 (d, 1H, 14-H, J=7 Hz), 5.05 (m, 2H, 20-H), 4.1-3.2 (m, 8H, Ser-CH$_2$OH, 22-H, 11-H, 5'-H, 2'-H, Ser-CHNH), 3.00 (m, 1H, 1'-H), 2.40 (bs, 1H, 4-H), 1.37 (s, 3H, 15-CH$_3$), 1.06 (s, 3H, 18-CH$_3$), 0.82 (d, 3H, 17-CH$_3$, J=7 Hz), 0.63 (d, 3H, 16-CH$_3$, J=7 Hz). MS-ESI (m/z): 595 (M$^+$), 639 (Mformate$^-$).

Example 22

14-O-{[(1S*,2S*,5S*)-5-((R)-2-Amino-3-methyl-butyrylamino)-2-hydroxy-cyclohexylsulfanyl]-acetyl}-mutilin hydrochloride and 14-O-{[(1R*,2R*,5R*)-5-((R)-2-Amino-3-methyl-butyrylamino)-2-hydroxy-cyclohexylsulfanyl]-acetyl}-mutilin hydrochloride Compounds of Formula I$_{EX}$, Wherein R$_{EX}$ is a Group of Formula

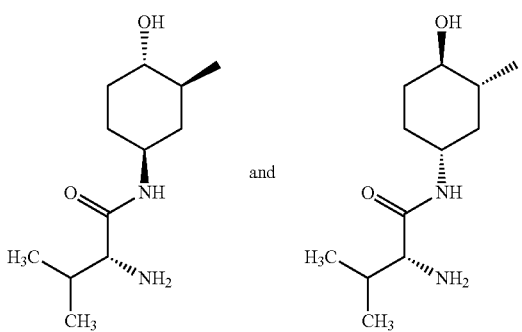

14-O-{[(1R,2R,5R)-5-Amino-2-hydroxy-cyclohexylsulfanyl]-acetyl}-mutilin+(1S,2S,5S) diastereomer (400 mg, 0.79 mmol) from Example 3 Step F is treated with (R)-2-tert-butoxycarbonylamino-3-methyl-butyric acid (Boc-D-valine, 171 mg, 0.79 mmol) according to the method of Example 4 Step A to C to give 14-O-{[(1S*,2S*,5S*)-5-((R)-2-amino-3-methyl-butyrylamino)-2-hydroxy-cyclohexylsulfanyl]-acetyl}-mutilin hydrochloride (a) (yield: 197 mg) and 14-O-{[(1R*,2R*,5R*)-5-((R)-2-amino-3-methyl-butyrylamino)-2-hydroxy-cyclohexylsulfanyl]acetyl}-mutilin hydrochloride (b) (yield: 159 mg) as colorless solids.

(a): $^1$H NMR (500 MHz, DMSO-$d_6$, δ, ppm, inter alia): 8.38 (d, 1H, NHCO, J=8 Hz), 8.12 (bs, 3H, $NH_3^+$), 6.13 (dd, 1H, 19-H, J=11 Hz and 18 Hz), 5.54 (d, 1H, 14-H, J=8 Hz), 5.05 (m, 2H, 20-H), 3.65-3.20 (m, 6H, 5'-H, 11-H, 22-H, Val-CHNH, 2'-H), 2.66 (m, 1H, 1'-H), 2.39 (bs, 1H, 4-H), 1.35 (s, 3H, 15-$CH_3$), 1.04 (s, 3H, 18-$CH_3$), 0.90 (m, 6H, 2× Val-$CH_3$), 0.81 (d, 3H, 17-$CH_3$, J=7 Hz), 0.62 (d, 3H, 16-$CH_3$, J=7 Hz). MS-ESI (m/z): 607 ($M^+$), 641 ($MCl^-$).

(b): $^1$H NMR (500 MHz, DMSO-$d_6$, δ, ppm, inter alia): 8.38 (d, 1H, NHCO, J=8 Hz), 8.13 (bs, 3H, $NH_3^+$), 6.13 (dd, 1H, 19-H, J=11 Hz and 18 Hz), 5.54 (d, 1H, 14-H, J=8 Hz), 5.05 (m, 2H, 20-H), 3.70-3.20 (m, 6H, 5'-H, 11-H, 22-H, Val-CHNH, 2'-H), 2.65 (m, 1H, 1"-H), 2.38 (bs, 1H, 4-H), 1.35 (s, 3H, 15-$CH_3$), 1.03 (s, 3H, 18-$CH_3$), 0.90 (m, 6H, 2× Val-$CH_3$), 0.81 (d, 3H, 17-$CH_3$, J=7 Hz), 0.62 (d, 3H, 16-$CH_3$, J=7 Hz). MS-ESI (m/z): 607 ($M^+$), 641 ($MCl^-$).

Example 23

14-O-{[(1S*,2S*,5S*)-5-((R)-2-Amino-propionylamino)-2-hydroxy-cyclohexylsulfanyl]-acetyl}-mutilin hydrochloride and 14-O-{[(1R*,2R*,5R*)-5-((R)-2-Amino-propionylamino)-2-hydroxy-cyclohexylsulfanyl]acetyl}-mutilin hydrochloride Compounds of Formula $I_{EX}$, Wherein $R_{EX}$ is a Group of Formula

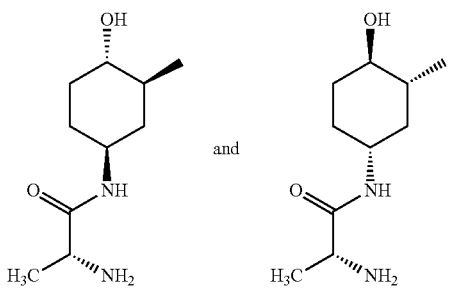

14-O-{[(1R,2R,5R)-5-Amino-2-hydroxy-cyclohexylsulfanyl]-acetyl}-mutilin+(1S,2S,5S) diastereomer (400 mg, 0.79 mmol) from Example 3 Step F is treated with (R)-2-tert-butoxycarbonylamino-propionic acid (Boc-D-alanine, 149 mg, 0.79 mmol) according to the method of Example 4 Step A to C to give 14-O-{[(1S*,2S*,5S*)-5-((R)-2-amino-propionylamino)-2-hydroxy-cyclohexylsulfanyl]acetyl}-mutilin hydrochloride (a) (yield: 116 mg) and 14-O-{[(1R*,2R*,5R*)-5-((R)-2-amino-propionylamino)-2-hydroxy-cyclohexylsulfanyl]-acetyl}-mutilin hydrochloride (b) (yield: 18 mg) as colorless solids.

(a): $^1$H NMR (500 MHz, DMSO-$d_6$, δ, ppm, inter alia): 8.3 (d, 1H, NHCO, J=8 Hz), 8.1 (bs, 3H, $NH_3^+$), 6.13 (dd, 1H, 19-H, J=11 Hz and 18 Hz), 5.54 (d, 1H, 14-H, J=8 Hz), 5.05 (m, 2H, 20-H), 3.70 (m, 1H, Ala-CHNH), 3.60-3.20 (m, 5H, 5'-H, 11-H, 22-H, 2'-H), 2.66 (m, 1H, 1'-H), 2.39 (bs, 1H, 4-H), 1.35 (s, 3H, 15-$CH_3$), 1.29 (d, 3H, Ala-$CH_3$, J=7 Hz), 1.05 (s, 3H, 18-$CH_3$), 0.81 (d, 3H, 17-$CH_3$, J=7 Hz), 0.62 (d, 3H, 16-$CH_3$, J=7 Hz). MS-ESI (m/z): 579 ($M^+$), 613 ($MCl^-$).

(b): $^1$H NMR (500 MHz, DMSO-$d_6$, δ, ppm, inter alia): 8.24 (d, 1H, NHCO, J=8 Hz), 8.03 (bs, 3H, $NH_3^+$), 6.13 (dd, 1H, 19-H, J=11 Hz and 18 Hz), 5.54 (d, 1H, 14-H, J=8 Hz), 5.05 (m, 2H, 20-H), 3.69 (m, 1H, Ala-CHNH), 3.60-3.20 (m, 5H, 5'-H, 11-H, 22-H, 2'-H), 2.64 (m, 1H, 1'-H), 2.38 (bs, 1H, 4-H), 1.35 (s, 3H, 15-$CH_3$), 1.29 (d, 3H, Ala-$CH_3$, J=7 Hz), 1.04 (s, 3H, 18-$CH_3$), 0.81 (d, 3H, 17-$CH_3$, J=7 Hz), 0.62 (d, 3H, 16-$CH_3$, J=7 Hz). MS-ESI (m/z): 579 ($M^+$), 613 ($MCl^-$).

Example 24

14-O-{[(1S*,2S*,5S*)-2-Hydroxy-5-[((R)-piperidine-2-carbonyl)-amino]-cyclohexylsulfanyl]-acetyl}-mutilin hydrochloride and 14-O-{[(1R*,2R*,5R*)-2-Hydroxy-5-[((R)-piperidine-2-carbonyl)-amino]-cyclohexylsulfanyl]-acetyl}-mutilin hydrochloride Compounds of Formula $I_{EX}$, Wherein $R_{EX}$ is a Group of Formula

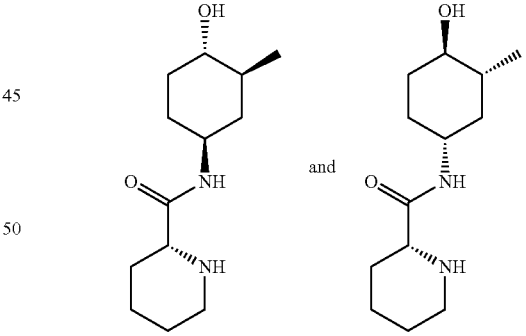

14-O-{[(1R,2R,5R)-5-Amino-2-hydroxy-cyclohexylsulfanyl]-acetyl}-mutilin+(1S,2S,5S) diastereomer (400 mg, 0.79 mmol) from Example 3 Step F is treated with (R)-1-(tert-butoxycarbonyl)-2-piperidinecarboxylic acid (Boc-D-pipecolinic acid, Boc-D-homoproline, 181 mg, 0.79 mmol) according to the method of Example 4 Step A to C to give 14-O-{[(1S*,2S*,5S*)-2-hydroxy-5-[((R)-piperidine-2-carbonyl)-amino]-cyclohexylsulfanyl]-acetyl}-mutilin hydrochloride (a) (yield: 185 mg) and 14-O-{[(1R*,2R*,5R*)-2-hydroxy-5-[((R)-piperidine-2-carbonyl)-amino]-cyclohexylsulfanyl]-acetyl}-mutilin hydrochloride (b) (yield: 162 mg) as colorless solids.

(a): $^1$H NMR (500 MHz, DMSO-d$_6$, δ, ppm, inter alia): 8.95, 8.6 (2 m, 2H, NH$_2^+$), 8.35 (d, 1H, NHCO, J=8 Hz), 6.13 (dd, 1H, 19-H, J=11 Hz and 18 Hz), 5.54 (d, 1H, 14-H, J=8 Hz), 5.05 (m, 2H, 20-H), 4.9 (bs, 1H, 2'-OH), 4.5 (bs, 1H, 11-OH), 3.65-3.20 (m, 6H, Pip-CHNH, 5'-H, 22-H, 11-H, 2'-H), 3.18, 2.87 (2 m, 2H, Pip-H), 2.67 (m, 1H, 1'-H), 2.40 (bs, 1H, 4-H), 1.35 (s, 3H, 15-CH$_3$), 1.05 (s, 3H, 18-CH$_3$), 0.81 (d, 3H, 17-CH$_3$, J=7 Hz), 0.63 (d, 3H, 16-CH$_3$, J=7 Hz). MS-ESI (m/z): 619 (M$^+$), 653 (MCl$^-$).

(b): $^1$H NMR (500 MHz, DMSO-d$_6$, δ, ppm, inter alia): 9.0, 8.6 (2 m, 2H, NH$_2^+$), 8.37 (d, 1H, NHCO, J=8 Hz), 6.13 (dd, 1H, 19-H, J=11 Hz and 18 Hz), 5.54 (d, 1H, 14-H, J=8 Hz), 5.05 (m, 2H, 20-H), 3.75-3.20 (m, 6H, Pip-CHNH, 5'-H, 22-H, 11-H, 2'-H), 3.17, 2.86 (2 m, 2H, Pip-H), 2.63 (m, 1H, 1'-H), 2.38 (bs, 1H, 4-H), 1.35 (s, 3H, 15-CH$_3$), 1.04 (s, 3H, 18-CH$_3$), 0.81 (d, 3H, 17-CH$_3$, J=7 Hz), 0.61 (d, 3H, 16-CH$_3$, J=7 Hz). MS-ESI (m/z): 619 (M$^+$), 653 (MCl$^-$).

Example 25

14-O-{[(1S,2S,5S)-5-((R)-2-Amino-3-hydroxy-propionylamino)-2-hydroxy-cyclohexylsulfanyl]-acetyl}-mutilin hydrochloride+(1R,2R,5R) diastereomer hydrochloride Diastereoisomeric Mixture of Compounds of Formula I$_{EX}$, Wherein R$_{EX}$ is a Group of Formula

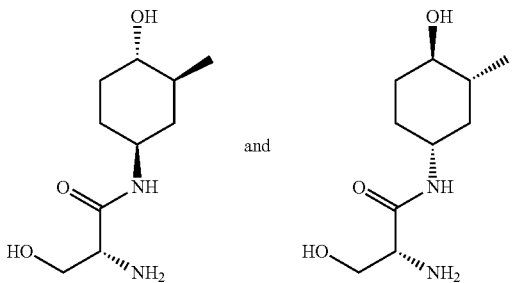

14-O-{[(1R,2R,5R)-5-Amino-2-hydroxy-cyclohexylsulfanyl]-acetyl}-mutilin+(1S,2S,5S) diastereomer (400 mg, 0.79 mmol) from Example 3 Step F is treated with (R)-2-tert-butoxycarbonylamino-3-hydroxy-propionic acid (Boc-D-serine, 161 mg, 0.79 mmol) according to the method of Example 4 Step A to C to give a mixture of 14-O-{[(1S,2S,5S)-5-((R)-2-amino-3-hydroxy-propionylamino)-2-hydroxy-cyclohexylsulfanyl]-acetyl}-mutilin hydrochloride and (1R,2R,5R) diastereomer hydrochloride (yield: 229 mg) as a colorless solid.

$^1$H NMR (500 MHz, d$_6$, δ, ppm, inter alia): 8.28 (m, 1H, NHCO), 8.04 (bs, 3H, NH$_3^+$), 6.13 (m, 1H, 19-H), 5.55 (d, 1H, 14-H, J=8 Hz), 5.42 (m, 1H, 5.05, Ser-CH$_2$OH), 5.05 (m, 2H, 20-H), 4.91 (m, 1H, 2'-OH), 4.50 (d, 1H, 11-OH, J=6 Hz), 3.75-3.20 (m, 8H, Ser-CHNH, Ser-CH$_2$OH, 5'-H, 22-H, 11-H, 2'-H), 2.64 (m, 1H, 1'-H), 2.39 (bs, 1H, 4-H), 1.35 (s, 3H, 15-CH$_3$), 1.05 (s, 3H, 18-CH$_3$), 0.81 (d, 3H, 17-CH$_3$, J=7 Hz), 0.62 (m, 3H, 16-CH$_3$). MS-ESI (m/z): 595 (M$^+$), 629 (MCl$^-$).

Example 26

14-O-[((1S,2S,4S)-4-Formylamino-2-hydroxy-cyclohexylsulfanyl)-acetyl]-mutilin+(1R,2R,4R) diastereomer Diastereoisomeric Mixture of Compounds of Formula I$_{EX}$, Wherein R$_{EX}$ is a Group of Formula

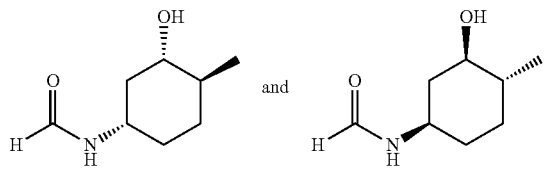

14-O-{[(1R,2R,4R)-4-Amino-2-hydroxy-cyclohexylsulfanyl]-acetyl}-mutilin+(1S,2S,4S) diastereomer (1 g, 1.97 mmol) from Example 1 Step B is treated with formic acid (0.07 mL, 1.77 mmol) according to the method of Example 4 Step A to obtain 14-O-[((1S,2S,4S)-4-formylamino-2-hydroxy-cyclohexylsulfanyl)-acetyl]-mutilin+(1R,2R,4R) diastereomer (yield: 100 mg, 11% th) as a colorless solid.

$^1$H NMR (500 MHz, DMSO-d$_6$, δ, ppm, inter alia): 7.96 (m, 1H, NHCO), 7.89 (s, 1H, CHO), 6.13 (m, 1H, 19-H), 5.55 (d, 1H, 14-H, J=8 Hz), 5.05 (m, 2H, 20-H), 4.97 (d, 1H, 2'-OH, J=5 Hz), 4.50 (d, 1H, 11-OH, J=6 Hz), 3.62 (m, 1H, 4'-H), 3.55-3.25 (m, 4H, 22-H, 11-H, 2'-H), 2.51 (m, 1H, 1'-H), 2.40 (bs, 1H, 4-H), 1.36, 1.35 (2 s, 3H, 15-CH$_3$), 1.05 (s, 3H, 18-CH$_3$), 0.81 (d, 3H, 17-CH$_3$, J=7 Hz), 0.62 (m, 3H, 16-CH$_3$). MS-ESI (m/z): 558 (MNa$^+$), 534 (M-H)$^-$, 570 (MCl$^-$).

Example 27

14-O-[((1S,2S,4S)-4-Acetylamino-2-hydroxy-cyclohexylsulfanyl)-acetyl]-mutilin+(1R,2R,4R) diastereomer Diastereoisomeric Mixture of Compounds of Formula I$_{EX}$, Wherein R$_{EX}$ is a Group of Formula

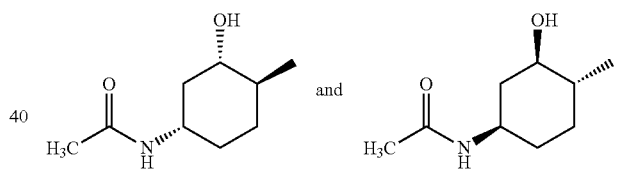

14-O-{[(1R,2R,4R)-4-Amino-2-hydroxy-cyclohexylsulfanyl]-acetyl}-mutilin+(1S,2S,4S) diastereomer (1 g, 1.97 mmol) from Example 1 Step B is treated with acetic acid (0.10 mL, 1.77 mmol) according to the method of Example 4 Step A to obtain 14-O-[((1S,2S,4S)-4-acetylamino-2-hydroxy-cyclohexylsulfanyl)-acetyl]-mutilin+(1R,2R,4R) diastereomer (yield: 842 mg, 86% th) as a colorless solid.

$^1$H NMR (500 MHz, DMSO-d$_6$, δ, ppm, inter alia): 7.72 (d, 1H, NHCO, J=8 Hz), 6.13 (m, 1H, 19-H), 5.54 (m, 1H, 14-H), 5.05 (m, 2H, 20-H), 4.94 (d, 1H, 2'-OH, J=5 Hz), 4.50 (d, 1H, 11-OH, J=6 Hz), 3.60-3.20 (m, 51-1,4'-H, 22-H, 11-H, 2'-H), 2.51 (m, 1H, 1'-H), 2.40 (bs, 1H, 4-H), 1.74 (s, 3H, COCH$_3$), 1.36, 1.35 (2 s, 3H, 15-CH$_3$), 1.05 (s, 3H, 18-CH$_3$), 0.81 (d, 3H, 17-CH$_3$, J=7 Hz), 0.62 (m, 3H, 16-CH$_3$). MS-ESI (m/z): 572 (MNa$^+$), 584 (MCl$^-$).

Example 28

14-O-[((1S,2S,4S)-2-Hydroxy-4-isobutyrylamino-cyclohexylsulfanyl)-acetyl]-mutilin+(1R,2R,4R) diastereomer Diastereoisomeric Mixture of Compounds of Formula I$_{EX}$, Wherein R$_{EX}$ is a Group of Formula

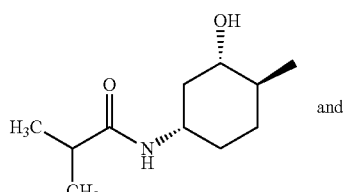

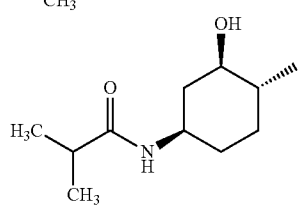

14-O-{[(1R,2R,4R)-4-Amino-2-hydroxy-cyclohexylsulfanyl]-acetyl}-mutilin+(1S,2S,4S) diastereomer (1 g, 1.97 mmol) from Example 1 Step B is treated with isobutyric acid (0.16 mL, 1.77 mmol) according to the method of Example 4 Step A to obtain 14-O-[((1S,2S,4S)-2-hydroxy-4-isobutyrylamino-cyclohexylsulfanyl)-acetyl]-mutilin+(1R,2R, 4R) diastereomer (yield: 766 mg, 75% th) as a colorless solid.

$^1$H NMR (500 MHz, DMSO-d$_6$, δ, ppm, inter alia): 7.58 (d, 1H, NHCO, J=8 Hz), 6.13 (m, 1H, 19-H), 5.54 (d, 1H, 14-H, J=8 Hz), 5.05 (m, 2H, 20-H), 4.94 (bd, 1H, 2'-OH), 4.50 (m, 1H, 11-OH), 3.60-3.20 (m, 5H, 4'-H, 22-H, 11-H, 2'-H), 2.51 (m, 1H, 1'-H), 2.40 (bs, 1H, 4-H), 1.36, 1.35 (2 s, 3H, 15-CH$_3$), 1.05 (s, 3H, 18-CH$_3$), 0.95 (m, 6H, iPr—CH$_3$), 0.81 (d, 3H, 17-CH$_3$, J=7 Hz), 0.62 (m, 3H, 16-CH$_3$). MS-ESI (m/z): 600 (MNa$^+$).

Example 29

14-O-{[(1S,2S,4S)-4-(2,2-Dimethyl-propionylamino)-2-hydroxy-cyclohexylsulfanyl]-acetyl}-mutilin+(1R,2R,4R) diastereomer Diastereoisomeric Mixture of Compounds of Formula I$_{EX}$, Wherein R$_{EX}$ is a Group of Formula

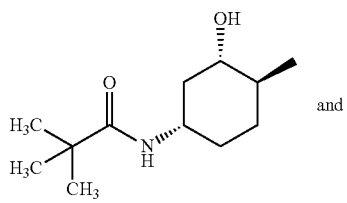

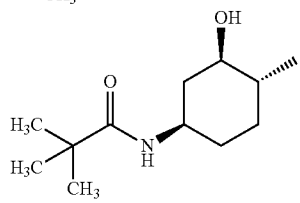

14-O-{[(1R,2R,4R)-4-Amino-2-hydroxy-cyclohexylsulfanyl]-acetyl}-mutilin+(1S,2S,4S) diastereomer (1 g, 1.97 mmol) from Example 1 Step B is treated with pivalic acid (181 mg, 1.77 mmol) according to the method of Example 4 Step A to obtain 14-O-{[(1S,2S,4S)-4-(2,2-dimethyl-propionylamino)-2-hydroxy-cyclohexylsulfanyl]acetyl}-mutilin+(1R,2R,4R) diastereomer (yield: 820 mg, 78% th) as a colorless solid.

$^1$H NMR (500 MHz, DMSO-d$_6$, δ, ppm, inter alia): 7.2 (d, 1H, NHCO, J=8 Hz), 6.13 (m, 1H, 19-H), 5.54 (d, 1H, 14-H, J=8 Hz), 5.05 (m, 2H, 20-H), 4.99 (d, 1H, 2'-OH, J=5 Hz), 4.52 (m, 1H, 11-OH), 3.58 (m, 1H, 4'-H), 3.55-3.25 (m, 4H, 22-H, 11-H, 2'-H), 2.52 (m, 1H, 1'-H), 2.40 (bs, 1H, 4-H), 1.36, 1.35 (2 s, 3H, 15-CH$_3$), 1.04 (s, 12H, 18-CH$_3$, tBu-CH$_3$), 0.81 (d, 3H, 17-CH$_3$, J=7 Hz), 0.62 (m, 3H, 16-CH$_3$). MS-ESI (m/z): 614 (MNa$^+$), 590 (M-H).

Example 30

14-O-{[(1S,2S,4S)-4-(Cyclopropanecarbonylamino)-2-hydroxy-cyclohexylsulfanyl]-acetyl}-mutilin+(1R,2R,4R) diastereomer Diastereoisomeric Mixture of Compounds of Formula I$_{EX}$, Wherein R$_{EX}$ is a Group of Formula

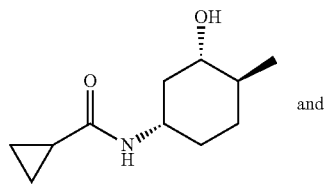

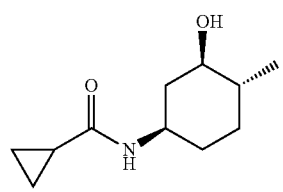

14-O-{[(1R,2R,4R)-4-Amino-2-hydroxy-cyclohexylsulfanyl]-acetyl}-mutilin+(1S,2S,4S) diastereomer (1 g, 1.97 mmol) from Example 1 Step B is treated with cyclopropanecarboxylic acid (0.14 mL, 1.77 mmol) according to the method of Example 4 Step A to obtain 14-O-{[(1S,2S,4S)-4-(cyclopropanecarbonyl-amino)-2-hydroxy-cyclohexylsulfanyl]-acetyl}-mutilin+(1R,2R,4R) diastereomer (yield: 870 mg, 85% th) as a colorless solid.

$^1$H NMR (500 MHz, DMSO-d$_6$, δ, ppm, inter alia): 7.94 (d, 1H, NHCO), 6.13 (m, 1H, 19-H), 5.54 (m, 1H, 14-H), 5.05 (m, 2H, 20-H), 4.95 (d, 1H, 2'-OH, J=5 Hz), 4.50 (d, 1H, 11-OH, J=6 Hz), 3.55 (m, 1H, 4'-H), 3.54-3.20 (m, 4H, 22-H, 11-H, 2'-H), 2.52 (m, 1H, 1'-H), 2.40 (bs, 1H, 4-H), 1.36, 1.35 (2 s, 3H, 15-CH$_3$), 1.05 (s, 3H, 18-CH$_3$), 0.81 (d, 3H, 17-CH$_3$, J=7 Hz), 0.65-0.55 (m, 7H, 16-CH$_3$, cPr—CH$_2$). MS-ESI (m/z): 598 (MNa$^+$), 574 (M-H) 610 (MCl$^-$).

Example 31

14-O-[((1S,2S,5R)-5-Formylamino-2-hydroxy-cyclohexylsulfanyl)-acetyl]-mutilin+(1R,2R,5S) diastereomer Diastereoisomeric Mixture of Compounds of Formula I$_{EX}$, Wherein R$_{EX}$ is a Group of Formula 14-O-{[(1R,2R,5S)-5-Amino-2-hydroxy-cyclohexylsulfanyl]-acetyl}-mutilin+(1S,2S,5R) diastereomer (2 g, 3.94 mmol) from Example 2 is treated with acetic formic anhydride (0.50 mL, 3.55 mmol) according to the method of Example 4 Step A to obtain 14-O-[((1S,2S,5R)-5-formylamino-2-hydroxy-cyclohexylsulfanyl)-acetyl]-mutilin+(1R,2R,5S) diastereomer (yield: 1.53 g, 81% th) as a colorless solid.

$^1$H NMR (500 MHz, DMSO-d$_6$, δ, ppm, inter alia): 7.99 (m, 1H, NHCO), 7.90 (s, 1H, CHO), 6.13 (dd, 1H, 19-H, J=11 and 18 Hz), 5.54 (d, 1H, 14-H, J=8 Hz), 5.04 (m, 2H, 20-H), 4.90 (m, 1H, 2'-OH), 4.49 (d, 1H, 11-OH, J=6 Hz), 3.83 (m, 1H, 5'-H), 3.54 (m, 1H, 2'-H), 3.45-3.20 (m, 3H, 22-H, 11-H), 2.94 (m, 1H, 1'-H), 2.39 (bs, 1H, 4-H), 1.36, 1.35 (2 s, 3H, 15-CH$_3$), 1.05 (s, 3H, 18-CH$_3$), 0.81 (d, 3H, 17-CH$_3$, J=7 Hz), 0.62 (m, 3H, 16-CH$_3$). MS-ESI (m/z): 558 (MNa$^+$), 534 (M-H) 570 (MCl$^-$).

Example 32

14-O-[((1S,2S,5R)-5-Formylamino-2-formyloxy-cyclohexylsulfanyl)-acetyl]-mutilin+(1R,2R,5S) diastereomer Diastereoisomeric Mixture of Compounds of Formula I$_{EX}$, Wherein R$_{EX}$ is a Group of Formula To a solution of 14-O-{[(1R,2R,5S)-5-amino-2-hydroxy-cyclohexylsulfanyl]-acetyl}-mutilin+(1S,2S,5R) diastereomer (2 g, 3.94 mmol) from Example 2 in 15 mL of CH$_2$Cl$_2$ is added acetic formic anhydride (0.55 mL, 3.94 mmol), N-ethyldiisopropylamine (1.45 mL, 7.88 mmol), and 4-dimethylamino-pyridine (96 mg, 0.79 mmol) and stirred at RT overnight. The reaction mixture is charged with brine and extracted with EtOAc. The organic layers are dried over Na$_2$SO$_4$ and filtered. The filtrate is concentrated under reduced pressure and subjected to chromatography (silica, cHex/EtOAc=1/5) to obtain 14-O-[((1S,2S,5R)-5-formylamino-2-formyloxy-cyclohexylsulfanyl)-acetyl]-mutilin and (1R,2R,5S) diastereomer (R$_f$=0.24; yield: 510 mg, 46% th) as a colorless solid.

$^1$H NMR (500 MHz, DMSO-d$_6$, δ, ppm, inter alia): 8.25 (s, 1H, CHO), 8.12 (m, 1H, NHCO), 7.94 (s, 1H, CHO), 6.11 (dd, 1H, 19-H, J=11 and 18 Hz), 5.53 (d, 1H, 14-H, J=8 Hz), 5.04 (m, 2H, 20-H), 4.83 (m, 1H, 2'-H), 4.50 (d, 1H, 11-OH, J=6 Hz), 3.87 (m, 1H, 5'-H), 3.45-3.25 (m, 3H, 22-H, 11-H), 3.14 (m, 1H, 1'-H), 2.39 (bs, 1H, 4-H), 1.34 (s, 3H, 15-CH$_3$), 1.05 (s, 3H, 18-CH$_3$), 0.81 (d, 3H, 17-CH$_3$, J=7 Hz), 0.60 (d, 3H, 16-CH$_3$, J=7 Hz). MS-ESI (m/z): 586 (MNa$^+$), 562 (M-H)$^-$.

Example 33

14-O-[((1S,2S,5R)-5-Acetylamino-2-hydroxy-cyclohexylsulfanyl)-acetyl]-mutilin+(1R,2R,5S) diastereomer Diastereoisomeric Mixture of Compounds of Formula I$_{EX}$, Wherein R$_{EX}$ is a Group of Formula 14-O-{[(1R,2R,5S)-5-Amino-2-hydroxy-cyclohexylsulfanyl]-acetyl}-mutilin+(1S,2S,5R) diastereomer (2 g, 3.94 mmol) from Example 2 is treated with acetic anhydride (0.34 mL, 3.55 mmol) according to the method of Example 4 Step A to obtain 14-O-[((1S,2S,5R)-5-acetylamino-2-hydroxy-cyclohexylsulfanyl)-acetyl]-mutilin+(1R,2R,5S) diastereomer (yield: 1.56 g, 80% th) as a colorless solid.

$^1$H NMR (500 MHz, DMSO-d$_6$, δ, ppm, inter alia): 7.69 (m, 1H, NHCO), 6.12 (dd, 1H, 19-H, J=11 and 18 Hz), 5.53 (d, 1H, 14-H, J=8 Hz), 5.05 (m, 2H, 20-H), 4.87 (m, 1H, 2'-OH), 4.49 (d, 1H, 11-OH, J=6 Hz), 3.73 (m, 1H, 5'-H), 3.54 (m, 1H, 2'-H), 3.45-3.25 (m, 3H, 22-H, 11-H), 2.96 (m, 1H, 1'-H), 2.39 (bs, 1H, 4-H), 1.75 (s, 3H, COCH$_3$), 1.36, 1.35 (2 s, 3H, 15-CH$_3$), 1.04 (s, 3H, 18-CH$_3$), 0.81 (d, 3H, 17-CH$_3$, J=7 Hz), 0.62 (m, 3H, 16-CH$_3$). MS-ESI (m/z): 572 (MNa$^+$), 548 (M-H)$^-$, 584 (MCl$^-$).

Example 34

14-O-[((1S,2S,5R)-2-Acetoxy-5-acetylamino-cyclohexylsulfanyl)-acetyl]-mutilin+(1R,2R,5S) diastereomer Diastereoisomeric Mixture of Compounds of Formula I$_{EX}$, Wherein R$_{EX}$ is a Group of Formula

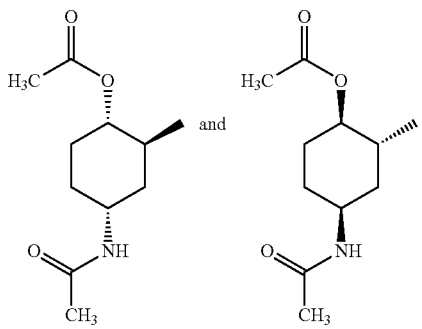

14-O-{[(1R,2R,5S)-5-Amino-2-hydroxy-cyclohexylsulfanyl]-acetyl}-mutilin+(1S,2S,5R) diastereomer (2 g, 3.94 mmol) from Example 2 is treated with acetic anhydride (0.38 mL, 3.94 mmol) according to the method of Example 32 to obtain 14-O-[((1S,2S,5R)-2-acetoxy-5-acetylamino-cyclohexylsulfanyl)-acetyl]-mutilin+(1R,2R,5S) diastereomer (yield: 918 mg, 79% th) as a colorless solid.

$^1$H NMR (500 MHz, DMSO-d$_6$, δ, ppm, inter alia): 7.77 (m, 1H, NHCO), 6.11 (dd, 1H, 19-H, J=11 and 18 Hz), 5.53 (d, 1H, 14-H, J=8 Hz), 5.03 (m, 2H, 20-H), 4.72 (m, 1H, 2'-H), 4.49 (d, 1H, 11-OH, J=6 Hz), 3.77 (m, 1H, 5'-H), 3.45-3.25 (m, 3H, 22-H, 11-H), 3.13 (m, 1H, 1'-H), 2.39 (bs, 1H, 4-H), 2.00 (s, 3H, COCH$_3$), 1.77 (s, 3H, COCH$_3$), 1.35 (s, 3H, 15-CH$_3$), 1.05 (s, 3H, 18-CH$_3$), 0.81 (d, 3H, 17-CH$_3$, J=7 Hz), 0.61 (d, 3H, 16-CH$_3$, J=7 Hz). MS-ESI (m/z): 614 (MNa$^+$), 590 (M-H)$^-$, 626 (MCl$^-$).

Example 35

14-O-[((1S,2S,5R)-2-Hydroxy-5-isobutyrylamino-cyclohexylsulfanyl)-acetyl]-mutilin+(1R,2R,5S) diastereomer Diastereoisomeric Mixture of Compounds of Formula I$_{EX}$, Wherein R$_{EX}$ is a Group of Formula

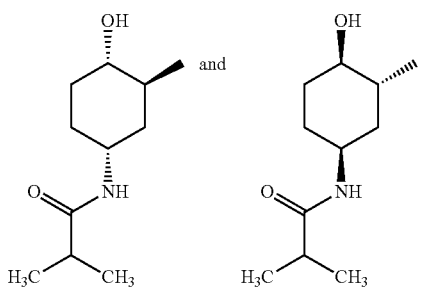

14-O-{[(1R,2R,5S)-5-Amino-2-hydroxy-cyclohexylsulfanyl]-acetyl}-mutilin+(1S,2S,5R) diastereomer (2 g, 3.94 mmol) from Example 2 is treated with isobutyryl chloride (0.42 mL, 3.94 mmol) according to the method of Example 32 to obtain 14-O-[((1S,2S,5R)-2-hydroxy-5-isobutyrylamino-cyclohexylsulfanyl)-acetyl]-mutilin+(1R,2R,5S) diastereomer (yield: 1.16 g, 51% th) as a colorless solid.

$^1$H NMR (500 MHz, DMSO-d$_6$, δ, ppm, inter alia): 7.53 (m, 1H, NHCO), 6.12 (dd, 1H, 19-H, J=11 and 18 Hz), 5.53 (d, 1H, 14-H, J=8 Hz), 5.04 (m, 2H, 20-H), 4.86 (m, 1H, 2'-OH), 4.49 (d, 1H, 11-OH, J=6 Hz), 3.71 (m, 1H, 5'-H), 3.55 (m, 1H, 2'-H), 3.45-3.25 (m, 3H, 22-H, 11-H), 2.99 (m, 1H, 1'-H), 2.39 (bs, 1H, 4-H), 1.36, 1.35 (2 s, 3H, 15-CH$_3$), 1.04 (s, 3H, 18-CH$_3$), 0.95 (m, 6H, iPr—CH$_3$), 0.81 (d, 3H, 17-CH$_3$, J=7 Hz), 0.62 (m, 3H, 16-CH$_3$). MS-ESI (m/z): 600 (MNa$^+$), 576 (M-H)$^-$, 612 (MCl$^-$).

Example 36

14-O-{[(1S,2S,5R)-5-(2,2-Dimethyl-propionylamino)-2-hydroxy-cyclohexylsulfanyl]-acetyl}-mutilin+(1R,2R,5S) diastereomer Diastereoisomeric Mixture of Compounds of Formula I$_{EX}$, Wherein R$_{EX}$ is a Group of Formula

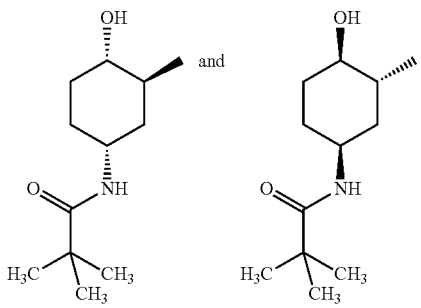

14-O-{[(1R,2R,5S)-5-Amino-2-hydroxy-cyclohexylsulfanyl]-acetyl}-mutilin+(1S,2S,5R) diastereomer (2 g, 3.94 mmol) from Example 2 is treated with pivaloyl chloride (0.48 mL, 3.94 mmol) according to the method of Example 32 to obtain 14-O-{[(1S,2S,5R)-5-(2,2-dimethyl-propionylamino)-2-hydroxy-cyclohexylsulfanyl]acetyl}-mutilin+(1R,2R,5S) diastereomer (yield: 850 mg, 37% th) as a colorless solid.

$^1$H NMR (500 MHz, DMSO-d$_6$, δ, ppm, inter alia): 7.03 (m, 1H, NHCO), 6.13 (dd, 1H, 19-H, J=11 and 18 Hz), 5.53 (d, 1H, 14-H, J=8 Hz), 5.05 (m, 2H, 20-H), 4.86 (m, 1H, 2-OH), 4.49 (d, 1H, 11-OH, J=6 Hz), 3.74 (m, 1H, 5'-H), 3.63 (m, 1H, 2'-H), 3.45-3.20 (m, 3H, 22-H, 11-H), 3.03 (m, 1H, 1'-H), 2.39 (bs, 1H, 4-H), 1.35 (s, 3H, 15-CH$_3$), 1.04 (s, 12H, 18-CH$_3$, tBu-CH$_3$), 0.81 (d, 3H, 17-CH$_3$, J=7 Hz), 0.62 (m, 3H, 16-CH$_3$). MS-ESI (m/z): 614 (MNa$^+$), 590 (M-H)$^-$, 626 (MCl$^-$).

Example 37

14-O-{[(1S,2S,5R)-5-(Cyclopropanecarbonylamino)-2-hydroxy-cyclohexylsulfanyl]-acetyl}-mutilin+(1R,2R,5S) diastereomer Diastereoisomeric Mixture of Compounds of Formula I$_{EX}$, Wherein R$_{EX}$ is a Group of Formula

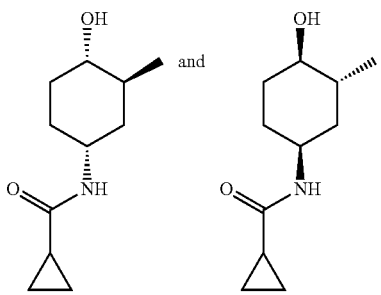

14-O-{[(1R,2R,5S)-5-Amino-2-hydroxy-cyclohexylsulfanyl]-acetyl}-mutilin+(1S,2S,5S) diastereomer (2 g, 3.94 mmol) from Example 2 is treated with cyclopropanecarbonyl chloride (0.36 mL, 3.94 mmol) according to the method of Example 32 to obtain 14-O-{[(1S,2S,5R)-5-(cyclopropanecarbonyl-amino)-2-hydroxy-cyclohexylsulfanyl]acetyl}-mutilin+(1R,2R,5S) diastereomer (yield: 1.23 g, 54% th) as a colorless solid.

$^1$H NMR (500 MHz, DMSO-$d_6$, δ, ppm, inter alia): 7.90 (m, 1H, NHCO), 6.12 (dd, 1H, 19-H, J=11 and 18 Hz), 5.53 (m, 1H, 14-H), 5.05 (m, 2H, 20-H), 4.88 (m, 1H, 2'-OH), 4.49 (d, 1H, 11-OH, J=6 Hz), 3.76 (m, 1H, 5'-H), 3.55 (m, 1H, 2'-H), 3.45-3.25 (m, 3H, 22-H, 11-H), 2.99 (m, 1H, 1'-H), 2.39 (bs, 1H, 4-H), 1.35, 1.34 (2 s, 3H, 15-CH$_3$), 1.04 (s, 3H, 18-CH$_3$), 0.81 (d, 3H, 17-CH$_3$, J=7 Hz), 0.65-0.55 (m, 7H, 16-CH$_3$, cPr—CH$_2$). MS-ESI (m/z): 598 (MNa$^+$), 574 (M-H)$^-$, 610 (MCl$^-$).

Example 38

14-O-[((1S,2S,5S)-5-Formylamino-2-hydroxy-cyclohexylsulfanyl)-acetyl]-mutilin+(1R,2R,5R) diastereomer Diastereoisomeric Mixture of Compounds of Formula I$_{EX}$, Wherein R$_{EX}$ is a Group of Formula

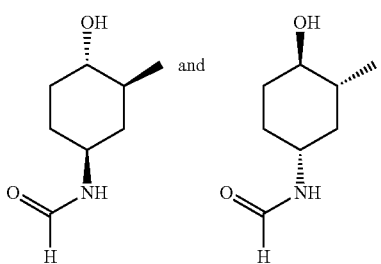

14-O-{[(1R,2R,5R)-5-Amino-2-hydroxy-cyclohexylsulfanyl]-acetyl}-mutilin+(1S,2S,5S) diastereomer (400 mg, 0.79 mmol) from Example 3 Step F is treated with formic acid (0.03 mL, 0.79 mmol) according to the method of Example 4 Step A to obtain 14-O-[((1S,2S,5S)-5-formylamino-2-hydroxy-cyclohexylsulfanyl)-acetyl]-mutilin+(1R,2R,5R) diastereomer (yield: 28 mg, 7% th) as a colorless solid.

$^1$H NMR (400 MHz, DMSO-$d_6$, δ, ppm, inter alia): 7.95-7.85 (m, 2H, NHCO, CHO), 6.13 (dd, 1H, 19-H, J=11 Hz and 18 Hz), 5.54 (m, 1H, 14-H), 5.05 (m, 2H, 20-H), 4.86 (m, 1H, 2'-OH), 4.47 (m, 1H, 11-OH), 3.65-3.15 (m, 5H, 5'-H, 22-H, 11-H, 2'-H), 2.63 (m, 1H, 1''-H), 2.39 (bs, 1H, 4-H), 1.36, 1.35 (2 s, 3H, 15-CH$_3$), 1.06 (s, 3H, 18-CH$_3$), 0.82 (d, 3H, 17-CH$_3$, J=7 Hz), 0.63 (d, 3H, 16-CH$_3$, J=7 Hz). MS-ESI (m/z): 558 (MNa$^+$), 570 (MCl$^-$).

Example 39

14-O-[((1S,2S,5S)-5-Acetylamino-2-hydroxy-cyclohexylsulfanyl)-acetyl]-mutilin+(1R,2R,5R) diastereomer Diastereoisomeric Mixture of Compounds of Formula I$_{EX}$, Wherein R$_{EX}$ is a Group of Formula

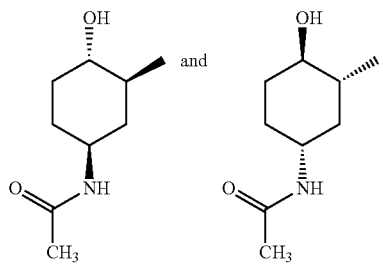

14-O-{[(1R,2R,5R)-5-Amino-2-hydroxy-cyclohexylsulfanyl]-acetyl}-mutilin+(1S,2S,5S) diastereomer (400 mg, 0.79 mmol) from Example 3 Step F is treated with acetic acid (0.045 mL, 0.79 mmol) according to the method of Example 4 Step A to obtain 14-O-[((1S,2S,5S)-5-acetylamino-2-hydroxy-cyclohexylsulfanyl)-acetyl]-mutilin+(1R,2R,5R) diastereomer (yield: 390 mg, 90% th) as a colorless solid.

$^1$H NMR (400 MHz, DMSO-$d_6$, δ, ppm, inter alia): 7.66 (d, 1H, NHCO, J=8 Hz), 6.13 (dd, 1H, 19-H, J=11 Hz and 18 Hz), 5.54 (d, 1H, 14-H, J=8 Hz), 5.05 (m, 2H, 20-H), 4.84 (m, 1H, 2'-OH), 4.47 (m, 1H, 11-OH), 3.55-3.15 (m, 5H, 5'-H, 22-H, 11-H, 2'-H), 2.63 (m, 1H, 1'-H), 2.39 (bs, 1H, 4-H), 1.74 (s, 3H, COCH$_3$), 1.36, 1.35 (2 s, 3H, 15-CH$_3$), 1.05 (s, 3H, 18-CH$_3$), 0.82 (d, 3H, 17-CH$_3$, J=7 Hz), 0.63 (m, 3H, 16-CH$_3$). MS-ESI (m/z): 572 (MNa$^+$), 584 (MCl$^-$).

Example 40

14-O-[((1S,2S,5S)-2-Hydroxy-5-isobutyrylamino-cyclohexylsulfanyl)-acetyl]-mutilin+(1R,2R,5R) diastereomer Diastereoisomeric Mixture of Compounds of Formula I$_{EX}$, Wherein R$_{EX}$ is a Group of Formula

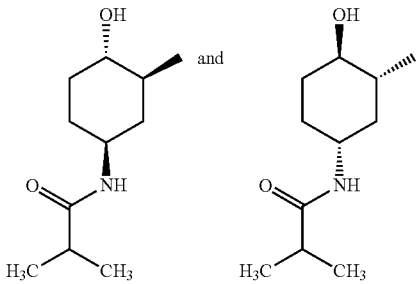

14-O-{[(1R,2R,5R)-5-Amino-2-hydroxy-cyclohexylsulfanyl]-acetyl}-mutilin+(1S,2S,5S) diastereomer (400 mg, 0.79 mmol) from Example 3 Step F is treated with isobutyric acid (0.073 mL, 0.79 mmol) according to the method of Example 4 Step A to obtain 14-O-[((1S,2S,5S)-2-hydroxy-5-isobutyrylamino-cyclohexylsulfanyl)-acetyl]-mutilin+(1R,2R,5R) diastereomer (yield: 339 mg, 74% th) as a colorless solid.

¹H NMR (400 MHz, DMSO-d₆, δ, ppm, inter alia): 7.51 (m, 1H, NHCO), 6.13 (dd, 1H, 19-H, J=11 Hz and 18 Hz), 5.54 (d, 1H, 14-H, J=8 Hz), 5.05 (m, 2H, 20-H), 4.84 (m, 1H, 2'-OH), 4.47 (m, 1H, 11-OH), 3.55-3.15 (m, 5H, 5'-H, 22-H, 11-H, 2'-H), 2.63 (m, 1H, 1'-H), 2.39 (bs, 1H, 4-H), 1.36, 1.35 (2 s, 3H, 15-CH₃), 1.05 (s, 3H, 18-CH₃), 0.95 (m, 6H, iPr—CH₃), 0.81 (d, 3H, 17-CH₃, J=7 Hz), 0.62 (m, 3H, 16-CH₃). MS-ESI (m/z): 600 (MNa⁺), 612 (MCl⁻).

Example 41

14-O-{[(1S,2S,5S)-5-(2,2-Dimethyl-propionylamino)-2-hydroxy-cyclohexylsulfanyl]-acetyl}-mutilin+(1R,2R,5R) diastereomer Diastereoisomeric Mixture of Compounds of Formula $I_{EX}$, Wherein $R_{EX}$ is a Group of Formula

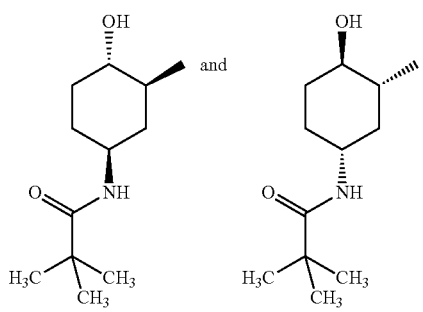

14-O-{[(1R,2R,5R)-5-Amino-2-hydroxy-cyclohexylsulfanyl]-acetyl}-mutilin+(1S,2S,5S) diastereomer (400 mg, 0.79 mmol) from Example 3 Step F is treated with pivalic acid (0.091 mL, 0.79 mmol) according to the method of Example 4 Step A to obtain 14-O-{[(1S,2S,5S)-5-(2,2-dimethyl-propionylamino)-2-hydroxy-cyclohexylsulfanyl]-acetyl}-mutilin+(1R,2R,5R) diastereomer (yield: 245 mg, 52% th) as a colorless solid.

¹H NMR (400 MHz, DMSO-d₆, δ, ppm, inter alia): 7.07 (m, 1H, NHCO), 6.13 (m, 1H, 19-H), 5.54 (d, 1H, 14-H, J=8 Hz), 5.05 (m, 2H, 20-H), 4.83 (m, 1H, 2'-OH), 4.47 (m, 1H, 11-OH), 3.60-3.15 (m, 5H, 5'-H, 22-H, 11-H, 2'-H), 2.63 (m, 1H, 1'-H), 2.39 (bs, 1H, 4-H), 1.36, 1.35 (2 s, 3H, 15-CH₃), 1.05 (s, 12H, 18-CH₃, tBu-CH₃), 0.82 (d, 3H, 17-CH₃, J=7 Hz), 0.63 (m, 3H, 16-CH₃). MS-ESI (m/z): 614 (MNa⁺), 590 (M-H)⁻, 626 (MCl⁻).

Example 42

14-O-{[(1S,2S,5S)-5-(Cyclopropanecarbonyl-amino)-2-hydroxy-cyclohexylsulfanyl]acetyl}-mutilin+(1R,2R,5R) diastereomer Diastereoisomeric Mixture of Compounds of Formula $I_{EX}$, Wherein $R_{EX}$ is a Group of Formula

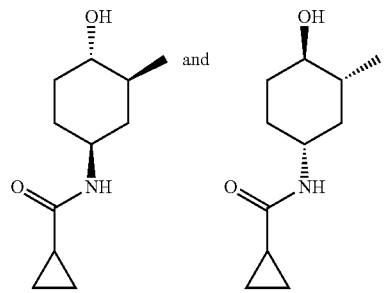

14-O-{[(1R,2R,5R)-5-Amino-2-hydroxy-cyclohexylsulfanyl]acetyl}-mutilin+(1S,2S,5S) diastereomer (400 mg, 0.79 mmol) from Example 3 Step F is treated with cyclopropanecarboxylic acid (0.063 mL, 0.79 mmol) according to the method of Example 4 Step A to obtain 14-O-{[(1S,2S,5S)-5-(cyclopropanecarbonyl-amino)-2-hydroxy-cyclohexylsulfanyl]acetyl}-mutilin+(1R,2R,5R) diastereomer (yield: 386 mg, 85% th) as a colorless solid.

¹H NMR (400 MHz, DMSO-d₆, δ, ppm, inter alia): 7.87 (m, 1H, NHCO), 6.13 (m, 1H, 19-H), 5.54 (d, 1H, 14-H, J=8 Hz), 5.05 (m, 2H, 20-H), 4.83 (m, 1H, 2'-OH), 4.47 (m, 1H, 11-OH), 3.60-3.15 (m, 5H, 5'-H, 22-H, 11-H, 2'-H), 2.62 (m, 1H, 1'-H), 2.38 (bs, 1H, 4-H), 1.36, 1.35 (2 s, 3H, 15-CH₃), 1.05 (s, 3H, 18-CH₃), 0.82 (d, 3H, 17-CH₃, J=7 Hz), 0.65-0.55 (m, 7H, 16-CH₃, cPr—CH₂). MS-ESI (m/z): 598 (MNa⁺), 574 (M-H)⁻, 610 (MCl⁻).

The invention claimed is:

1. A compound of formula I

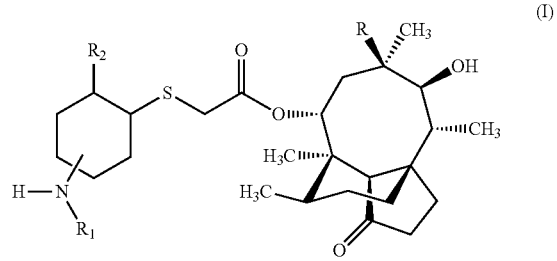

wherein
R is ethyl or vinyl;
$R_1$ is a group of formula

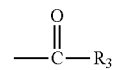

$R_2$ is OH or $OR_1$; and
$R_3$ is hydrogen, straight chain or branched $(C_{1-8})$alkyl or $(C_{3-8})$cycloalkyl, or
is that part of an natural amino acid in D or in L form which remains if the carboxylic acid group is split off, or
is that part of an non natural amino acid in D or in L form which remains if the carboxylic acid group is split off.

2. A compound according to claim 1, wherein R is vinyl.

3. A compound according to claim 1 of formula $I_{PREF1}$

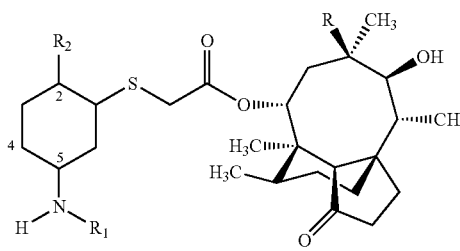

4. A compound according to claim 1 of formula I<sub>PREF2</sub>

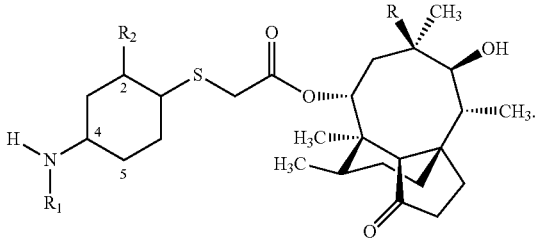

5. A compound according to claim 1, wherein $R_2$ is hydroxy.

6. A compound according to claim 1, wherein $R_3$ is hydrogen,
($C_{3-6}$)cycloalkyl, aliphatic or aromatic heterocyclyl comprising 5 to 6 ring members and 1 to 4 heteroatoms selected from N, O and or S, with the proviso that at least one heteroatom is N, or straight chain or branched ($C_{1-6}$)alkyl, wherein alkyl is unsubstituted or substituted by amino and optionally further substituted by
hydroxy, guanidino, aminocarbonyl, carboxy, mercapto, ($C_{1-4}$)alkylmercapto, phenyl, hydroxyphenyl, seleno, amino, which amino optionally is substituted by heterocyclylcarbonyl, wherein heterocyclyl includes aromatic and aliphatic heterocyclyl 5 to 6 ring members and 1 to 4 heteroatoms selected from N, O and/or S; or
aromatic or aliphatic heterocyclyl, comprising 5 to 6 ring members and comprising 1 to 4 heteroatoms selected from N, O and/or S, which heterocyclyl optionally is fused with phenyl.

7. A compound according to claim 6, wherein $R_3$ is hydrogen, ($C_{3-6}$)cycloalkyl, aliphatic heterocyclyl comprising 5 or 6 ring members and at least one nitrogen atom, or straight chain or branched ($C_{1-6}$)alkyl substituted by amino and optionally further substituted by hydroxy.

8. A compound according to claim 1, selected from the group consisting of:
14-O-{[(1S,2S,4S)-4-((R)-2-Amino-3-methyl-butyrylamino)-2-hydroxy-cyclohexylsulfanyl]-acetyl}-mutilin,
14-O-{[(1R,2R,4R)-4-((R)-2-Amino-3-methyl-butyrylamino)-2-hydroxy-cyclohexylsulfanyl]-acetyl}-mutilin,
14-O-{[(1S,2S,4S)-4-((S)-2-Amino-3-methyl-butyrylamino)-2-hydroxy-cyclohexylsulfanyl]-acetyl}-mutilin,
14-O-{[(1R,2R,4R)-4-((S)-2-Amino-3-methyl-butyrylamino)-2-hydroxy-cyclohexylsulfanyl]-acetyl}-mutilin,
14-O-{[(1S,2S,4S)-4-((R)-2-Amino-propionylamino)-2-hydroxy-cyclohexylsulfanyl]-acetyl}-mutilin,
14-O-{[(1R,2R,4R)-4-((R)-2-Amino-propionylamino)-2-hydroxy-cyclohexylsulfanyl]-acetyl}-mutilin,
14-O-{[(1S,2S,4S)-4-((S)-2-Amino-propionylamino)-2-hydroxy-cyclohexylsulfanyl]-acetyl}-mutilin,
14-O-{[(1R,2R,4R)-4-((R)-2-Amino-propionylamino)-2-hydroxy-cyclohexylsulfanyl]-acetyl}-mutilin,
14-O-{[(1S,2S,4S)-2-Hydroxy-4-[((R)-piperidine-2-carbonyl)-amino]-cyclohexylsulfanyl]-acetyl}-mutilin,
14-O-{[(1R,2R,4R)-2-Hydroxy-4-[((R)-piperidine-2-carbonyl)-amino]-cyclohexylsulfanyl]-acetyl}-mutilin,
14-O-{[(1S,2S,4S)-2-Hydroxy-4-[((S)-piperidine-2-carbonyl)-amino]-cyclohexylsulfanyl]-acetyl}-mutilin,
14-O-{[(1R,2R,4R)-2-Hydroxy-4-[((S)-piperidine-2-carbonyl)-amino]-cyclohexylsulfanyl]-acetyl}-mutilin,
14-O-{[(1S,2S,4S)-4-((R)-2-Amino-3-hydroxy-propionylamino)-2-hydroxy-cyclohexylsulfanyl]-acetyl}-mutilin and the (1R,2R,4R) diastereomer thereof,
14-O-{[(1S,2S,5R)-5-((R)-2-Amino-3-methyl-butyrylamino)-2-hydroxy-cyclohexylsulfanyl]-acetyl}-mutilin,
14-O-{[(1R,2R,5S)-5-((R)-2-Amino-3-methyl-butyrylamino)-2-hydroxy-cyclohexylsulfanyl]-acetyl}-mutilin,
14-O-{[(1S,2S,5R)-5-((S)-2-Amino-3-methyl-butyrylamino)-2-hydroxy-cyclohexylsulfanyl]-acetyl}-mutilin,
14-O-{[(1R,2R,5S)-5-((S)-2-Amino-3-methyl-butyrylamino)-2-hydroxy-cyclohexylsulfanyl]-acetyl}-mutilin,
14-O-{[(1S,2S,5R)-5-((S)-2-Amino-3-methyl-butyrylamino)-2-hydroxy-cyclohexylsulfanyl]-acetyl}-19,20-dihydro-mutilin,
14-O-{[(1R,2R,5S)-5-((S)-2-Amino-3-methyl-butyrylamino)-2-hydroxy-cyclohexylsulfanyl]-acetyl}-19,20-dihydro-mutilin,
14-O-{[(1S,2S,5R)-5-((R)-2-Amino-propionylamino)-2-hydroxy-cyclohexylsulfanyl]-acetyl}-mutilin,
14-O-{[(1R,2R,5S)-5-((R)-2-Amino-propionylamino)-2-hydroxy-cyclohexylsulfanyl]-acetyl}-mutilin,
14-O-{[(1S,2S,5R)-5-((S)-2-Amino-propionylamino)-2-hydroxy-cyclohexylsulfanyl]-acetyl}-mutilin and the (1R,2R,5S) diastereomer thereof,
14-O-{[(1S,2S,5R)-2-Hydroxy-5-[((R)-piperidine-2-carbonyl)-amino]-cyclohexylsulfanyl]-acetyl}-mutilin,
14-O-{[(1R,2R,5S)-2-Hydroxy-5-[((R)-piperidine-2-carbonyl)-amino]-cyclohexylsulfanyl]-acetyl}-mutilin,
14-O-{[(1S,2S,5R)-2-Hydroxy-5-[((R)-piperidine-2-carbonyl)-amino]-cyclohexylsulfanyl]-acetyl}-19,20-dihydro-mutilin,
14-O-{[(1R,2R,5S)-2-Hydroxy-5-[((R)-piperidine-2-carbonyl)-amino]-cyclohexylsulfanyl]-acetyl}-19,20-dihydro-mutilin,
14-O-{[(1S,2S,5R)-2-Hydroxy-5-[((S)-piperidine-2-carbonyl)-amino]-cyclohexylsulfanyl]-acetyl}-mutilin,
14-O-{[(1R,2R,5S)-2-Hydroxy-5-[((S)-piperidine-2-carbonyl)-amino]-cyclohexylsulfanyl]-acetyl}-mutilin,
14-O-{[(1S,2S,5R)-2-Hydroxy-5-[((S)-piperidine-2-carbonyl)-amino]-cyclohexylsulfanyl]-acetyl}-19,20-dihydro-mutilin,
14-O-{[(1R,2R,5S)-2-Hydroxy-5-[((S)-piperidine-2-carbonyl)-amino]-cyclohexylsulfanyl]-acetyl}-19,20-dihydro-mutilin,
14-O-{[(1S,2S,5R)-5-((R)-2-Amino-3-hydroxy-propionylamino)-2-hydroxy-cyclohexylsulfanyl]-acetyl}-mutilin, 14-O-{[(1R,2R,5S)-5-((R)-2-Amino-3-hydroxy-propionylamino)-2-hydroxy-cyclohexylsulfanyl]-acetyl}-mutilin, 14-O-{[(1S,2S,5R)-5-((S)-2-Amino-3-hydroxy-propionylamino)-2-hydroxy-cyclohexylsulfanyl]-acetyl}-mutilin and the (1R,2R,5S) diastereomer thereof, 14-O-{[(1S,2S,5S)-5-((R)-2-Amino-3-methyl-butyrylamino)-2-hydroxy-cyclohexylsulfanyl]-acetyl}-mutilin, 14-O-{[(1R,2R,5R)-5-((R)-2-Amino-3-methyl-butyrylamino)-2-hydroxy-cyclohexylsulfanyl]-acetyl}-mutilin, 14-O-{[(1S,2S,5S)-5-((R)-2-Amino-propionylamino)-2-hydroxy-cyclohexylsulfanyl]-acetyl}-mutilin, 14-O-{[(1R,2R,5R)-5-((R)-2-Amino-propionylamino)-2-hydroxy-cyclohexylsulfanyl]-acetyl}-mutilin, 14-O-{[(1S,2S,5S)-2-Hydroxy-5-[((R)-piperidine-2-carbonyl)-amino]-cyclohexylsulfanyl]-acetyl}-mutilin, 14-O-{[(1R,2R,5R)-2-Hydroxy-5-[((R)-piperidine-2-carbonyl)-amino]-cyclohexylsulfanyl]-acetyl}-mutilin, 14-O-{[(1S,2S,5S)-5-((R)-2-Amino-3-hydroxy-propionylamino)-2-hydroxy-cyclohexylsulfanyl]-acetyl}-mutilin and the (1R,2R,5R) diastereomer thereof, 14-O-[((1S,2S,4S)-4-Formylamino-2-hydroxy-cyclohexylsulfanyl)-acetyl]-mutilin and the (1R,2R,4R) diastereomer thereof, 14-O—[((1S,2S,4S)-4-Acetylamino-2-hydroxy-cyclohexylsulfanyl)-acetyl]-mutilin and the (1R,2R,4R) diastereomer thereof, 14-O—[((1S,2S,4S)-2-Hydroxy-4-isobutyrylamino-cyclohexylsulfanyl)-acetyl]-mutilin and the (1R,2R,4R) diastereomer thereof, 14-O-{[(1S,2S,4S)-4-(2,2-Dimethyl-propionylamino)-2-hydroxy-cyclohexylsulfanyl]-acetyl}-mutilin and the (1R,2R,4R) diastereomer thereof, 14-O-{[(1S,2S,4S)-4-(Cyclopropanecarbonyl-amino)-2-hydroxy-cyclohexylsulfanyl]-acetyl}-mutilin and the (1R,2R,4R) diastereomer thereof, 14-O—[((1S,2S,5R)-5-Formylamino-2-hydroxy-cyclohexylsulfanyl)-acetyl]-mutilin and the (1R,2R,5S) diastereomer thereof, 14-O—[((1S,2S,5R)-5-Formylamino-2-formyloxy-cyclohexylsulfanyl)-acetyl]-mutilin and the (1R,2R,5S) diastereomer thereof, 14-O—[((1S,2S,5R)-5-Acetylamino-2-hydroxy-cyclohexylsulfanyl)-acetyl]-mutilin and the (1R,2R,5S) diastereomer thereof, 14-O—[((1S,2S,5R)-2-Acetoxy-5-acetylamino-cyclohexylsulfanyl)-acetyl]-mutilin and the (1R,2R,5S) diastereomer thereof, 14-O—[((1S,2S,5R)-2-Hydroxy-5-isobutyrylamino-cyclohexylsulfanyl)-acetyl]-mutilin and the (1R,2R,5S) diastereomer thereof, 14-O-{[(1S,2S,5R)-5-(2,2-Dimethyl-propionylamino)-2-hydroxy-cyclohexylsulfanyl]-acetyl}-mutilin and the (1R,2R,5S) diastereomer thereof, 14-O-{[(1S,2S,5R)-5-(Cyclopropanecarbonyl-amino)-2-hydroxy-cyclohexylsulfanyl]-acetyl}-mutilin and the (1R,2R,5S) diastereomer thereof, 14-O—[((1S,2S,5S)-5-Formylamino-2-hydroxy-cyclohexylsulfanyl)-acetyl]-mutilin and the (1R,2R,5R) diastereomer thereof, 14-O—[((1S,2S,5S)-5-Acetylamino-2-hydroxy-cyclohexylsulfanyl)-acetyl]-mutilin and the (1R,2R,5R) diastereomer thereof, 14-O—[((1S,2S,5S)-2-Hydroxy-5-isobutyrylamino-cyclohexylsulfanyl)-acetyl]-mutilin and the (1R,2R,5R) diastereomer thereof, 14-O-{[(1S,2S,5S)-5-(2,2-Dimethyl-propionylamino)-2-hydroxy-cyclohexylsulfanyl]-acetyl}-mutilin and the (1R,2R,5R) diastereomer thereof, and 14-O-{[(1S,2S,5S)-5-(Cyclopropanecarbonyl-amino)-2-hydroxy-cyclohexylsulfanyl]-acetyl}-mutilin and the (1R,2R,5R) diastereomer thereof.

9. A compound selected from the group consisting of:

14-O-{[(2-hydroxy-, 2-formyloxy- or 2-acetoxy-cyclohexylsulfanyl]-acetyl}-mutilins which are further substituted at the cyclohexyl group by an acylated amino group.

10. A compound according to claim 1 in the form of a salt.

11. A compound according to claim 1 for use as a pharmaceutical.

12. A pharmaceutical composition comprising a compound of claim 1 in association with at least one pharmaceutical excipient, optionally comprising one or more other pharmaceutically active agents.

13. A method of treatment of microbial diseases which comprises administering to a subject in need of such treatment an effective amount of a compound of claim 1, optionally in combination with one or more other pharmaceutically active agents.

* * * * *